(12) United States Patent
Jang et al.

(10) Patent No.: US 12,108,670 B2
(45) Date of Patent: Oct. 1, 2024

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Jae Wan Jang, Cheonan-si (KR); Jong Gwang Park, Cheonan-si (KR); Sun Hee Lee, Cheonan-si (KR); Soung Yun Mun, Cheonan-si (KR); Yun Suk Lee, Cheonan-si (KR); Hak Young Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 636 days.

(21) Appl. No.: 17/305,221

(22) Filed: Jul. 1, 2021

(65) Prior Publication Data
US 2022/0020938 A1    Jan. 20, 2022

(30) Foreign Application Priority Data

Jul. 8, 2020 (KR) ........................ 10-2020-0084067

(51) Int. Cl.
| | |
|---|---|
| *H01L 51/00* | (2006.01) |
| *C07D 493/16* | (2006.01) |
| *C07D 495/16* | (2006.01) |
| *H10K 85/60* | (2023.01) |
| *H10K 50/11* | (2023.01) |
| *H10K 50/15* | (2023.01) |
| *H10K 50/16* | (2023.01) |
| *H10K 50/17* | (2023.01) |
| *H10K 101/10* | (2023.01) |

(52) U.S. Cl.
CPC ....... *H10K 85/6574* (2023.02); *C07D 493/16* (2013.01); *C07D 495/16* (2013.01); *H10K 85/654* (2023.02); *H10K 50/11* (2023.02); *H10K 50/15* (2023.02); *H10K 50/16* (2023.02); *H10K 50/17* (2023.02); *H10K 50/171* (2023.02); *H10K 2101/10* (2023.02)

(58) Field of Classification Search
CPC ............. H01L 51/0073; H01L 51/5016; H01L 51/0067; C07D 493/16; C07D 495/16
USPC ........................................................ 428/690
See application file for complete search history.

(56) References Cited

FOREIGN PATENT DOCUMENTS

KR    20180022574 A  *  3/2018

OTHER PUBLICATIONS

Translation of KR 2018-0022574, Mar. 6, 2018. (Year: 2018).*

* cited by examiner

*Primary Examiner* — Hui H Chin
(74) *Attorney, Agent, or Firm* — Vorys, Sater, Seymour and Pease LLP; Mih Suhn Koh

(57) ABSTRACT

Provided are a novel compound capable of improving the luminous efficiency, stability and lifespan of an element, an organic electronic element using the same, and an electronic device thereof.

13 Claims, 2 Drawing Sheets

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular type and a low molecular type according to the molecular weight, and may be classified into a fluorescent material derived from a singlet excited state of an electron and a phosphorescent material derived from a triplet excited state of an electron according to an emitting mechanism. Also, the light emitting materials may be classified into blue, green, and red light emitting materials and yellow and orange light emitting materials necessary for realizing a better natural color according to the emitting color.

However, when only one material is used as a light emitting material, the maximum light-emitting wavelength shifts to a long wavelength due to intermolecular interactions, and the color purity decreases or the efficiency of the device decreases due to the light-emitting attenuation effect, therefore in order to increase color purity and increase luminous efficiency through energy transfer, a host/dopant system may be used as a light emitting material.

The principle is that when a small amount of a dopant having a smaller energy band gap than that of the host forming the emitting layer is mixed in the emitting layer, excitons generated in the emitting layer are transported to the dopant to emit light with high efficiency. At this time, since the wavelength of the host moves to the wavelength band of the dopant, light having a desired wavelength can be obtained according to the type of dopant used.

Currently, the portable display market is a large-area display, and the size thereof is increasing, so that power consumption greater than the power consumption required for the existing portable display is required. Therefore, power consumption has become a very important factor for a portable display having a limited power supply such as a battery, and efficiency and lifespan problems must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and TI value between each organic material layer, and the intrinsic properties (mobility, interfacial properties, etc.) of materials are optimally combined, long lifespan and high efficiency can be achieved at the same time.

Therefore, there is a need to develop a light emitting material that has high thermal stability and can efficiently achieve charge balance in the emitting layer. That is, in order to fully exhibit the excellent characteristics of the organic electronic device, the material constituting the organic material layer in the device, such as a hole injection material, a hole transport material, a light emitting material, an electron transport material, an electron injection material, etc., should be supported by a stable and efficient material in advance, and among them, it is necessary to develop a host material for the emitting layer.

DETAILED DESCRIPTION OF THE INVENTION

Summary

In order to solve the problems of the background art described above, the present invention has revealed a compound having a novel structure, and also found that when this compound is applied to an organic electronic device, the luminous efficiency, stability and lifespan of the device can be greatly improved.

Accordingly, an object of the present invention is to provide a novel compound, an organic electronic device using the same, and an electronic device thereof.

Technical Solution

The present invention provides a compound represented by Formula (1).

[Formula 1]

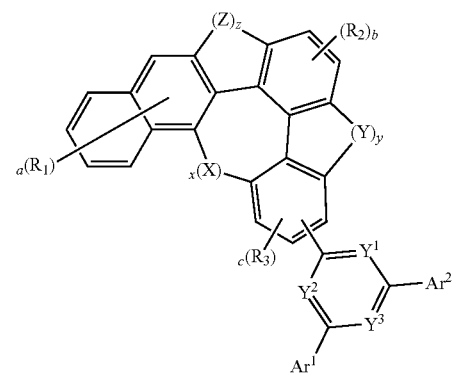

In another aspect, the present invention provides an organic electronic element comprising the compound represented by Formula 1 and an electronic device thereof.

Effects of the Invention

By using the compound according to the present invention, high luminous efficiency, low driving voltage and high heat resistance of the device can be achieved, and color purity and lifespan of the device can be greatly improved.

DETAILED DESCRIPTION

Figure 1:
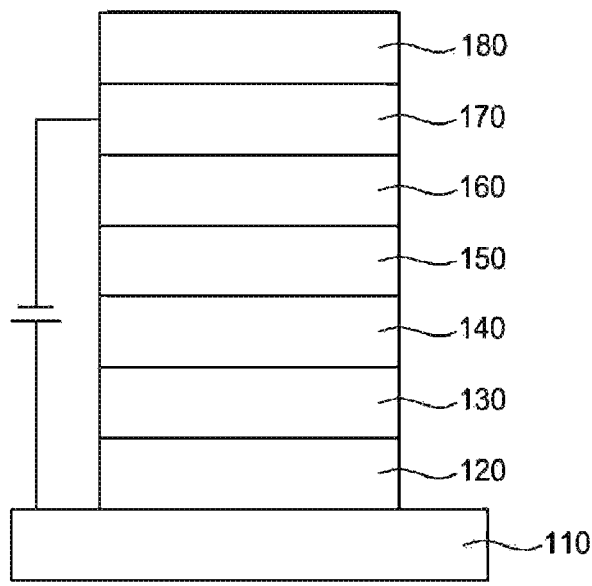
FIG. 1 to FIG. 3 are exemplary views of an organic electroluminescent device according to the present invention.

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

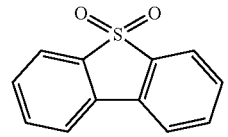 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

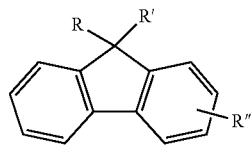

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

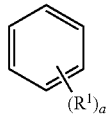

here, when a is an integer of zero, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

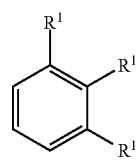

Hereinafter, a compound according to an aspect of the present invention and an organic electronic element including the same will be described.

The present invention provides a compound represented by Formula 1.

[Formula 1]

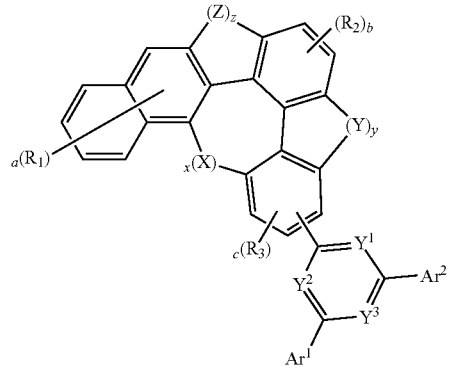

Wherein, each symbol may be defined as follows.
1) $Ar^1$ and $Ar^2$ are each independently a $C_6$-$C_{60}$ aryl group; or a $C_2$-$C_{60}$ heterocyclic group including at least one hetero atom of O, N, S, Si or P;
When $Ar^1$ and $Ar^2$ may be an aryl group, they may be preferably a $C_6$-$C_{30}$ aryl group, more preferably a $C_6$-$C_{24}$ aryl group, such as phenylene, biphenyl, naphthalene, terphenyl, etc.;
When $Ar^1$ and $Ar^2$ are heteroaryl groups, they may be preferably a $C_6$-$C_{30}$ heteroaryl group, more preferably a $C_6$-$C_{24}$ heteroaryl group,
2) $Y^1$, $Y^2$ and $Y^3$ are each independently N or CR', provided that at least one is N.
3) wherein R' is selected from the group consisting of hydrogen; deuterium; halogen; $C_1$-$C_{60}$ alkyl group; a $C_2$-$C_{60}$ alkenyl group; a $C_2$-$C_{60}$ alkynyl group; a $C_1$-$C_{60}$ alkoxyl group; a $C_6$-$C_{60}$ aryloxy group; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;
When R' is an alkyl group, it may be preferably a $C_1$-$C_{30}$ alkyl group, and more preferably a $C_1$-$C_{24}$ alkyl group.
When R' is an alkenyl group, it may be preferably a $C_2$-$C_{30}$ alkenyl group, and more preferably a $C_2$-$C_{24}$ alkenyl group.
When R' is an alkynyl group, it may be preferably a $C_2$-$C_{30}$ alkynyl group, and more preferably a $C_2$-$C_{24}$ alkynyl group.
When R' is an alkoxyl group, it may be preferably a $C_1$-$C_{30}$ alkoxyl group, and more preferably a $C_1$-$C_{24}$ alkoxyl group.
When R' is an aryloxy group, it may be preferably a $C_6$-$C_{30}$ aryloxy group, and more preferably a $C_6$-$C_{24}$ aryloxy group.
When R' is an aryl group, it may be preferably a $C_6$-$C_{30}$ aryl group, and more preferably a $C_6$-$C_{24}$ aryl group, for example, it may be phenylene, biphenyl, naphthalene, terphenyl, etc.
When R' is a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazole, dibenzofuran, benzothienopyrimidine, benzofuropyrimidine, phenothiazine, phenylphenothiazine, etc.

When R' is a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

4) X, Y and Z are each independently O or S.

5) $R^1$, $R^2$ and $R^3$ are each the same or different, and each independently selected from a group consisting of hydrogen; deuterium; halogen; a $C_1$-$C_{60}$ alkyl group; a $C_2$-$C_{60}$ alkenyl group; a $C_2$-$C_{60}$ alkynyl group; a $C_1$-$C_{60}$ alkoxyl group; a $C_6$-$C_{60}$ aryloxy group; a $C_6$-$C_{60}$ aryl group a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; and -L'-N($R^a$)($R^b$);

When $R^1$, $R^2$ and $R^3$ are an alkyl group, they may be preferably an $C_1$-$C_{30}$ alkyl group, more preferably an $C_1$-$C_{24}$ alkyl group.

When $R^1$, $R^2$ and $R^3$ are an alkenyl group, they may be preferably an $C_2$-$C_{30}$ alkenyl group, more preferably an $C_2$-$C_{24}$ alkenyl group.

When $R^1$, $R^2$ and $R^3$ are an alkynyl group, they may be preferably a $C_2$-$C_{30}$ alkynyl group, and more preferably a $C_2$-$C_{24}$ alkynyl group.

When $R^1$, $R^2$ and $R^3$ are an alkoxyl group, they may be preferably a $C_1$-$C_{30}$ alkoxyl group, and more preferably a $C_1$-$C_{24}$ alkoxyl group.

When $R^1$, $R^2$ and $R^3$ are an aryloxy group, they may be preferably a $C_6$-$C_{30}$ aryloxy group, and more preferably a $C_6$-$C_{24}$ aryloxy group.

When $R^1$, $R^2$ and $R^3$ are an aryl group, they may be preferably a $C_6$-$C_{30}$ aryl group, and more preferably a $C_6$-$C_{24}$ aryl group, for example, phenylene, biphenyl, naphthalene, terphenyl, etc.

When $R^1$, $R^2$ and $R^3$ are a heterocyclic group, they may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazole, dibenzofuran, benzothienopyrimidine, benzofuropyrimidine, phenothiazine, phenylphenothiazine, etc.

When $R^1$, $R^2$ and $R^3$ are a fused ring group, they may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

6) wherein L' is each independently selected from the group consisting of single bond; a $C_6$-$C_{60}$ arylene group; a fluorenylene group; a $C_2$-$C_{60}$ heterocyclic group including at least one heteroatom of O, N, S, Si or P; and a $C_3$-$C_{60}$ aliphatic ring; wherein $R^a$ and $R^b$ are each independently selected from the group consisting of a $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

When L' is an arylene group, it may be preferably a $C_6$-$C_{30}$ arylene group, more preferably a $C_6$-$C_{24}$ arylene group, for example, phenylene, biphenyl, naphthalene, terphenyl, etc.

When L' is a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazole, dibenzofuran, benzothienopyrimidine, benzofuropyrimidine, phenothiazine, phenylphenothiazine, etc.

When L' is an aliphatic ring group, it may be preferably an $C_3$-$C_{30}$ aliphatic ring, and more preferably an $C_3$-$C_{24}$ aliphatic ring, When $R^a$ and $R^b$ are an aryl group, they may be preferably a $C_6$-$C_{30}$ aryl group, and more preferably a $C_6$-$C_{25}$ aryl group, for example, phenyl, biphenyl, naphthyl, phenanthrene, terphenyl, etc.

When $R^a$ and $R^b$ are a heterocyclic group, they may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazole, dibenzofuran, benzothienopyrimidine, benzofuropyrimidine, phenothiazine, phenylphenothiazine, etc.

When $R^a$ and $R^b$ are a fused ring group, they may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

7) x, y and z are each independently 0 or 1, 8) a is an integer from 0 to 5, b and c are each independently an integer from 0 to 2, 9) wherein, the aryl group, heteroaryl group, arylene group, heterocyclic group, fluorenyl group, fluorenylene group, fused ring group, alkyl group, alkenyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; $C_8$-$C_{20}$ arylalkenyl group; and -L'-N($R^a$)($R^b$); or the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, the present invention includes a compound in which Formula 1 is represented by any one of Formulas 1-1 to 1-8.

[Formula 1-1]

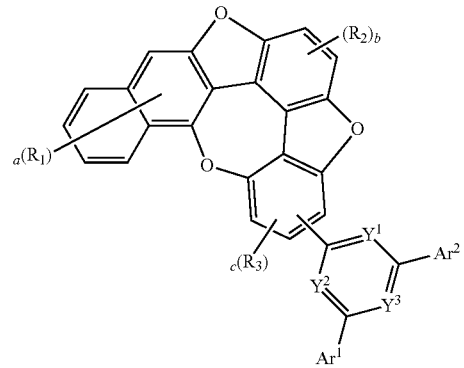

[Formula 1-2]
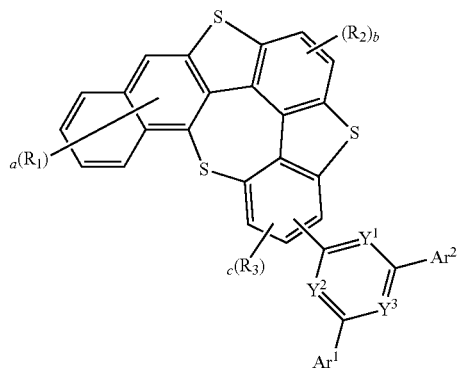
[Formula 1-3]
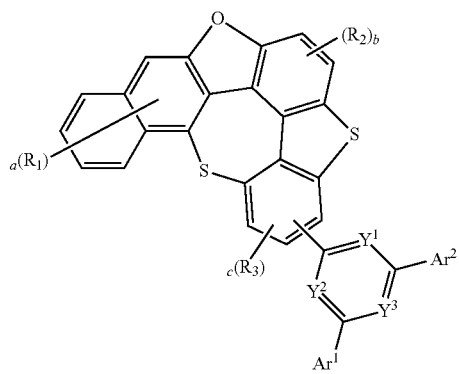
[Formula 1-4]
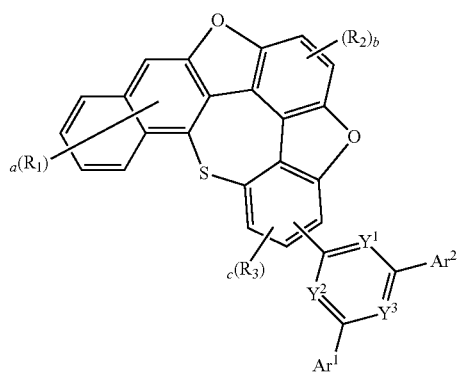
[Formula 1-5]
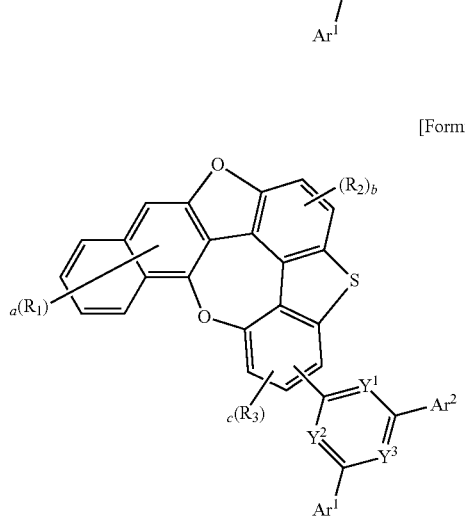
[Formula 1-6]
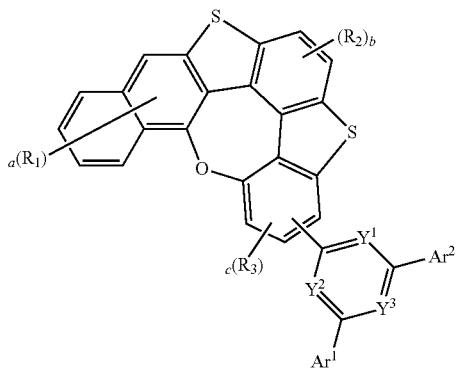
[Formula 1-7]
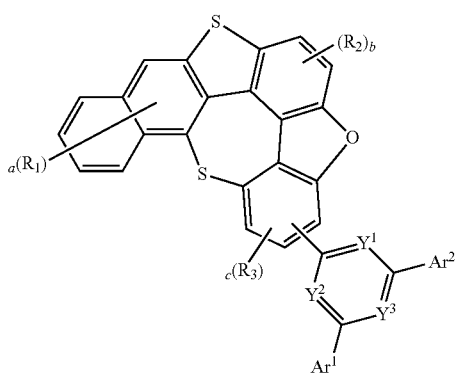
[Formula 1-8]
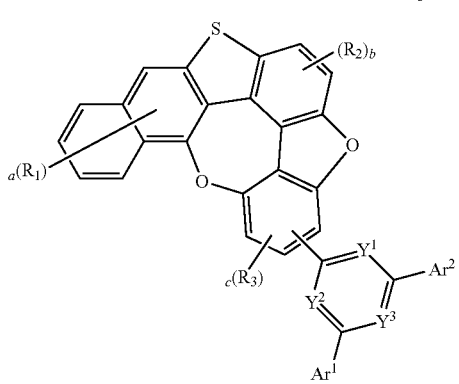

{wherein,
Ar¹, Ar², Y¹, Y², Y³, R₁, R₂, R₃, a, b and c are the same as defined in claim 1}
Also, Formula 1 is represented by any one of Formulas 1-9 to 1-13
[Formula 1-9]
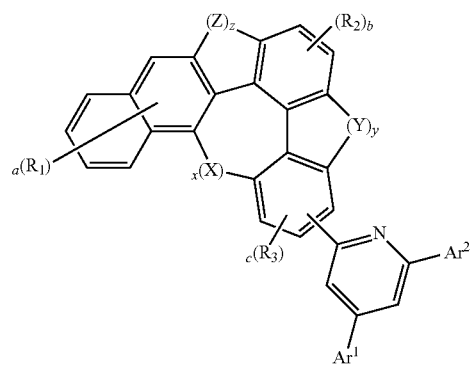
[Formulas 1-10]
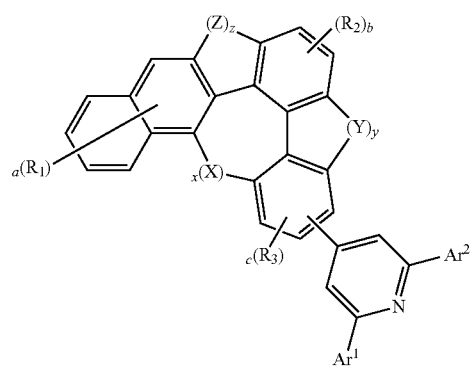
[Formulas 1-11]
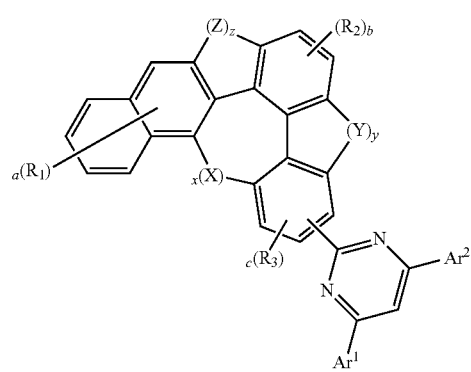
[Formulas 1-12]
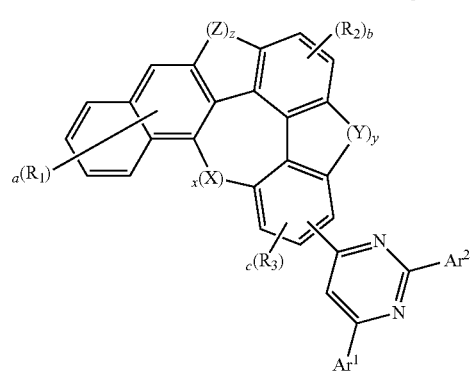
[Formulas 1-13]
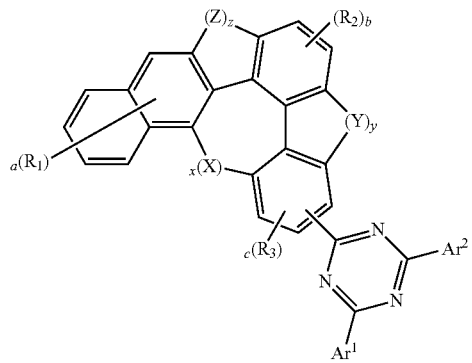
{wherein,
Ar¹, Ar², X, Y, Z, R₁, R₂, R₃, x, r, z, a, b and c are the same as defined in claim 1}
Also, Formula 1 is represented by any one of Formulas 1-14 to 1-16
[Formula 1-14]
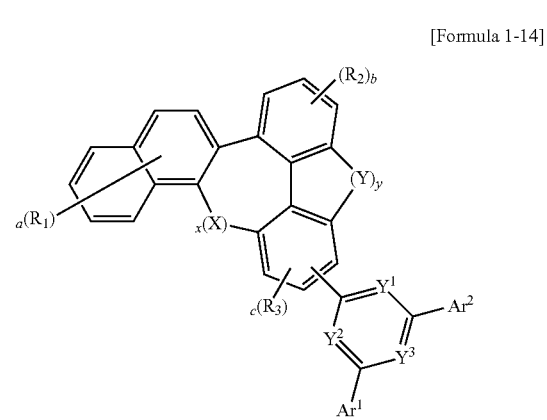
[Formula 1-15]
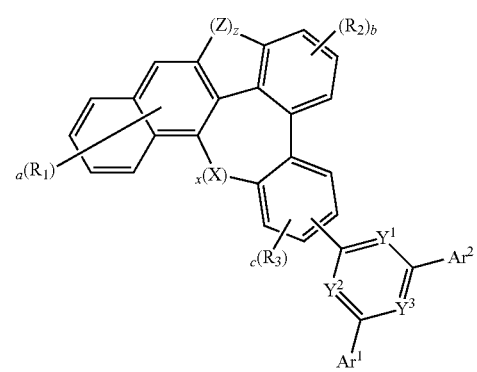

[Formula 1-16]
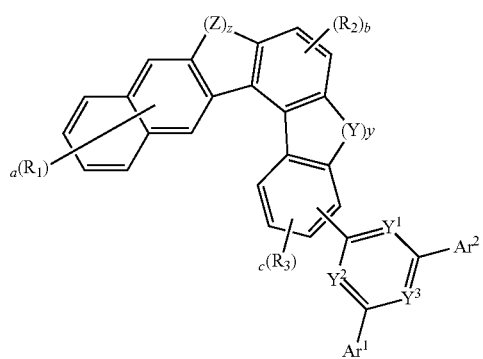
{wherein,
Ar$^1$, Ar$^2$, Y$^1$, Y$^2$, Y$^3$, X, Y, Z, R$_1$, R$_2$, R$_3$, x, y, z, a, b and c are the same as defined in claim 1}
Specifically, the compound represented by Formula 1 may be any one of the following compounds P-1 to P-80, but is not limited thereto.
P-1
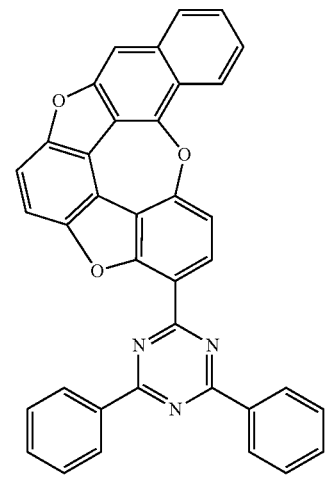
P-2
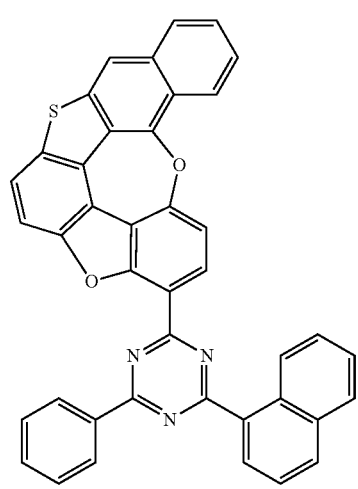
P-3
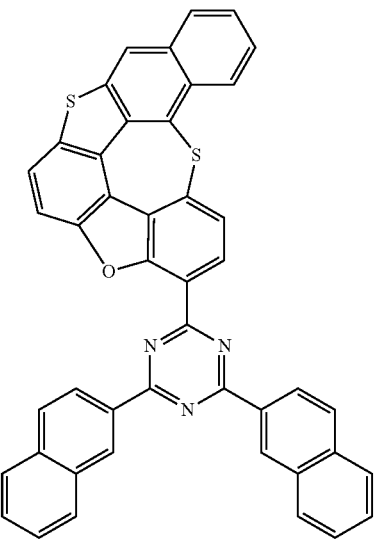
P-4
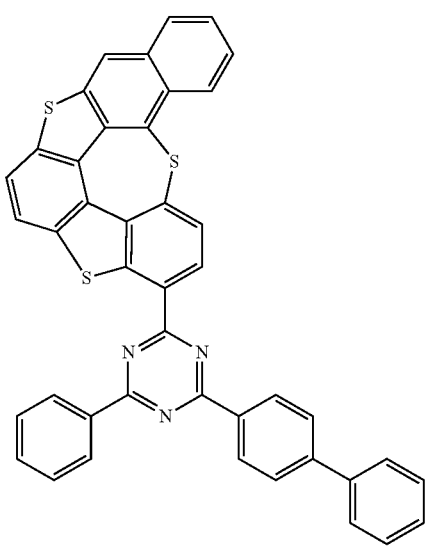
P-5
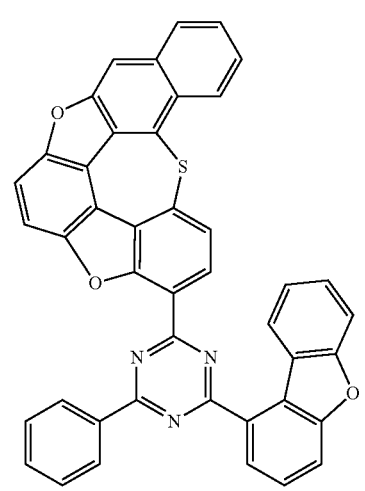

-continued
P-6
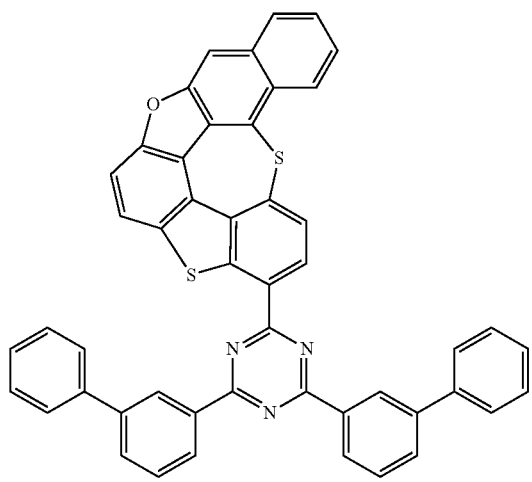
P-7
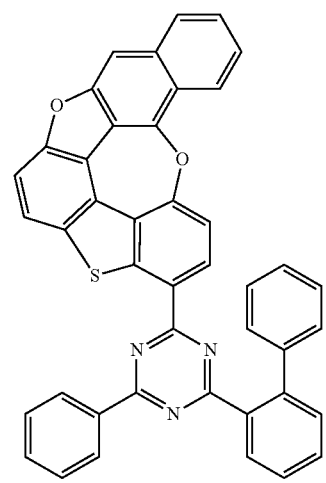
P-8
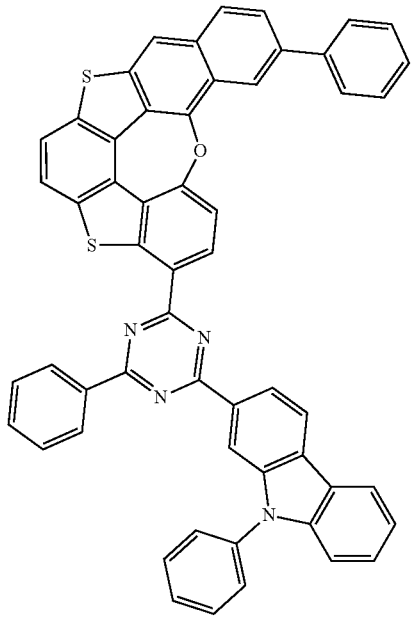
P-9
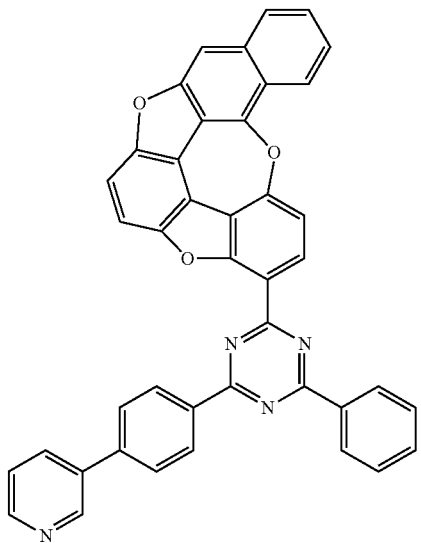
P-10
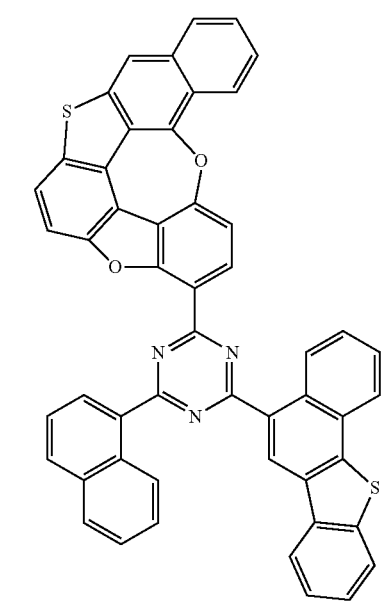
P-11
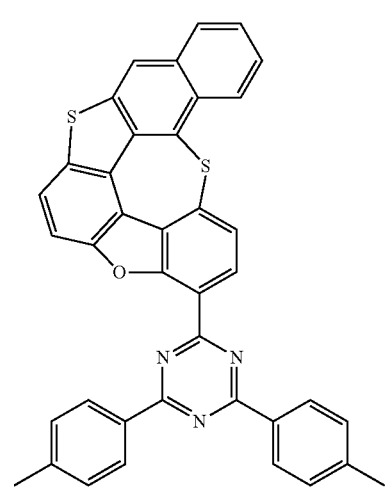

-continued
P-12
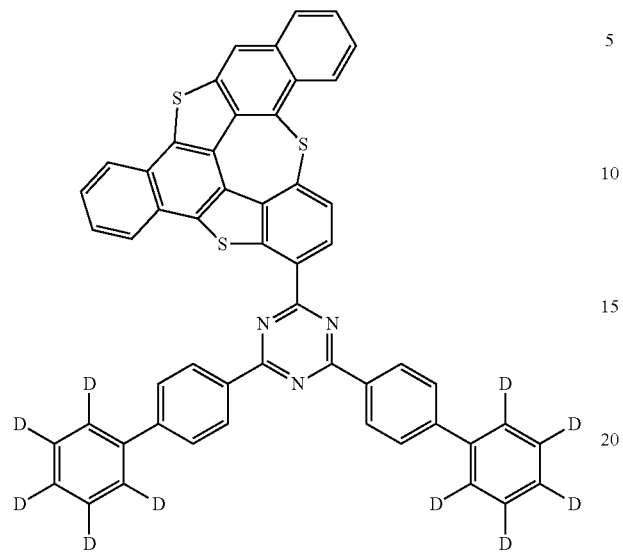
P-13
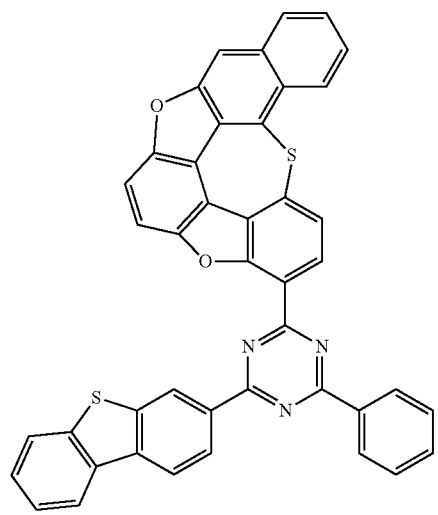
P-14
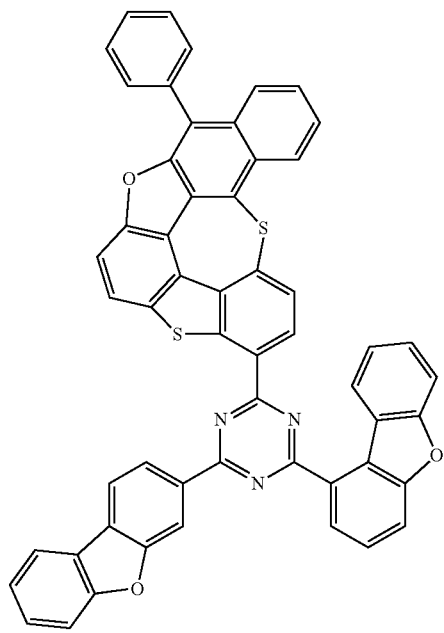
P-15
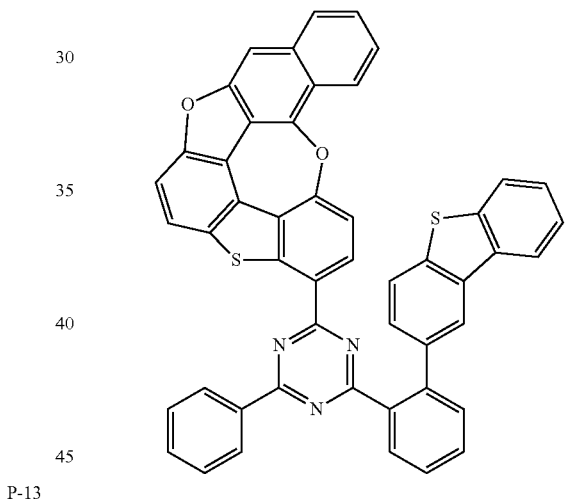
P-16

-continued
P-17
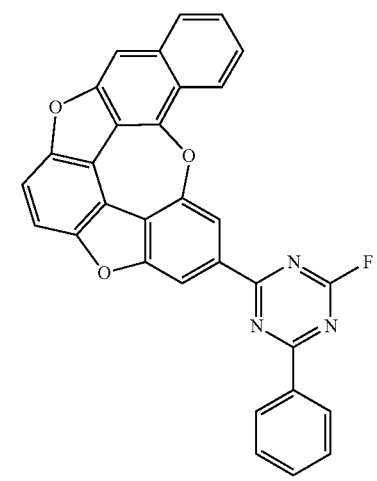
P-18
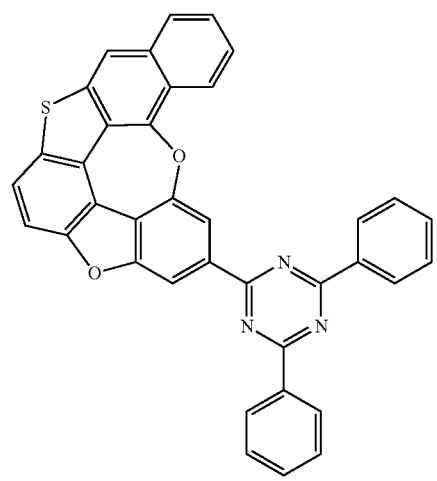
P-19
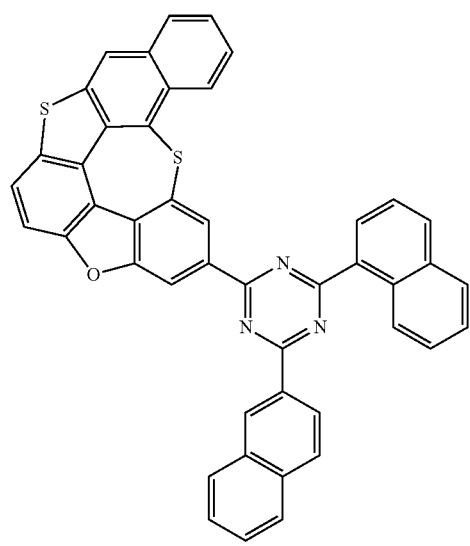
P-20
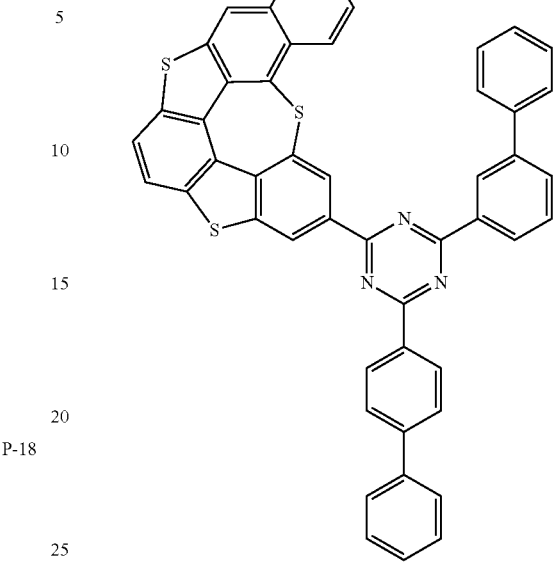
P-21
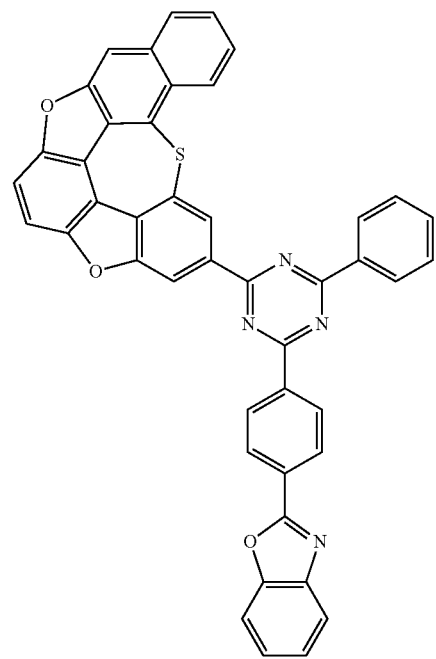

-continued
P-22
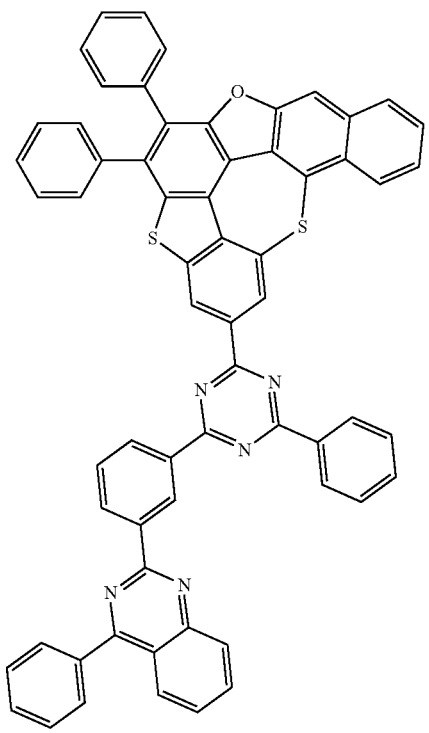
P-23
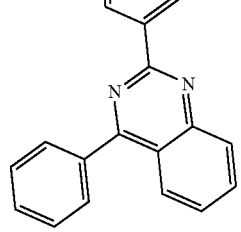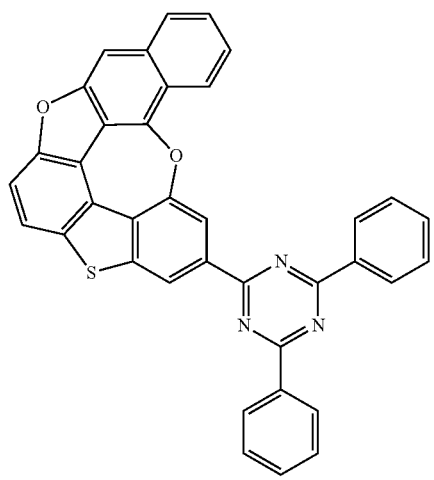
P-24
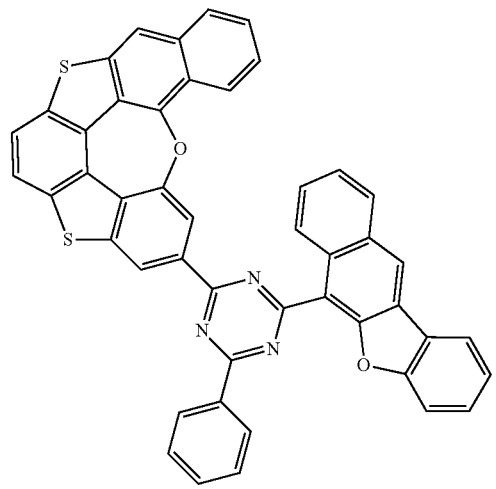
P-25
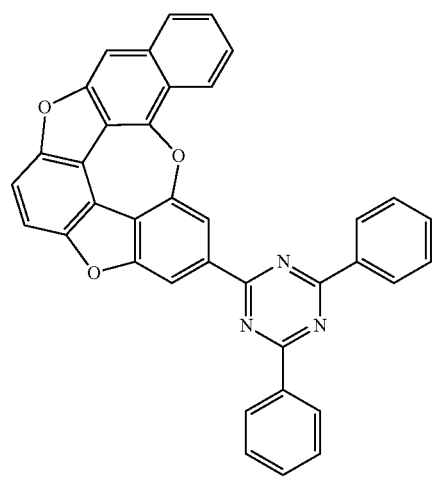
P-26
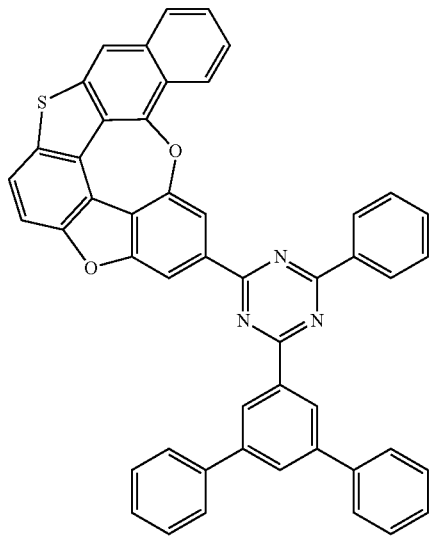

P-27
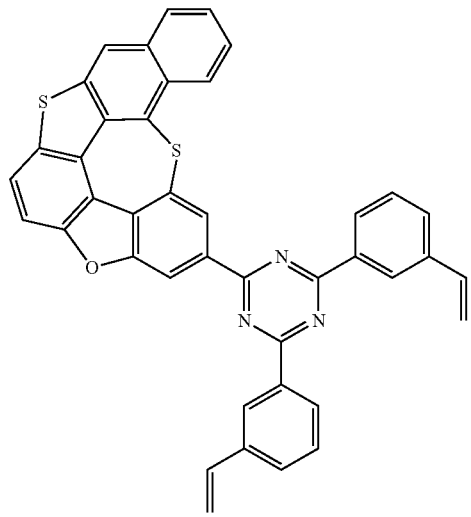
P-28
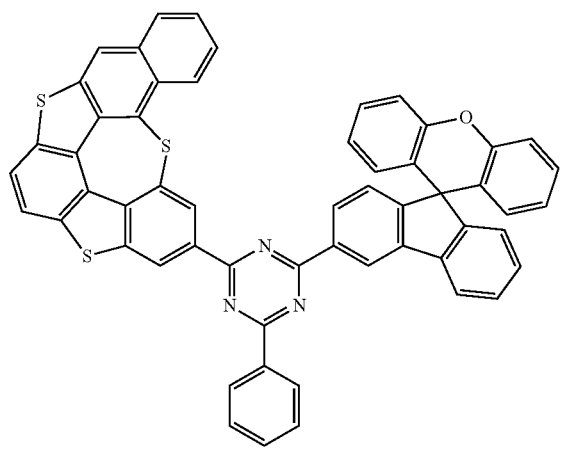
P-29
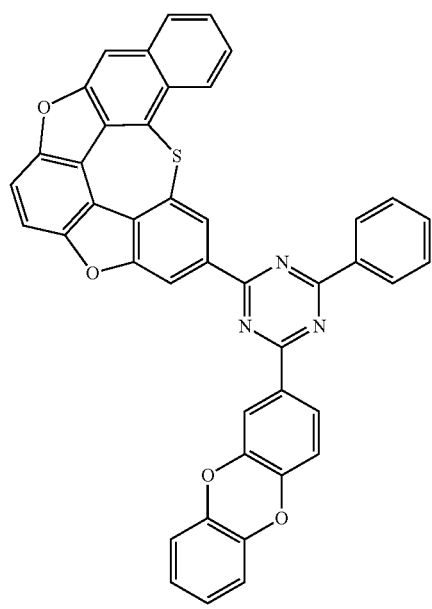
P-30
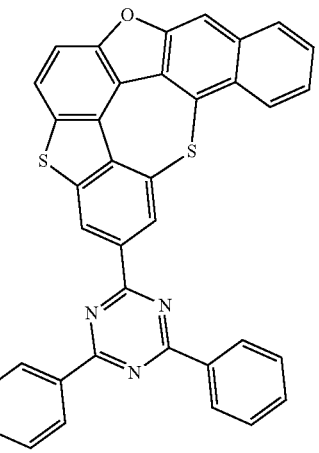
P-31
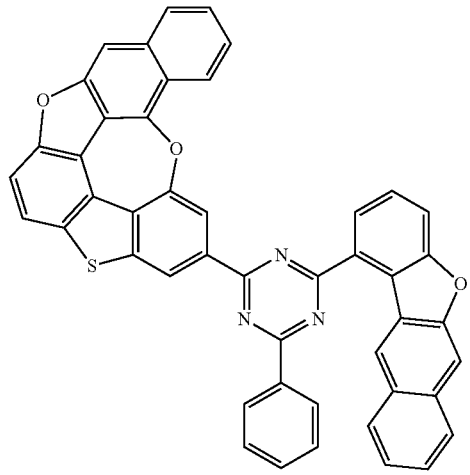
P-32
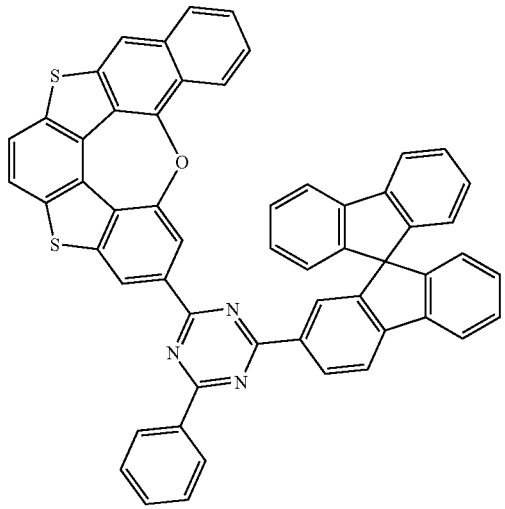

P-33
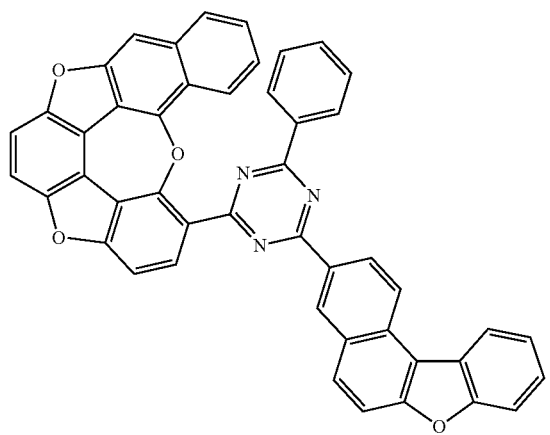
P-34
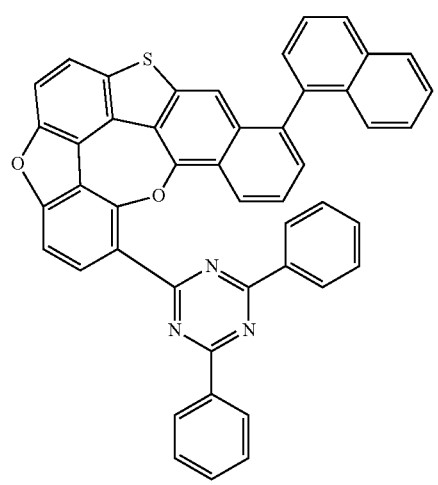
P-35
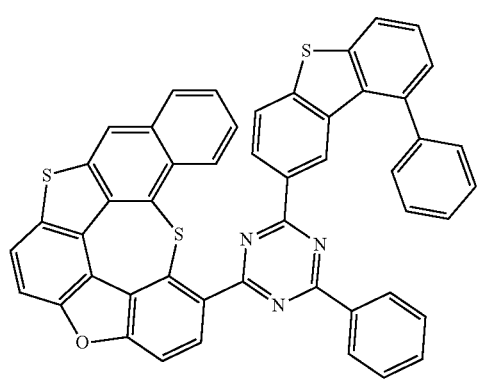
P-36
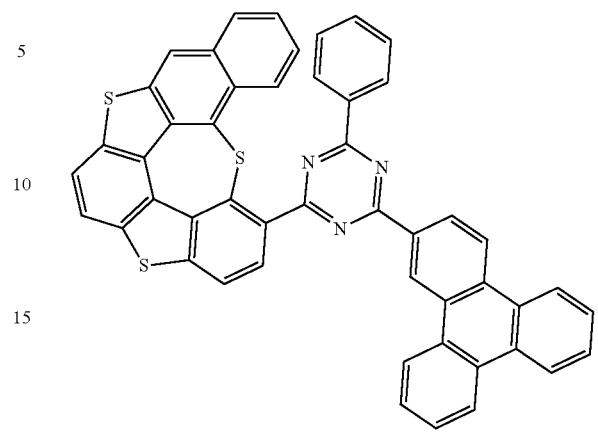
P-37
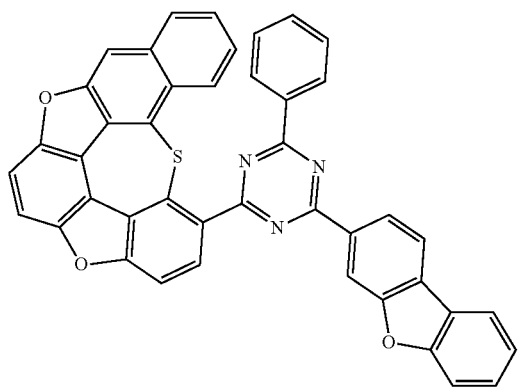
P-38
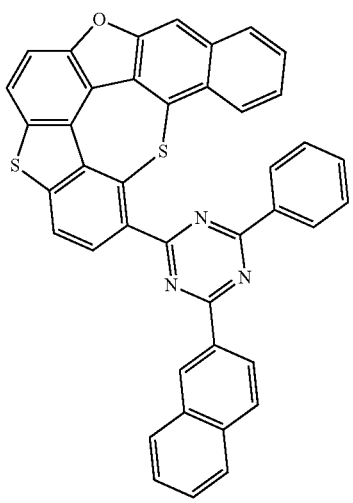

P-39
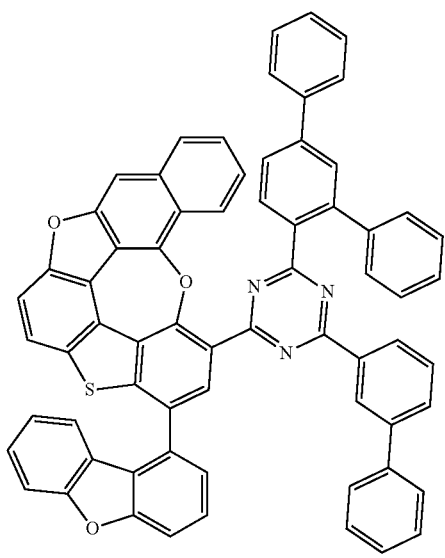
P-40
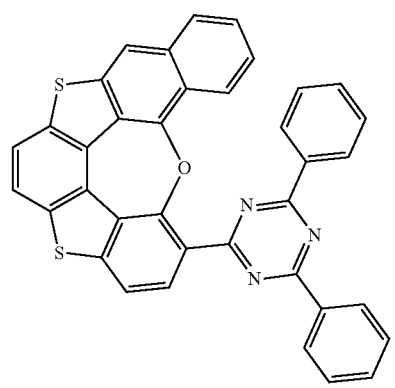
P-41
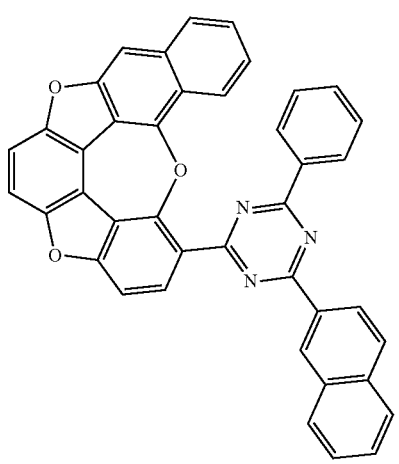
P-42
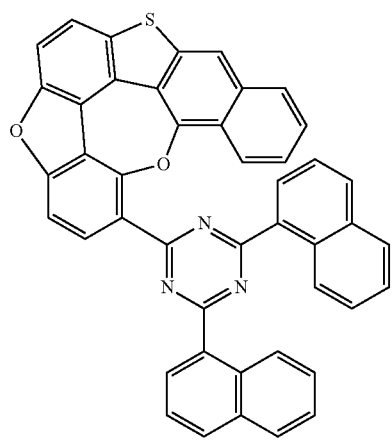
P-43
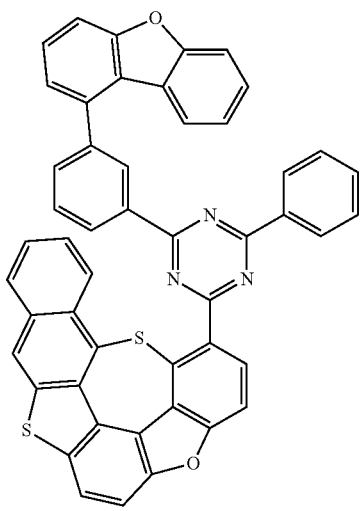
P-44
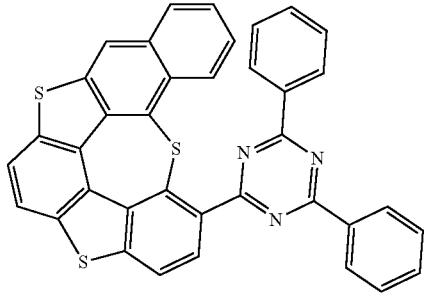

-continued
P-45
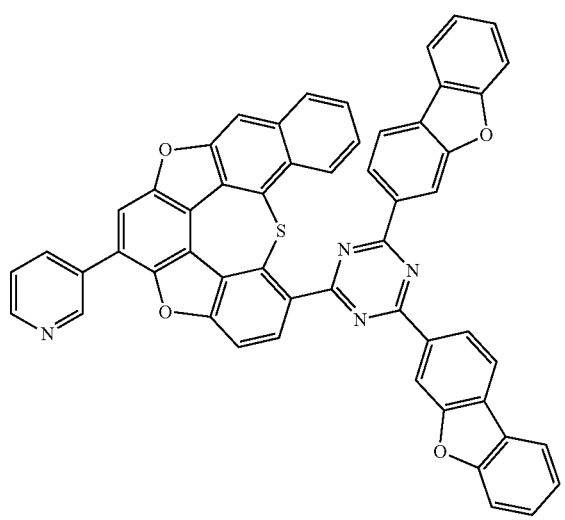
P-46
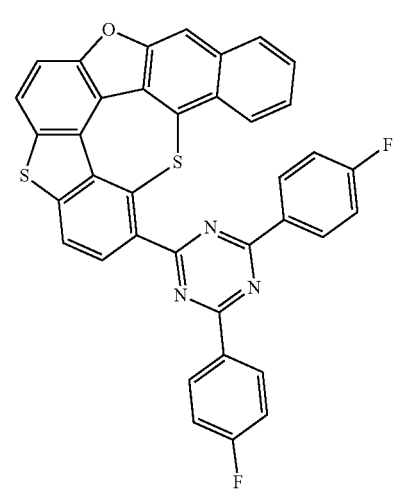
P-47
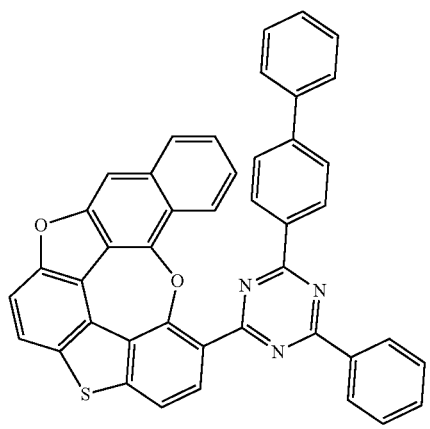
-continued
P-48
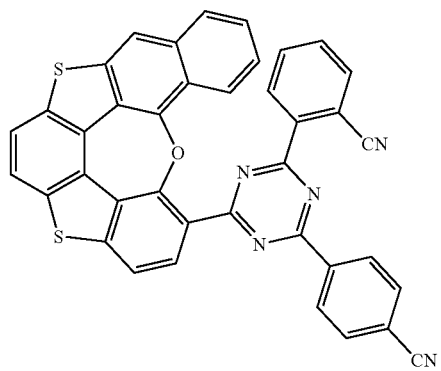
P-49
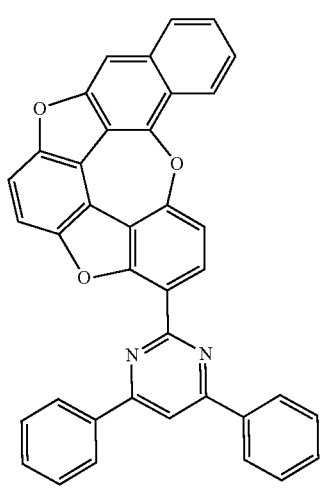
P-50
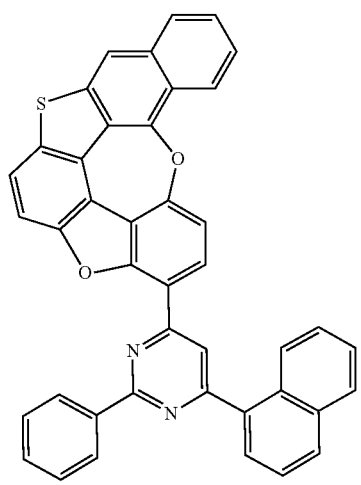

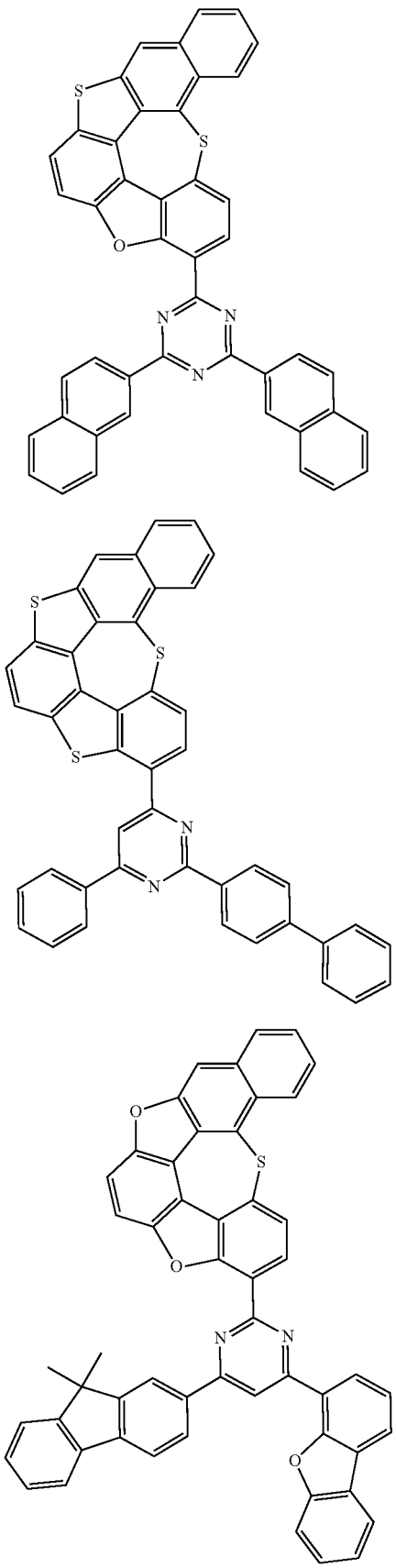

P-56
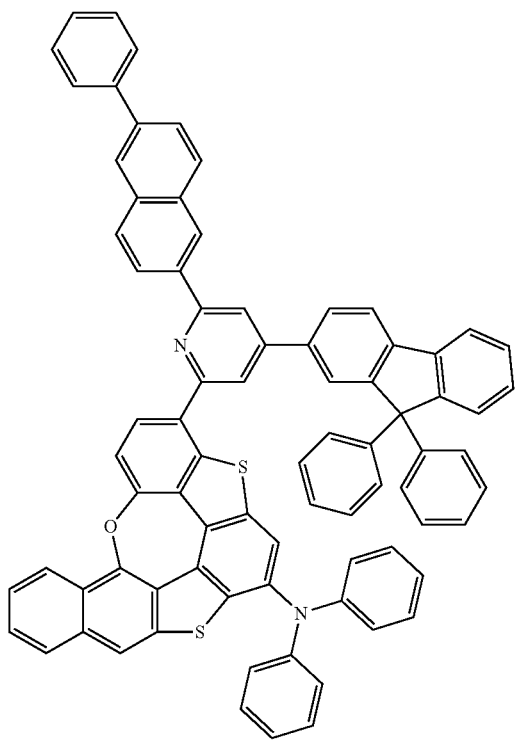
P-58
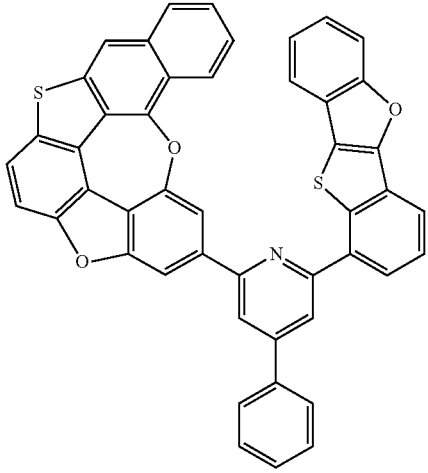
P-59
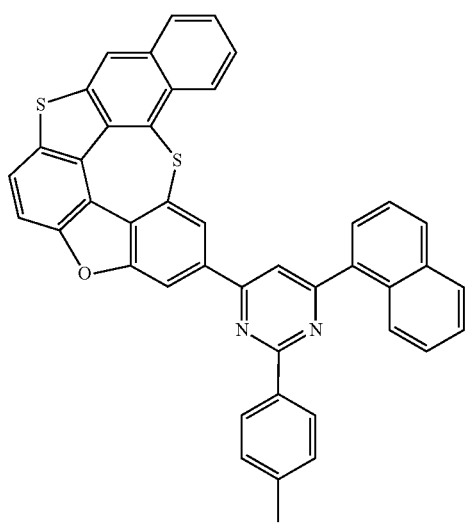
P-57
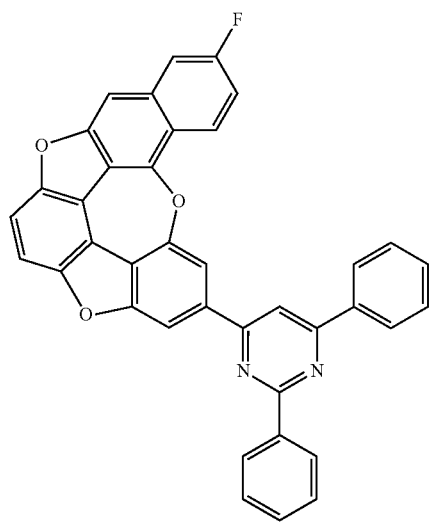
P-60
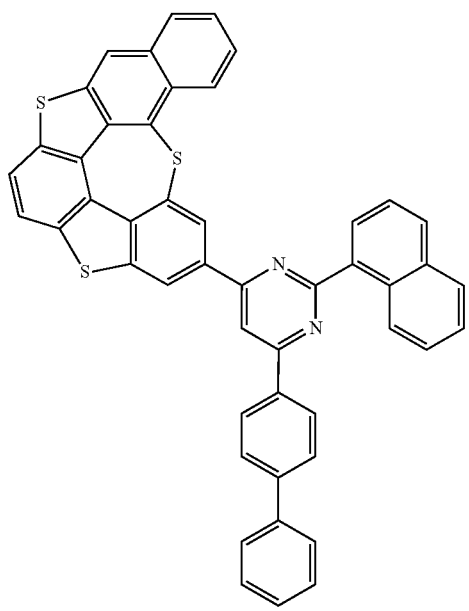

P-61
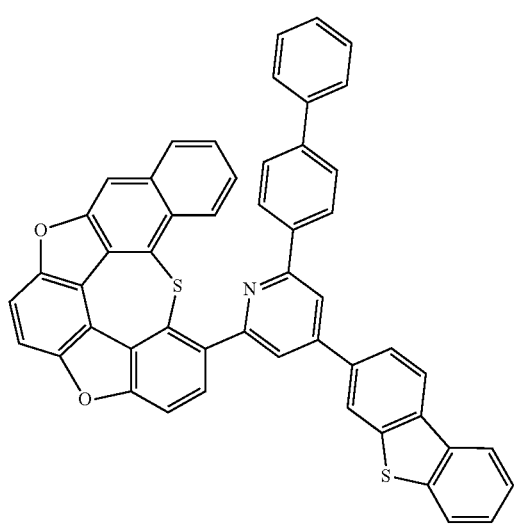
P-62
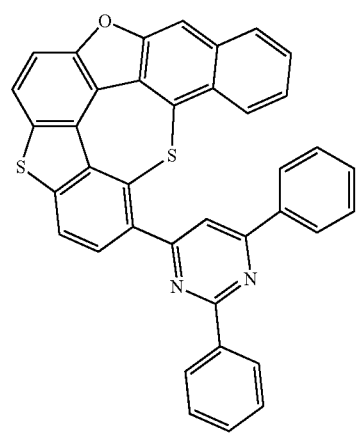
P-63
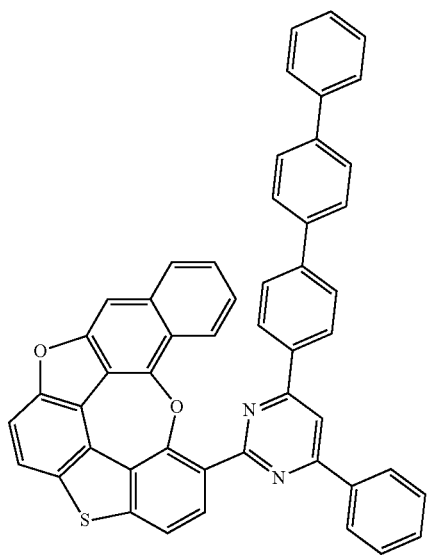
P-64
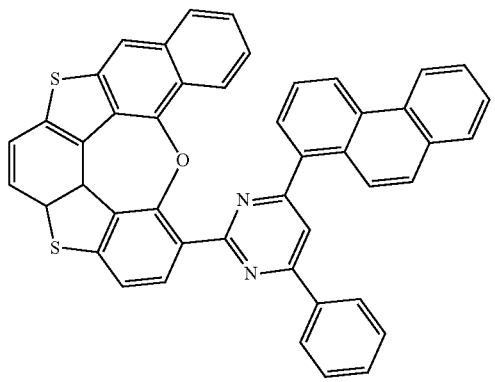
P-65
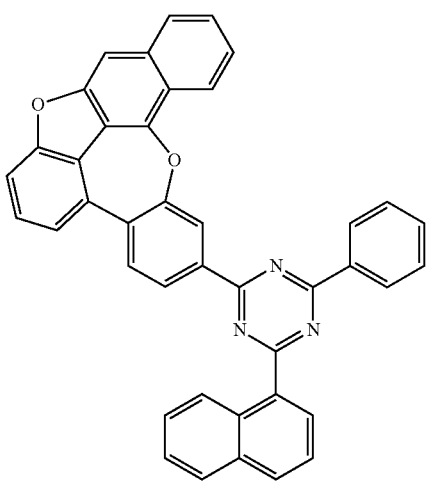
P-66
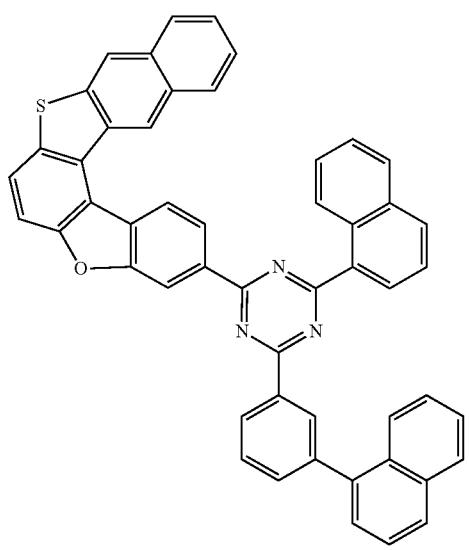

-continued
P-67
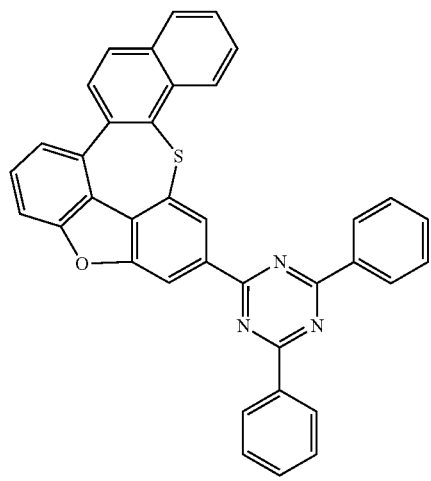
P-68
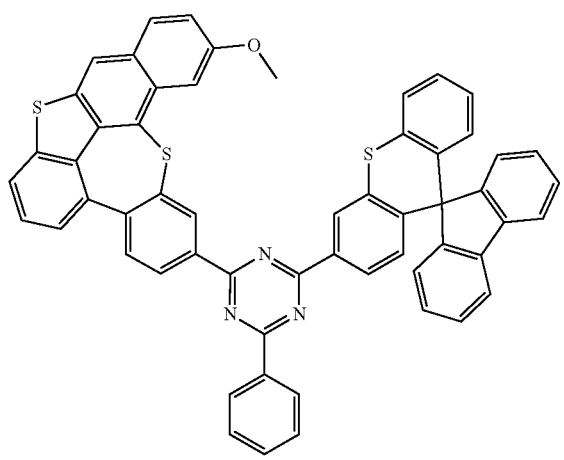
P-69
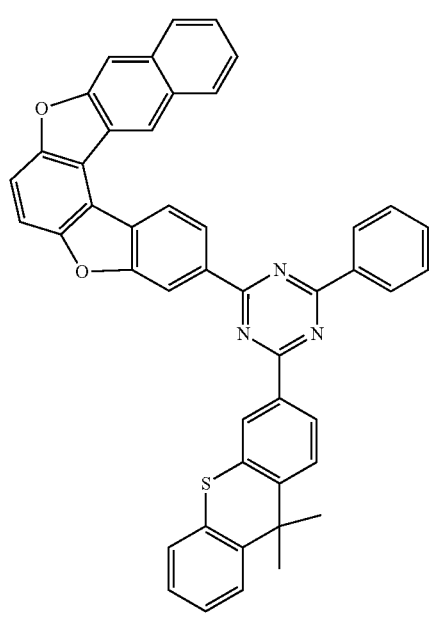
-continued
P-70
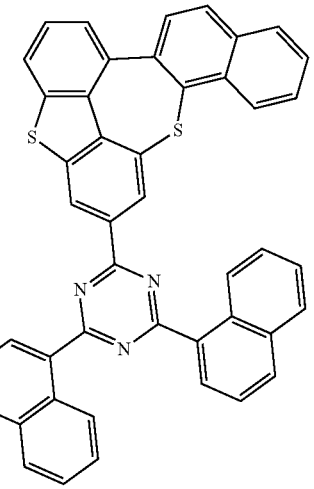
P-71
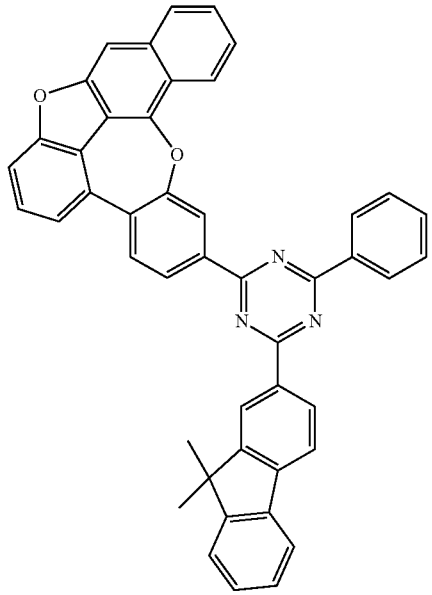
P-72
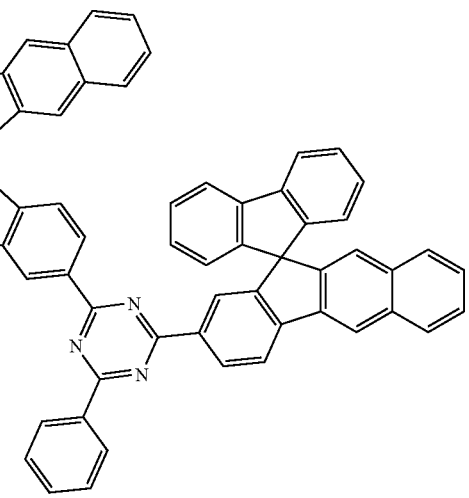

P-73
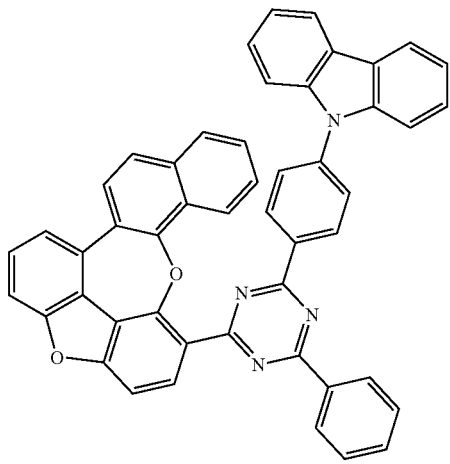
P-74
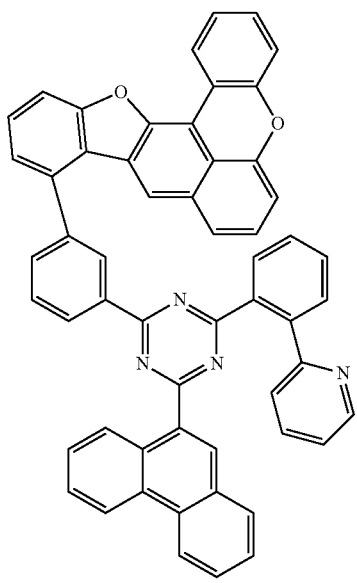
P-75
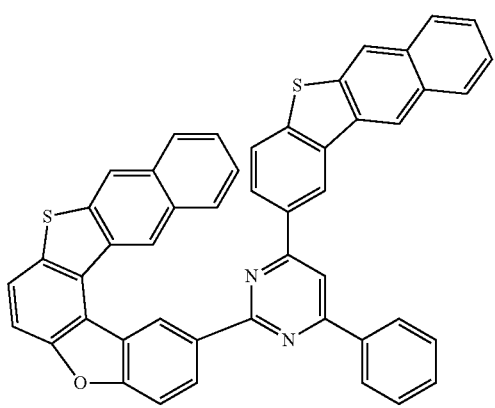
P-76
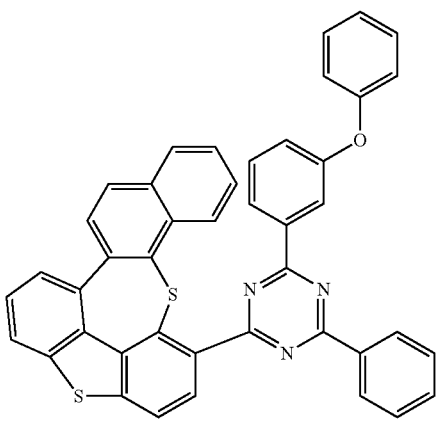
P-77
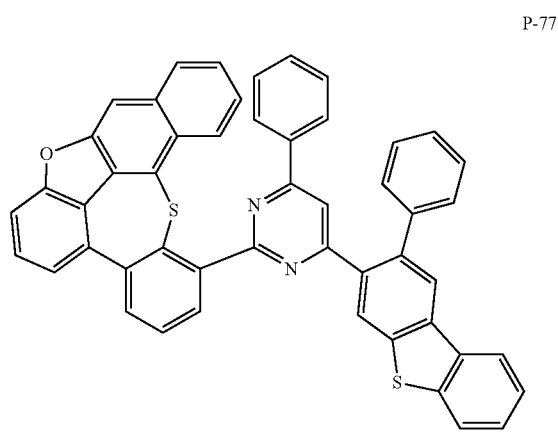
P-78
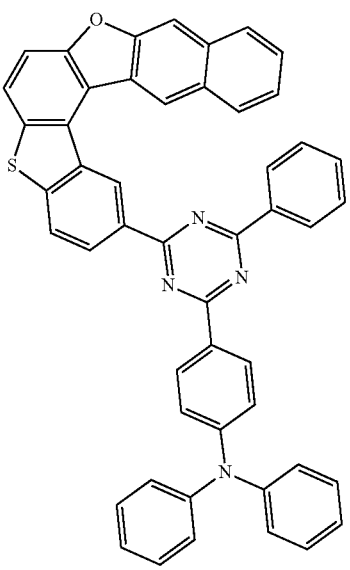

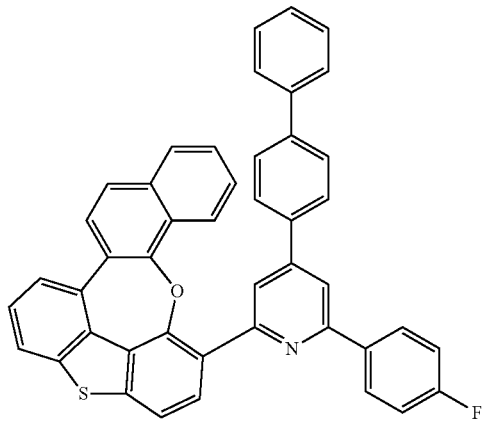

P-79

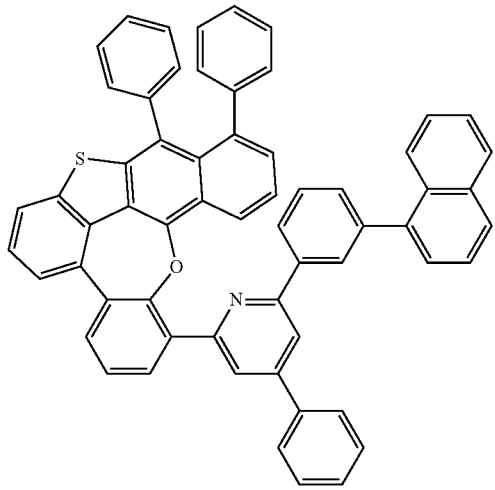

P-80

Referring to FIG. 1, the organic electronic element (100) according to the present invention includes a first electrode (110), a second electrode (170), and an organic material layer including a single compound or 2 or more compounds represented by Formula 1 between the first electrode (110) and the second electrode (170). In this case, the first electrode (110) may be an anode, and the second electrode (170) may be a cathode. In the case of an inverted type, the first electrode may be a cathode and the second electrode may be an anode.

Figure 2:
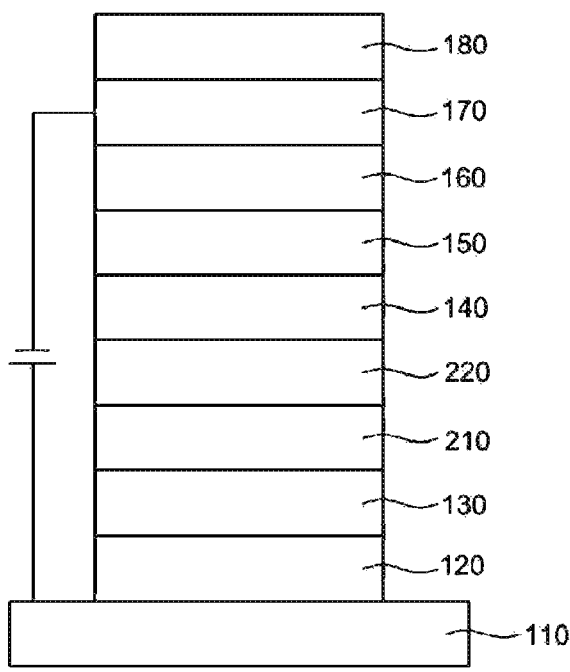

The organic material layer may sequentially include a hole injection layer (120), a hole transport layer (130), an emitting layer (140), an electron transport layer (150), and an electron injection layer (160) on the first electrode (110). In this case, the remaining layers except for the emitting layer (140) may not be formed. It may further include a hole blocking layer, an electron blocking layer, an emitting auxiliary layer (220), a buffer layer (210), etc. and the electron transport layer (150) and the like may serve as a hole blocking layer. (See FIG. 2) Also, the organic electronic element according to an embodiment of the present invention may further include a protective layer or a light efficiency enhancing layer (180). The light efficiency enhancing layer may be formed on one of both surfaces of the first electrode not in contact with the organic material layer or on one of both surfaces of the second electrode not in contact with the organic material layer. The compound according to an embodiment of the present invention applied to the organic material layer may be used as a host or dopant of the hole injection layer (120), the hole transport layer (130), the emitting auxiliary layer (220), electron transport auxiliary layer, the electron transport layer (150), and an electron injection layer (160), the emitting layer (140) or as a material for the light efficiency enhancing layer. Preferably, for example, the compound according to Formula 1 of the present invention may be used as a phosphorescent host material of the emitting layer.

Figure 3:
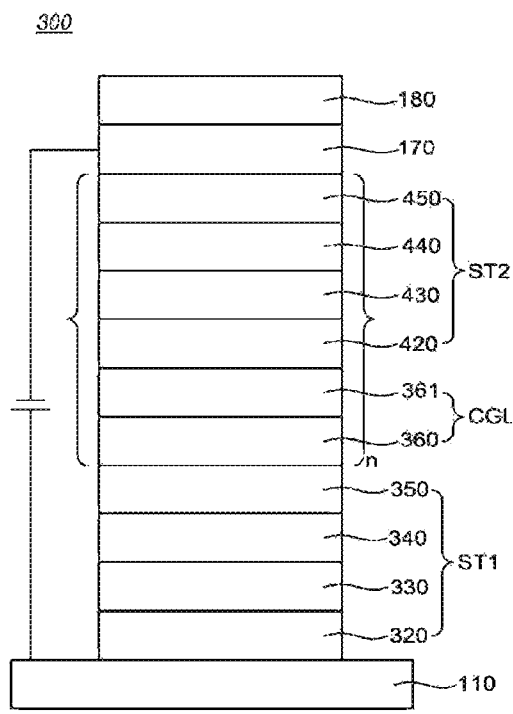
Figure 4:
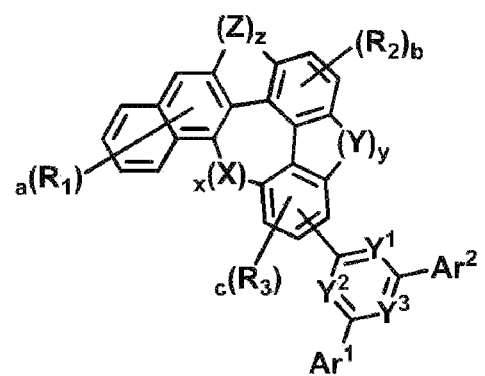
FIG. 4 shows a Formula according to an aspect of the present invention.

The organic material layer may include 2 or more stacks including a hole transport layer, an emitting layer and an electron transport layer sequentially formed on the anode, further include a charge generation layer formed between the 2 or more stacks (see FIG. 3).

Otherwise, even with the same core, the band gap, electrical characteristics, interface characteristics, etc. may vary depending on which position the substituent is bonded to, therefore the choice of core and the combination of sub-substituents bound thereto are also very important, and in particular, when the optimal combination of energy levels and T1 values and unique properties of materials (mobility, interfacial characteristics, etc.) of each organic material layer is achieved, a long lifespan and high efficiency can be achieved at the same time. The organic electroluminescent device according to an embodiment of the present invention may be manufactured using a PVD (physical vapor deposition) method. For example, depositing a metal or a metal oxide having conductivity or an alloy thereof on a substrate to form an anode, and after forming an organic material layer including the hole injection layer (120), the hole transport layer (130), the emitting layer (140), the electron transport layer (150) and the electron injection layer (160) thereon, it can be prepared by depositing a material that can be used as a cathode thereon.

Also, in the present invention, the organic material layer is formed by any one of a spin coating process, a nozzle printing process, an inkjet printing process, a slot coating process, a dip coating process, and a roll-to-roll process, and the organic material layer provides an organic electric element comprising the compound as an electron transport material.

As another specific example, the same or different compounds of the compound represented by Formula 1 are mixed and used in the organic material layer.

The present invention also provides an emitting layer composition comprising the compound represented by Formula 1 as a phosphorescent host material, and provides an organic electronic element comprising the emitting layer.

Also, the present invention provides an electronic device comprising a display device including the organic electronic element; and a control unit for driving the display device; In another aspect, the organic electronic element is at least one of an organic electroluminescent device, an organic solar cell, an organic photoreceptor, an organic transistor, and a device for monochromatic or white lighting. At this time, the electronic device may be a current or future wired/wireless communication terminal, and covers all kinds of electronic devices including mobile communication terminals such as mobile phones, a personal digital assistant (PDA), an electronic dictionary, a point-to-multipoint (PMP), a remote controller, a navigation unit, a game player, various kinds of TVs, and various kinds of computers.

Hereinafter, a synthesis example of the compound represented by Formula 1 of the present invention and a manufacturing example of an organic electronic element of the present invention will be described in detail with reference to Examples, but the present invention is not limited to the following Examples.

Synthesis Example

The compound represented by Formula 1 according to the present invention (final products) is synthesized by reacting Sub 1 and Sub 2 as shown in Scheme 1 below, but is not limited thereto.

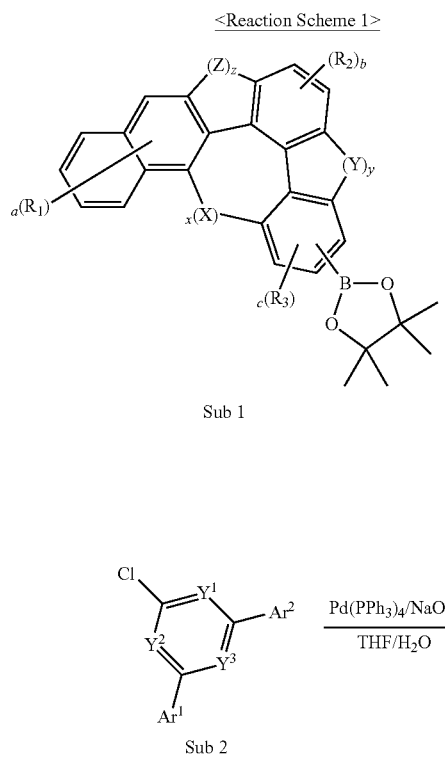

Sub 1

Sub 2

Final Products

I. Synthesis of Sub 1

Sub 1 of Reaction Scheme 1 may be synthesized by the reaction route of Reaction Scheme 2, but is not limited thereto.

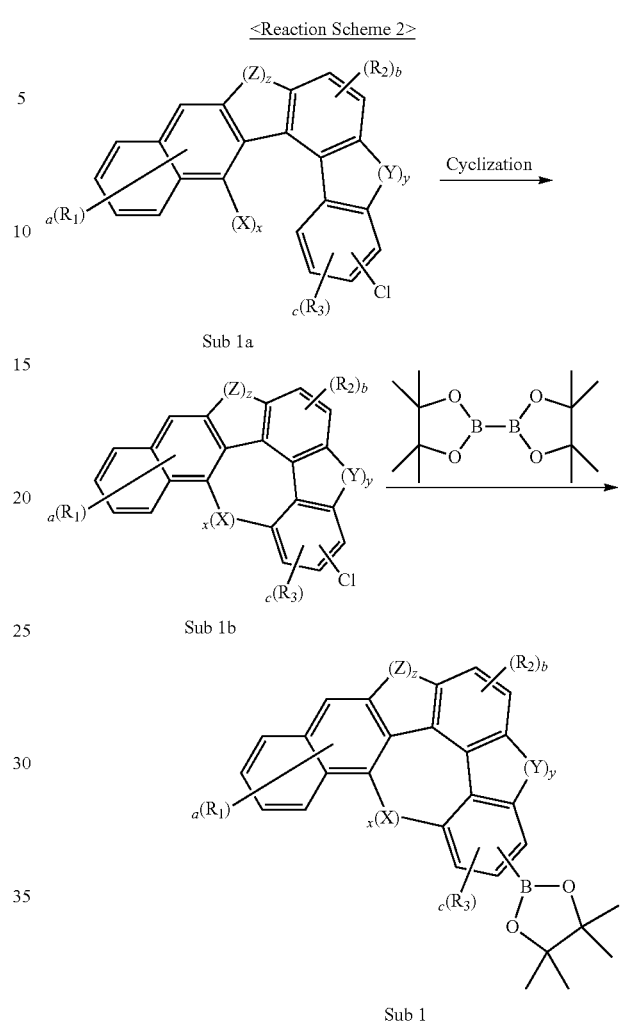

Synthesis examples of specific compounds belonging to Sub 1 are as follows.

1. Synthesis Example of Sub 1-4

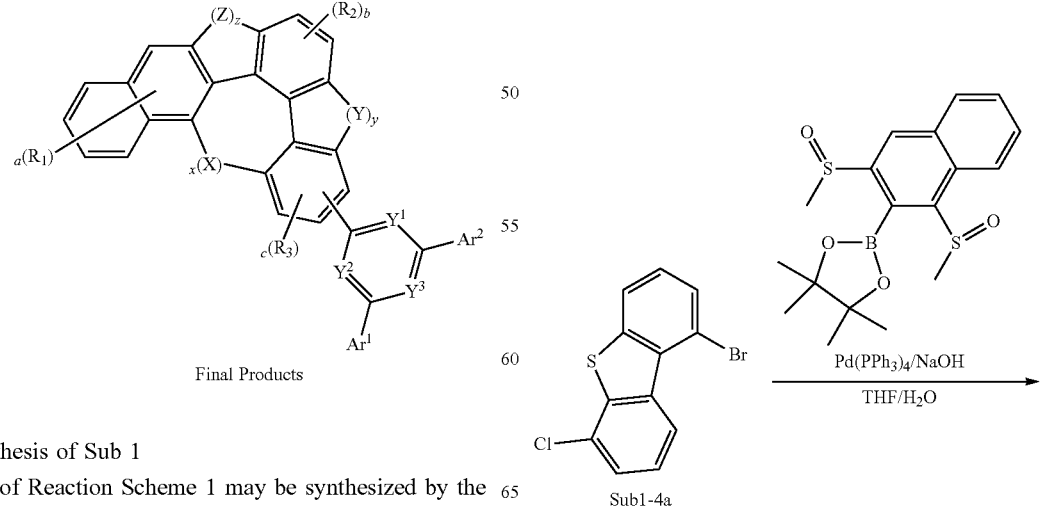

Sub1-4a

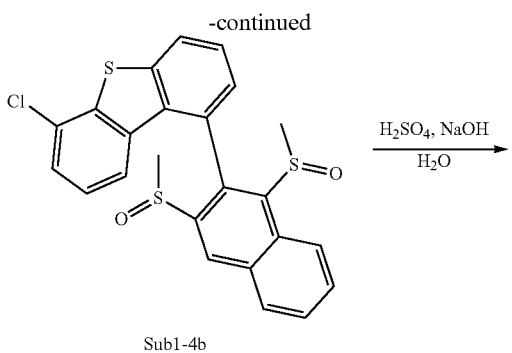

resulting organic material was separated by silicagel column and recrystallization to obtain 22 g (84.9%) of Sub1-4c.

(3) Synthesis of Sub 1-4

4,4,4',4',5,5,5',5'-octamethyl-2,2'-bi(1,3,2-dioxaborolane) (12.5 g, 0.05 mol), Pd$_2$(dba)$_3$ (1.3 g, 0.0015 mol), AcOK (14.2 g, 0.15 mol) and DMF (100 ml) were added to Sub1-4c (20 g, 0.05 mol) and stirred at 170° C. for 24 hours. Thereafter, the temperature is cooled to room temperature, and after washing with H$_2$O, H$_2$O is removed. The resulting organic material was separated by silicagel column and recrystallization to obtain 21.5 g (87.7%) of Sub1-4.

2. Synthesis Example of Sub 1-13

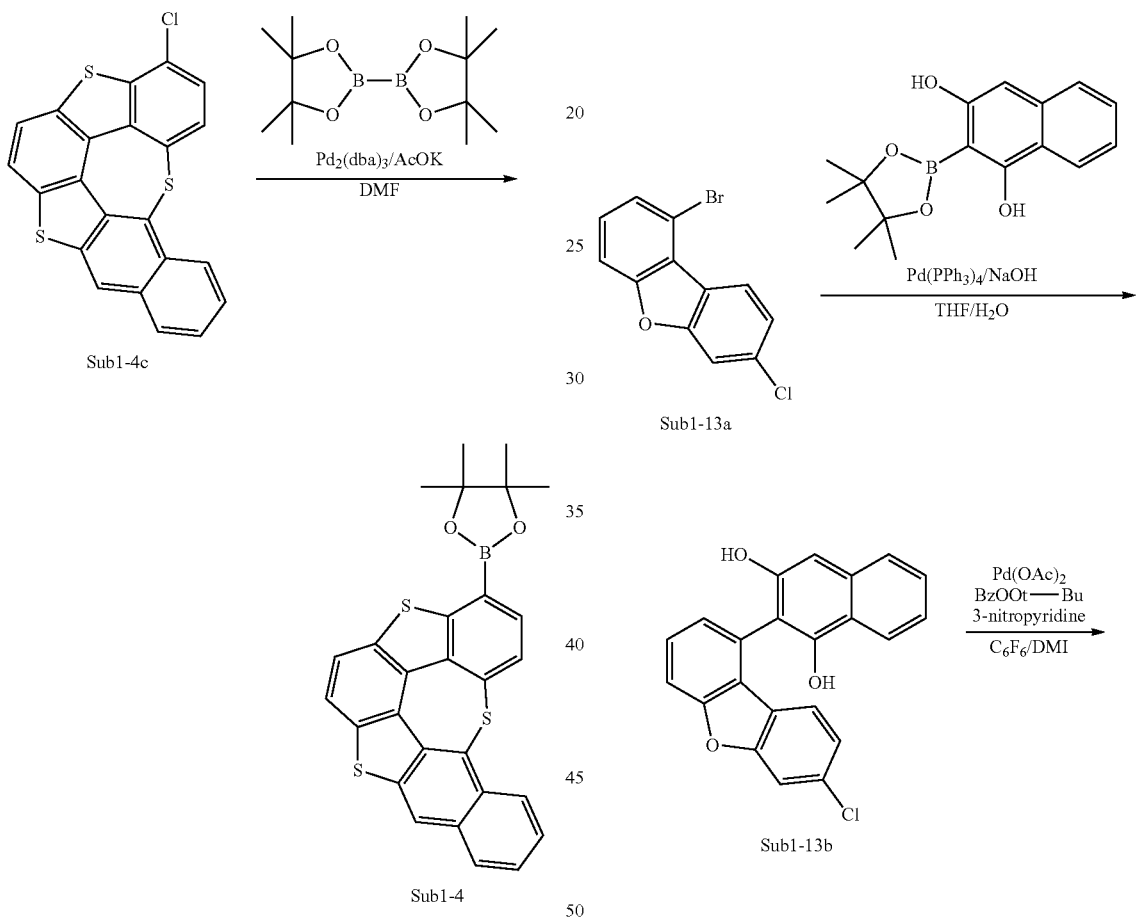

(1) Synthesis of Sub 1-4b

Sub1-4a (50 g, 0.17 mol), 2-(1,3-bis(methylsulfinyl)naphthalen-2-yl)-4,4,5,5-tetramethyl-1,3,2-dioxaborolane (63.6 g, 0.17 mol), Pd(PPh$_3$)$_4$ (5.8 g, 0.005 mol), NaOH (20.2 g, 0.50 mol), THF (336 mL) and water (100 mL) were added and reacted for 6 hours. After the reaction is completed, the temperature of the reactant is cooled to room temperature and the reaction solvent is removed. Then, the concentrated reactant was separated by silicagel column or recrystallization method to obtain 70 g (88.8%) of the product Sub1-4b.

(2) Synthesis of Sub 1-4c

Sub1-4b (30 g, 0.06 mol) was added to H$_2$SO$_4$ (45.7 g, 0.47 mol) and reacted for 6 hours. After the reaction was completed, it was neutralized in 2M NaOH aqueous solution. Thereafter, the temperature is cooled to room temperature, and after washing with H$_2$O, H$_2$O is removed. The

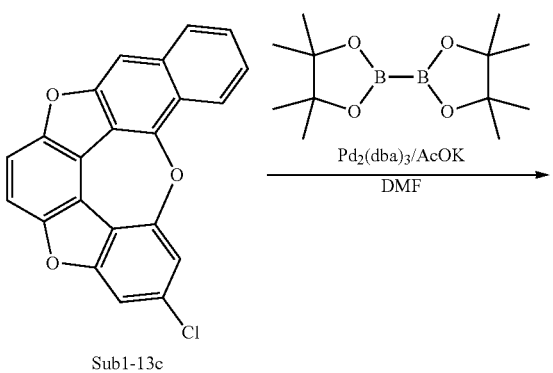

-continued

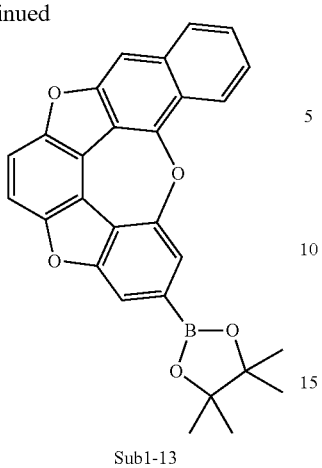
Sub1-13

(1) Synthesis of Sub 1-13b

Sub1-13a (30 g, 0.11 mol), 2-(4,4,5,5-tetramethyl-1,3,2-dioxaborolan-2-yl)naphthalene-1,3-diol (30.5 g, 0.11 mol), Pd(PPh$_3$)$_4$ (3.7 g, 0.003 mol), NaOH (12.8 g, 0.32 mol), THF (220 mL) and water (70 mL) were added and reacted for 6 hours. After the reaction was completed, 34 g (88.5%) of the product Sub1-13b was obtained by using the method for separating Sub1-4b described above.

(2) Synthesis of Sub 1-13c

Sub 1-13b (30 g, 0.08 mol) obtained in the above synthesis was added with Pd(OAc)$_2$ (0.6 g, 0.003 mol), 3-nitropyridine (0.31 g, 0.03 mol), and dissolved in C$_6$F$_6$ (140 ml) and DMI (166 ml), and thereafter tert-butyl peroxybenzoate (48.5 g, 0.25 mol) was added and stirred at 90° C. After the reaction was completed, 24 g (80.7%) of the product Sub1-13c was obtained by using the method for separating Sub1-4c described above.

(3) Synthesis of Sub 1-13

4,4,4',4',5,5,5',5'-octamethyl-2,2'-bi(1,3,2-dioxaborolane) (19.3 g, 0.07 mol), Pd$_2$(dba)$_3$ (1.9 g, 0.002 mol), AcOK (19.8 g, 0.20 mol), DMF (135 ml) were added to Sub1-13c (24 g, 0.07 mol) and stirred at 170° C. for 24 hours. When the reaction was completed, 26 g (86.1%) of the product Sub1-13 was obtained by using the separation method for Sub1-4 described above.

3. Synthesis Example of Sub 1-18

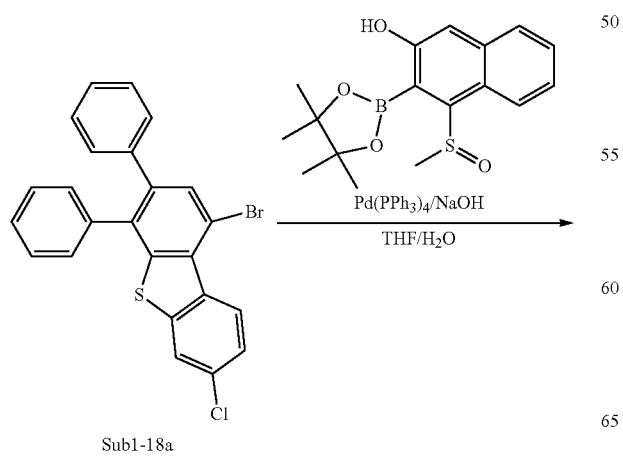
Sub1-18a

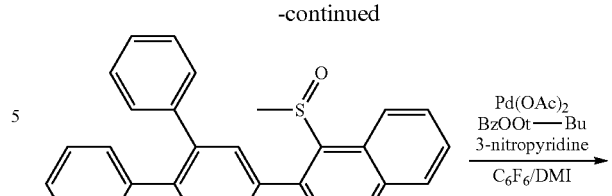
Sub1-18b

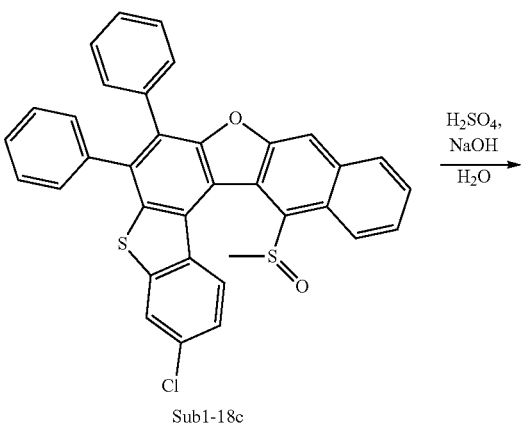
Sub1-18c

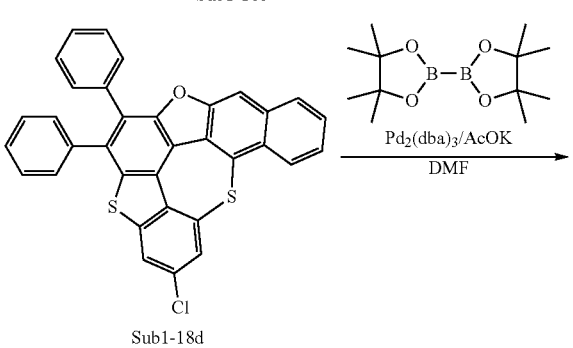
Sub1-18d

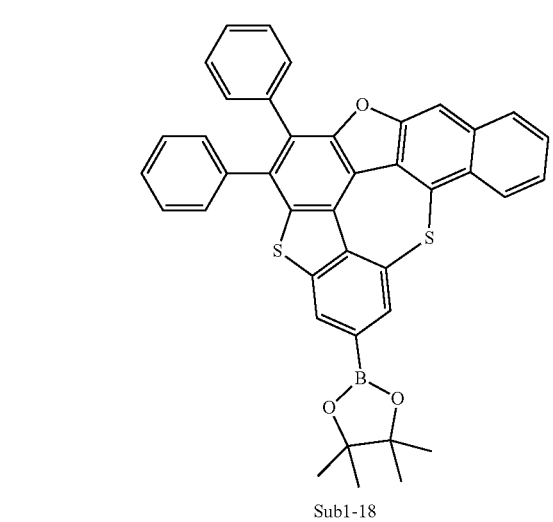 [SMILES: CC1(C)OB(c2cc3sc4c(-c5ccccc5)c(-c5ccccc5)c5oc6cc7ccccc7c7sc(c2)c3c4c5c67)OC1(C)C]
Sub1-18

(1) Synthesis of Sub 1-18b

Sub1-18a (50 g, 0.11 mol), 4-(methylsulfinyl)-3-(4,4,5,5-tetramethyl-1,3,2-dioxaborolan-2-yl)naphthalen-2-ol (37 g, 0.11 mol), Pd(PPh₃)₄ (3.9 g, 0.003 mol), NaOH (13.5 g, 0.33 mol), THF (220 mL) and water (70 mL) were added and reacted for 6 hours. After the reaction was completed, 52 g (81.2%) of the product Sub1-18b was obtained by using the method for separating Sub1-4b described above.

(2) Synthesis of Sub 1-18c

Sub 1-18b (30 g, 0.05 mol) obtained in the above synthesis was added with Pd(OAc)₂ (0.35 g, 0.002 mol), 3-nitropyridine (1.9 g, 0.02 mol), and dissolved in C₆F₆ (88 ml) and DMI (104 ml), and thereafter tert-butyl peroxybenzoate (30.4 g, 0.16 mol) was added and stirred at 90° C. After the reaction was completed, 24 g (80.3%) of the product Sub1-18c was obtained by using the method for separating Sub1-4c described above.

(3) Synthesis of Sub 1-18d

Sub1-18c (20 g, 0.03 mol) was added to H₂SO₄ (30 g, 0.30 mol) and reacted for 6 hours. After the reaction was completed, it was neutralized in 2M NaOH aqueous solution. Thereafter, the temperature is cooled to room temperature, and after washing with H₂O, H₂O is removed. The resulting organic material was separated by silicagel column and recrystallization to obtain 16 g (84.7%) of Sub1-18d.

(4) Synthesis of Sub 1-18

4,4,4',4',5,5,5',5'-octamethyl-2,2'-bi(1,3,2-dioxaborolane) (6.6 g, 0.03 mol), Pd₂(dba)₃ (0.7 g, 0.001 mol), AcOK (7.7 g, 0.08 mol), DMF (52 ml) were added to Sub1-18d (15 g, 0.03 mol) and stirred at 170° C. for 24 hours. When the reaction was completed, 13 g (78.6%) of the product Sub1-18 was obtained by using the separation method for Sub1-4 described above.

4. Synthesis Example of Sub 1-28

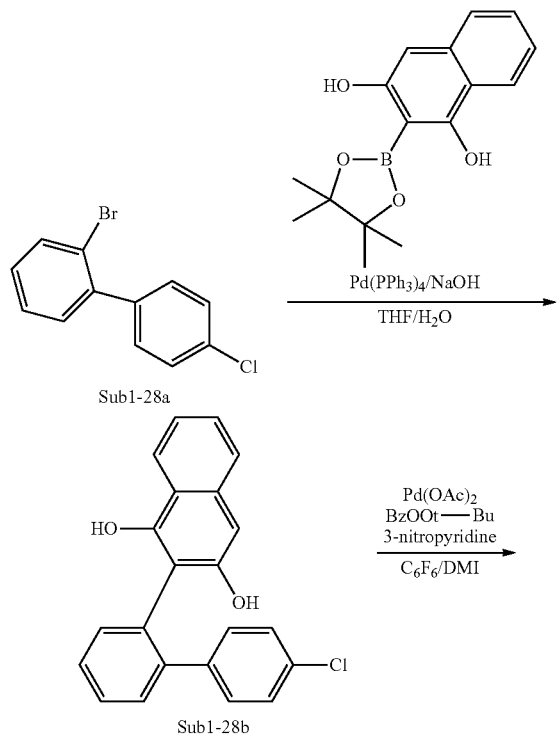

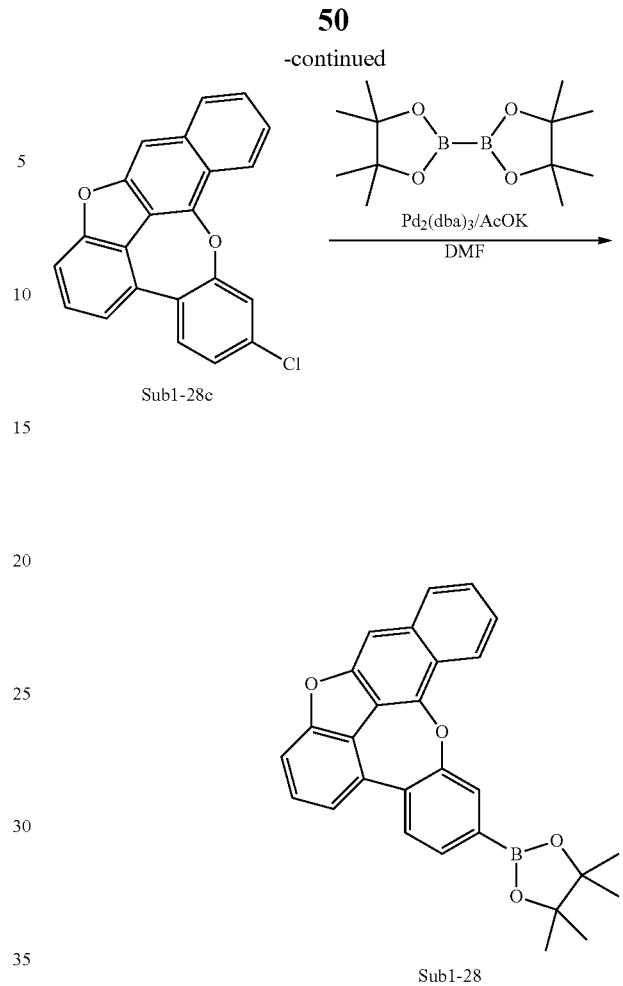

(1) Synthesis of Sub 1-28b

Sub1-28a (50 g, 0.19 mol), 2-(4,4,5,5-tetramethyl-1,3,2-dioxaborolan-2-yl)naphthalene-1,3-diol (53.6 g, 0.19 mol), Pd(PPh₃)₄ (6.5 g, 0.006 mol), NaOH (22.5 g, 0.56 mol), THF (380 mL) and water (120 mL) were added and reacted for 6 hours. After the reaction was completed, 52 g (80.3%) of the product Sub1-28b was obtained by using the method for separating Sub1-4b described above.

(2) Synthesis of Sub 1-28c

Sub 1-28b (50 g, 0.14 mol) obtained in the above synthesis was added with Pd(OAc)₂ (1 g, 0.004 mol), 3-nitropyridine (0.54 g, 0.04 mol), and dissolved in C₆F₆ (245 ml) and DMI (290 ml), and thereafter tert-butyl peroxybenzoate (81.2 g, 0.43 mol) was added and stirred at 90° C. After the reaction was completed, 39 g (78.9%) of the product Sub1-28c was obtained by using the method for separating Sub1-4c described above.

(3) Synthesis of Sub 1-28

4,4,4',4',5,5,5',5'-octamethyl-2,2'-bi(1,3,2-dioxaborolane) (26 g, 0.10 mol), Pd₂(dba)₃ (2.8 g, 0.003 mol), AcOK (30 g, 0.31 mol), DMF (205 ml) were added to Sub1-28c (35 g, 0.10 mol) and stirred at 170° C. for 24 hours. When the reaction was completed, 39 g (87.8%) of the product Sub1-28 was obtained by using the separation method for Sub1-28 described above.

5. Synthesis Example of Sub 1-42

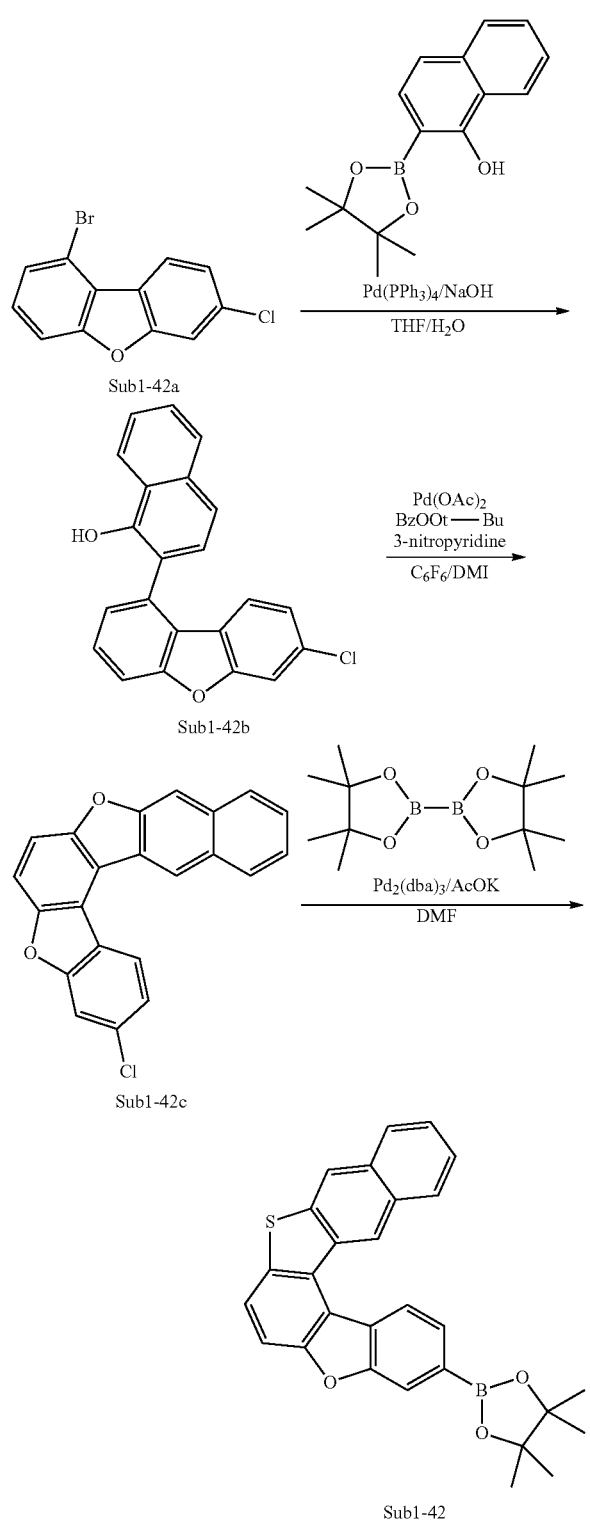

(1) Synthesis of Sub 1-42b

Sub1-42a (35 g, 0.12 mol), 2-(4,4,5,5-tetramethyl-1,3,2-dioxaborolan-2-yl)naphthalen-1-ol (33.6 g, 0.12 mol), Pd(PPh$_3$)$_4$ (4.3 g, 0.004 mol), NaOH (15 g, 0.37 mol), THF (250 mL), and water (80 mL) were added and reacted for 6 hours. After the reaction was completed, 38 g (88.7%) of the product Sub1-42b was obtained by using the method for separating Sub1-4b described above.

(2) Synthesis of Sub 1-42c

Sub 1-42b (30 g, 0.09 mol) obtained in the above synthesis was added with Pd(OAc)$_2$ (0.59 g, 0.003 mol), 3-nitropyridine (0.32 g, 0.03 mol), and dissolved in C$_6$F$_6$ (148 ml) and DMI (180 ml), and thereafter tert-butyl peroxybenzoate (50.8 g, 0.21 mol) was added and stirred at 90° C. After the reaction was completed, 26 g (87.2%) of the product Sub1-42c was obtained by using the method for separating Sub1-4c described above.

(3) Synthesis of Sub 1-42

4,4,4',4',5,5,5',5'-octamethyl-2,2'-bi(1,3,2-dioxaborolane) (18.6 g, 0.07 mol), Pd$_2$(dba)$_3$ (2 g, 0.002 mol), AcOK (21.5 g, 0.22 mol), DMF (146 ml) were added to Sub1-42c (25 g, 0.07 mol) and stirred at 170° C. for 24 hours. When the reaction was completed, 26 g (79%) of the product Sub1-42 was obtained by using the separation method for Sub1-4 described above.

6. Synthesis Example of Sub 1-53

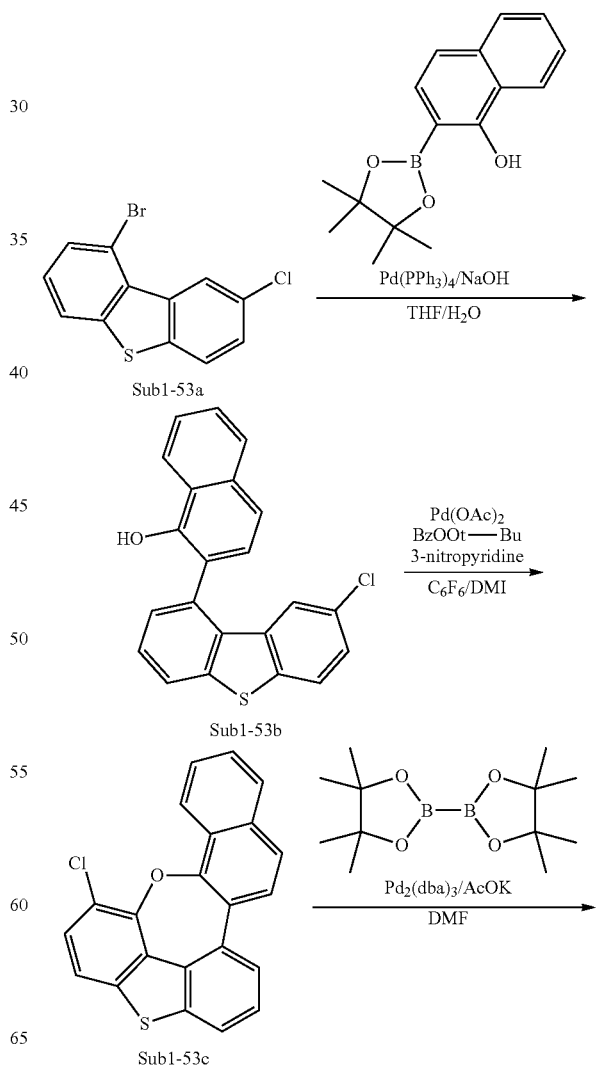

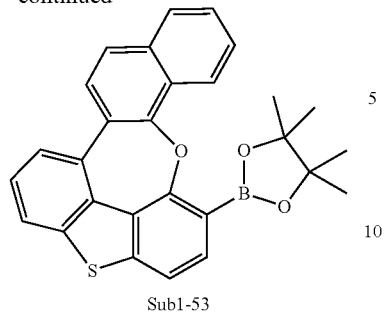

Sub1-53

(1) Synthesis of Sub 1-53b

Sub1-53a (50 g, 0.17 mol), 2-(4,4,5,5-tetramethyl-1,3,2-dioxaborolan-2-yl)naphthalen-1-ol (45.5 g, 0.17 mol), Pd(PPh$_3$)$_4$ (5.8 g, 0.005 mol), NaOH (20 g, 0.51 mol), THF (336 mL), and water (110 mL) were added and reacted for 6 hours. After the reaction was completed, 50 g (82.5%) of the product Sub1-53b was obtained by using the method for separating Sub1-4b described above.

(2) Synthesis of Sub 1-53c

Sub 1-53b (50 g, 0.14 mol) obtained in the above synthesis was added with Pd(OAc)$_2$ (1 g, 0.004 mol), 3-nitropyridine (0.52 g, 0.04 mol), and dissolved in C$_6$F$_6$ (236 ml) and DMI (280 ml), and thereafter tert-butyl peroxybenzoate (81 g, 0.42 mol) was added and stirred at 90° C. After the reaction was completed, 44 g (88.5%) of the product Sub1-53c was obtained by using the method for separating Sub1-4c described above.

(3) Synthesis of Sub 1-53

4,4,4',4',5,5,5',5'-octamethyl-2,2'-bi(1,3,2-dioxaborolane) (29.3 g, 0.12 mol), Pd$_2$(dba)$_3$ (3.4 g, 0.004 mol), AcOK (36 g, 0.37 mol), DMF (245 ml) were added to Sub1-53c (44 g, 0.12 mol) and stirred at 170° C. for 24 hours. When the reaction was completed, 45 g (81.4%) of the product Sub1-53 was obtained by using the separation method for Sub1-4 described above.

Meanwhile, the compound belonging to Sub 1 may be the following compounds, but is not limited thereto, and Table 1 below shows FD-MS (Field Desorption-Mass Spectrometry) values of the compounds belonging to Sub 1.

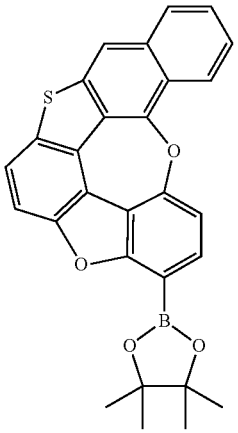

Sub1-2

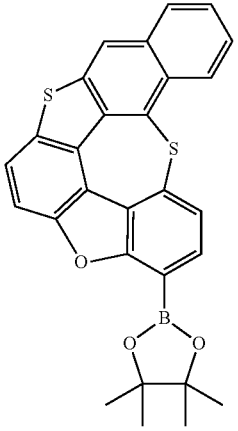

Sub1-3

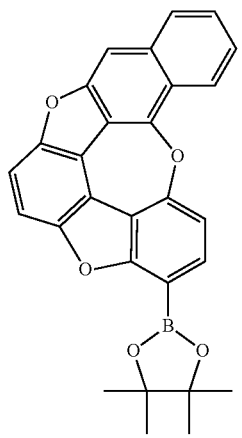

Sub1-1

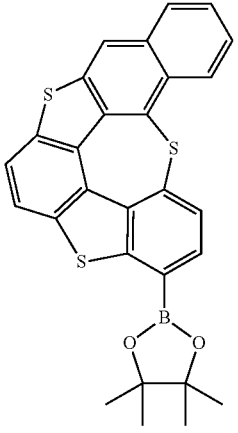

Sub1-4

Sub1-5
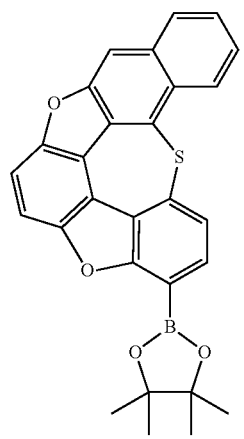
Sub1-8
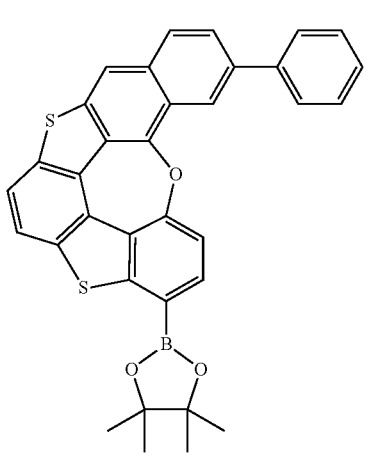
Sub1-6
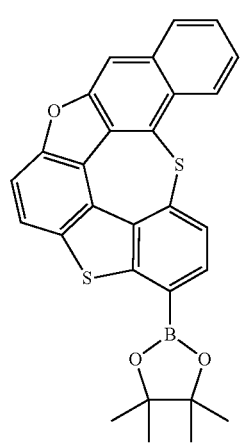
Sub1-9
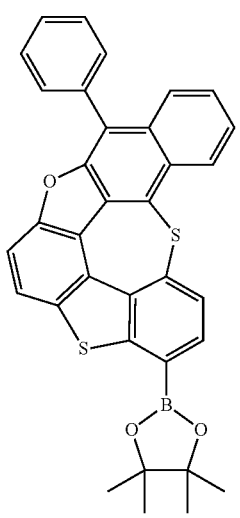
Sub1-7
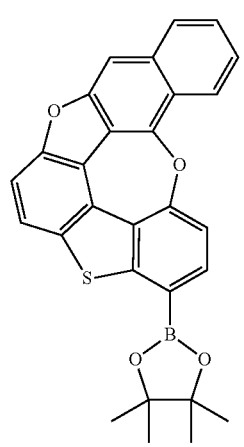
Sub1-10
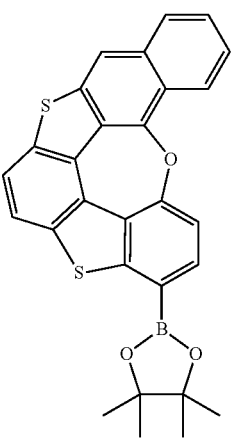

Sub1-11
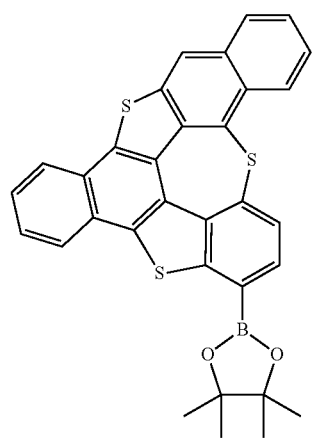
Sub1-12
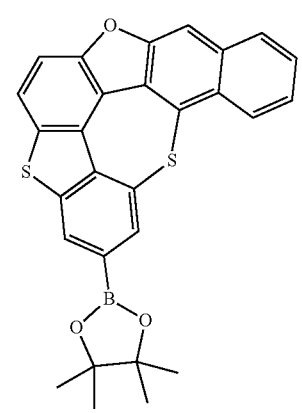
Sub1-13
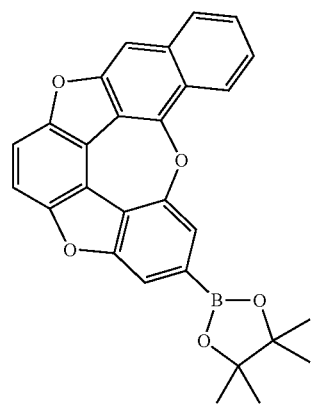
Sub1-14
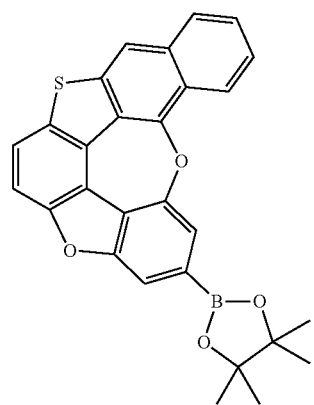
Sub1-15
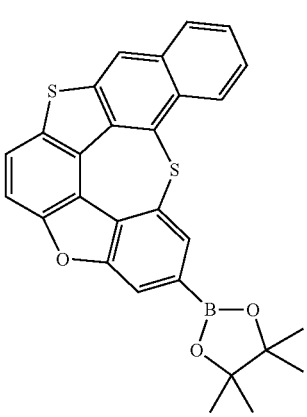
Sub1-16
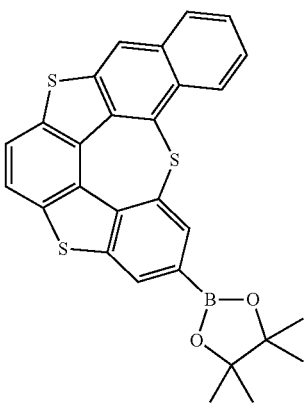
Sub1-17
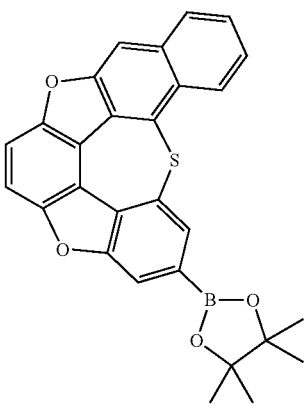

Sub1-18
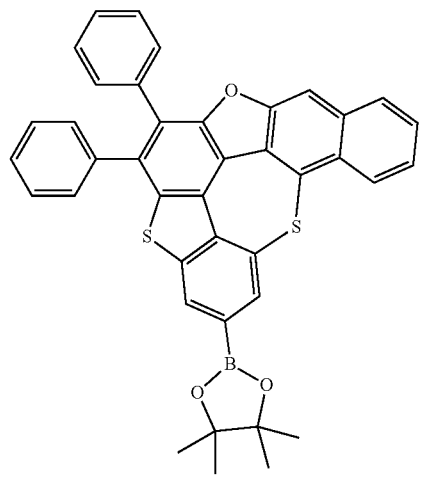
Sub1-21
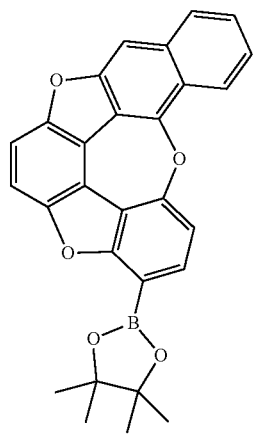
Sub1-19
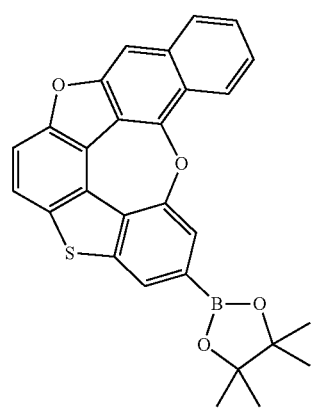
Sub1-22
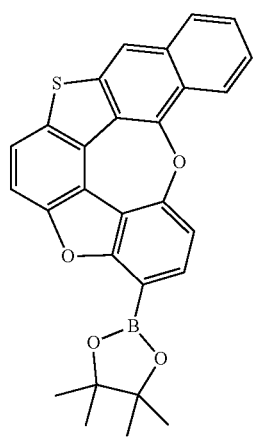
Sub1-20
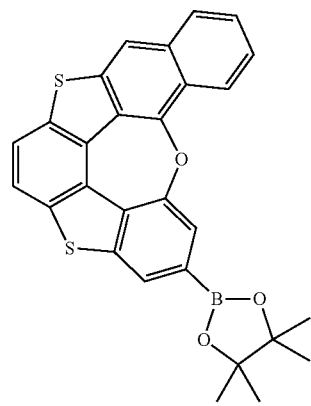
Sub1-23
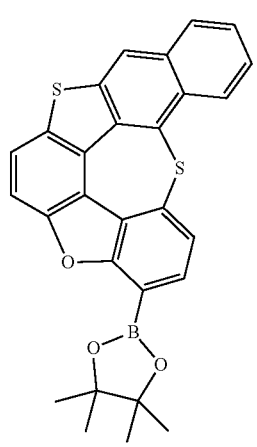

Sub1-24
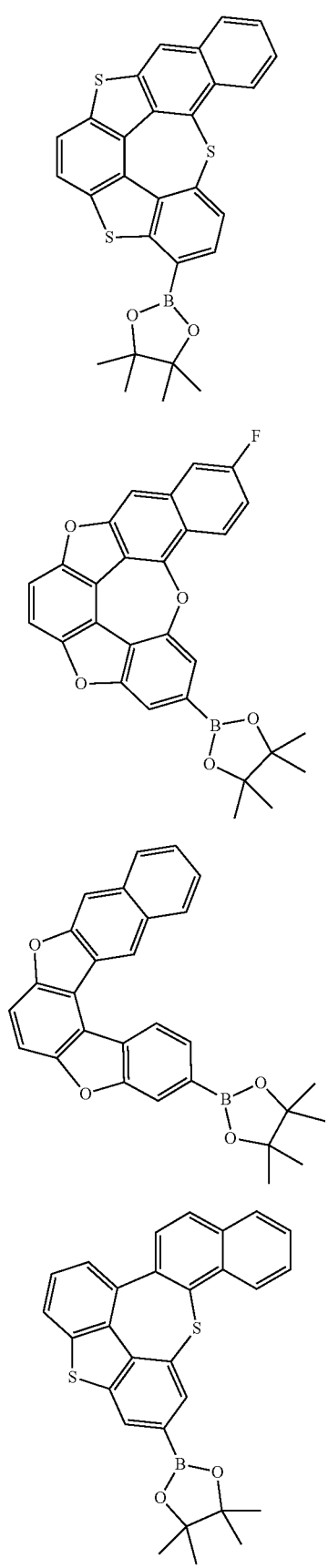
Sub1-25
Sub1-26
Sub1-27
Sub1-28
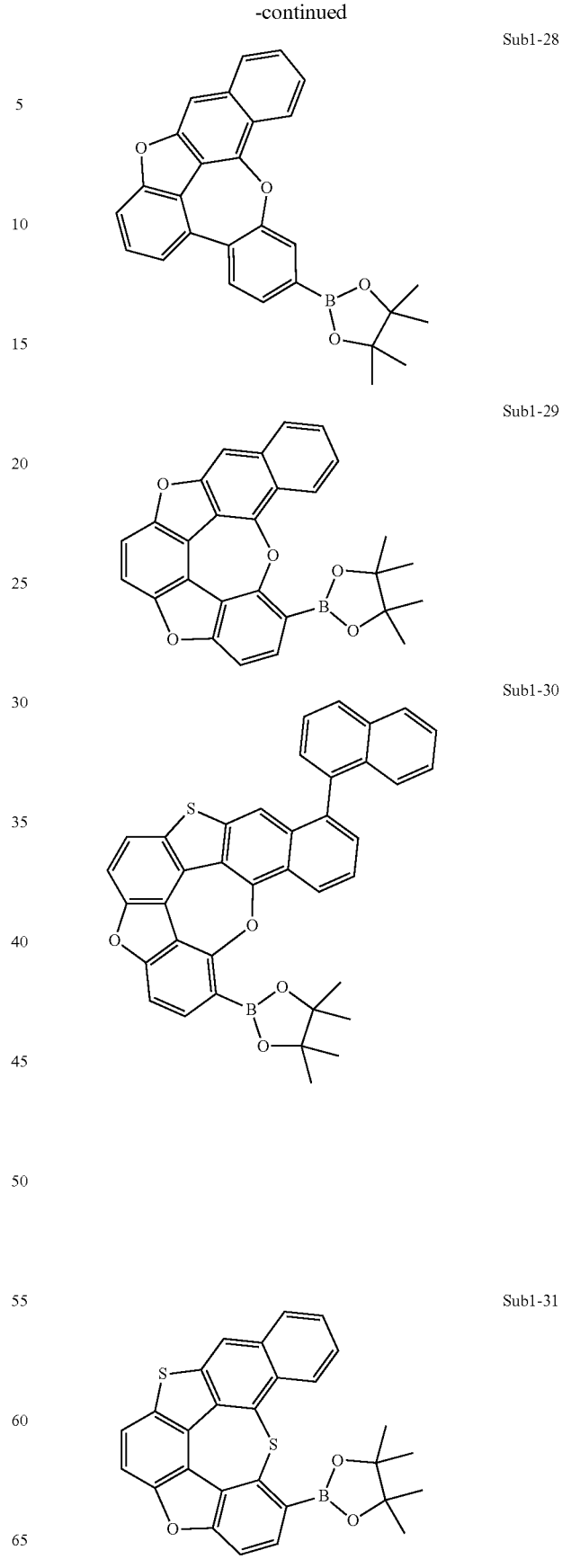
Sub1-29
Sub1-30
Sub1-31

-continued
Sub1-32
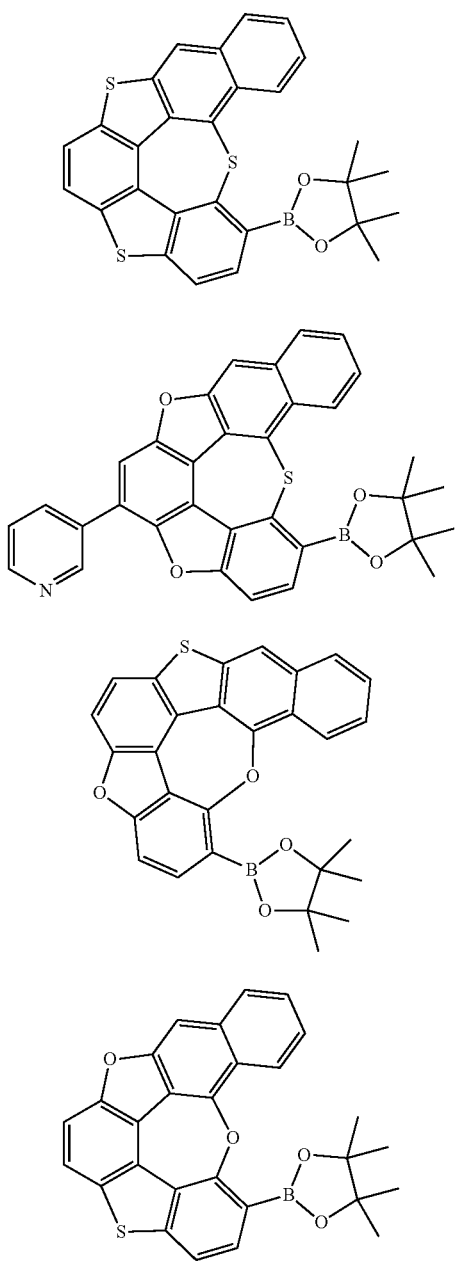
Sub1-33
Sub1-34
Sub1-35
Sub1-36
-continued
Sub1-37
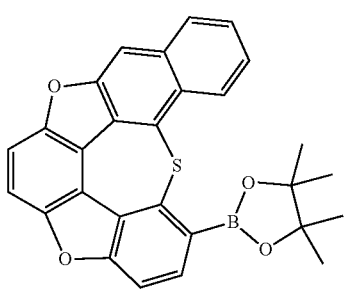
Sub1-38
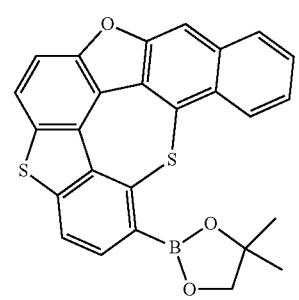
Sub1-39
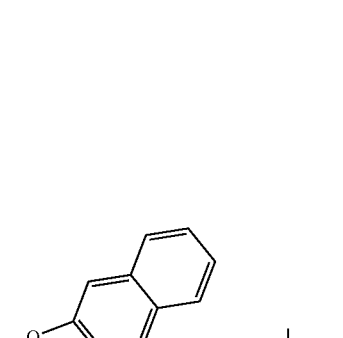
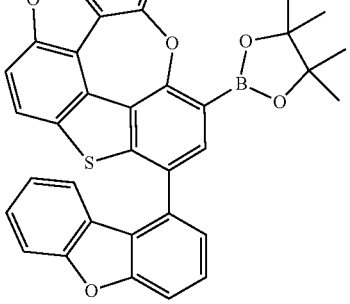
Sub1-40
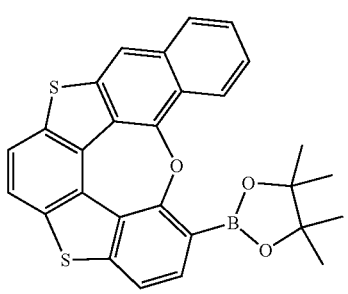

Sub-1-41
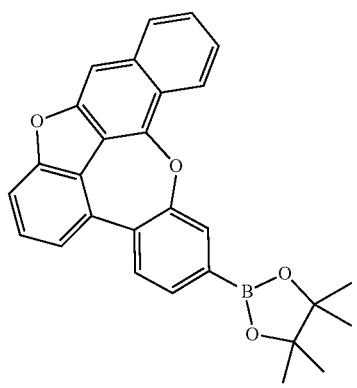
Sub1-42
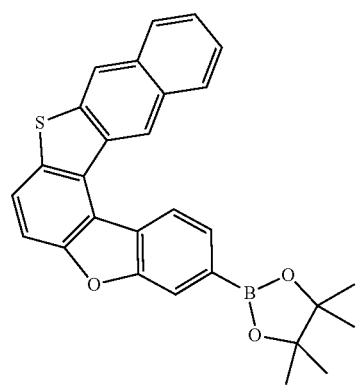
Sub1-43
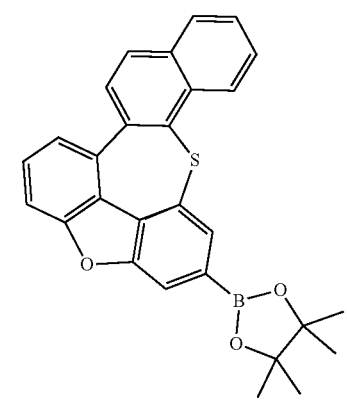
Sub1-44
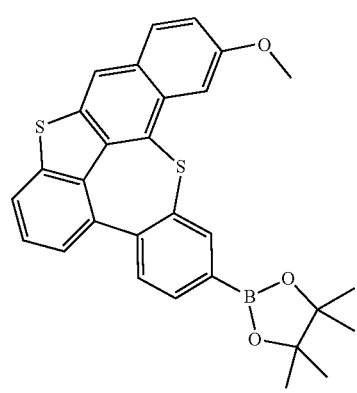
Sub1-45
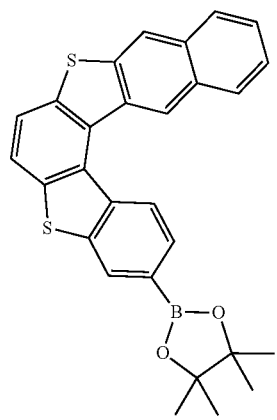
Sub1-46
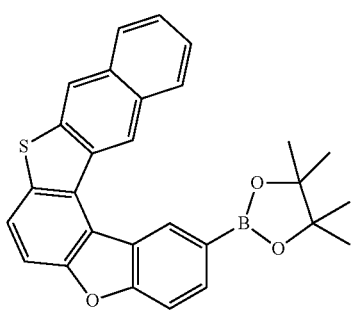
Sub1-47
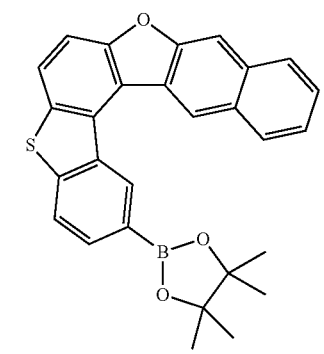
Sub1-48
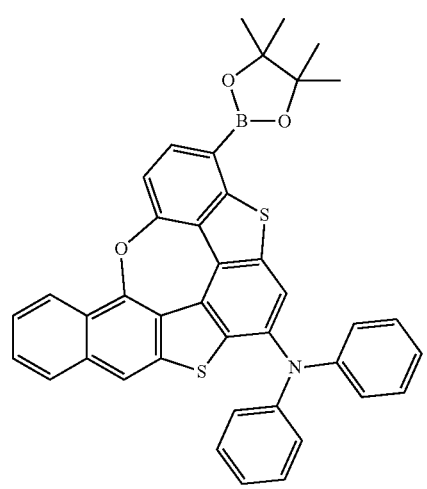

Sub1-49

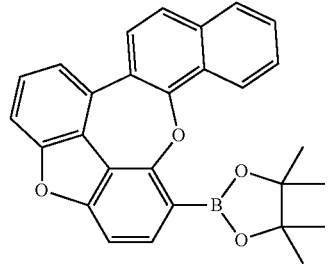

Sub1-50

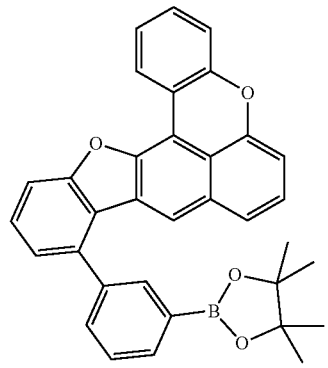

Sub1-51

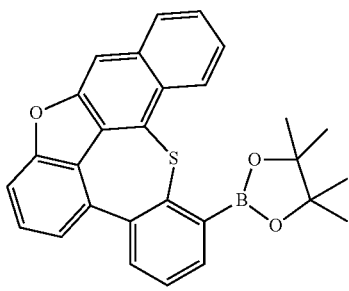

Sub1-52

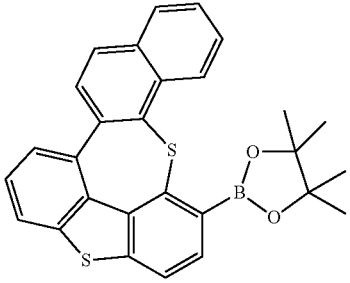

Sub1-53

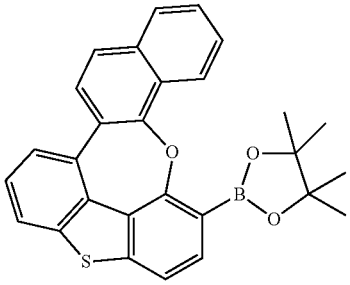

Sub1-54

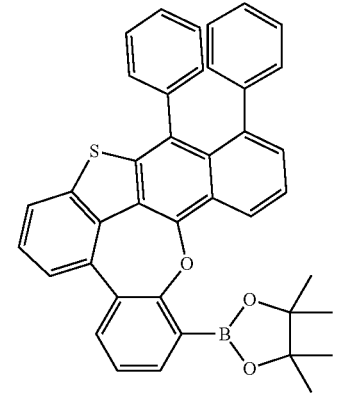

TABLE 1

| compound | FD-MS | compound | FD-MS |
| --- | --- | --- | --- |
| Sub1-1 | m/z = 448.15($C_{28}H_{21}BO_5$ = 448.28) | Sub1-2 | m/z = 464.13($C_{28}H_{21}BO_4S$ = 464.34) |
| Sub1-3 | m/z = 480.1($C_{28}H_{21}BO_3S_2$ = 480.4) | Sub1-4 | m/z = 496.08($C_{28}H_{21}BO_2S_3$ = 496.46) |
| Sub1-5 | m/z = 464.13($C_{28}H_{21}BO_4S$ = 464.34) | Sub1-6 | m/z = 480.1($C_{28}H_{21}BO_3S_2$ = 480.4) |
| Sub1-7 | m/z = 464.13($C_{28}H_{21}BO_4S$ = 464.34) | Sub1-8 | m/z = 556.13($C_{34}H_{25}BO_3S_2$ = 556.5) |
| Sub1-9 | m/z = 556.13($C_{34}H_{25}BO_3S_2$ = 556.5) | Sub1-10 | m/z = 480.1($C_{28}H_{21}BO_3S_2$ = 480.4) |
| Sub1-11 | m/z = 546.1($C_{32}H_{23}BO_2S_3$ = 546.52) | Sub1-12 | m/z = 480.1($C_{28}H_{21}BO_3S_2$ = 480.4) |
| Sub1-13 | m/z = 448.15($C_{28}H_{21}BO_5$ = 448.28) | Sub1-14 | m/z = 464.13($C_{28}H_{21}BO_4S$ = 464.34) |
| Sub1-15 | m/z = 480.1($C_{28}H_{21}BO_3S_2$ = 480.4) | Sub1-16 | m/z = 496.08($C_{28}H_{21}BO_2S_3$ = 496.46) |
| Sub1-17 | m/z = 464.13($C_{28}H_{21}BO_4S$ = 464.34) | Sub1-18 | m/z = 632.17($C_{40}H_{29}BO_3S_2$ = 632.6) |
| Sub1-19 | m/z = 464.13($C_{28}H_{21}BO_4S$ = 464.34) | Sub1-20 | m/z = 480.1($C_{28}H_{21}BO_3S_2$ = 480.4) |
| Sub1-21 | m/z = 448.15($C_{28}H_{21}BO_5$ = 448.28) | Sub1-22 | m/z = 464.13($C_{28}H_{21}BO_4S$ = 464.34) |
| Sub1-23 | m/z = 480.1($C_{28}H_{21}BO_3S_2$ = 480.4) | Sub1-24 | m/z = 496.08($C_{28}H_{21}BO_2S_3$ = 496.46) |
| Sub1-25 | m/z = 466.14($C_{28}H_{20}BFO_5$ = 466.27) | Sub1-26 | m/z = 434.17($C_{28}H_{23}BO_4$ = 434.3) |
| Sub1-27 | m/z = 466.12($C_{28}H_{23}BO_2S_2$ = 466.42) | Sub1-28 | m/z = 434.17($C_{28}H_{23}BO_4$ = 434.3) |
| Sub1-29 | m/z = 448.15($C_{28}H_{21}BO_5$ = 448.28) | Sub1-30 | m/z = 590.17($C_{38}H_{27}BO_4S$ = 590.5) |
| Sub1-31 | m/z = 480.1($C_{28}H_{21}BO_3S_2$ = 480.4) | Sub1-32 | m/z = 496.08($C_{28}H_{21}BO_2S_3$ = 496.46) |
| Sub1-33 | m/z = 541.15($C_{33}H_{24}BNO_4S$ = 541.43) | Sub1-34 | m/z = 464.13($C_{28}H_{21}BO_4S$ = 464.34) |
| Sub1-35 | m/z = 464.13($C_{28}H_{21}BO_4S$ = 464.34) | Sub1-36 | m/z = 480.1($C_{28}H_{21}BO_3S_2$ = 480.4) |
| Sub1-37 | m/z = 464.13($C_{28}H_{21}BO_4S$ = 464.34) | Sub1-38 | m/z = 480.1($C_{28}H_{21}BO_3S_2$ = 480.4) |
| Sub1-39 | m/z = 630.17($C_{40}H_{27}BO_5S$ = 630.52) | Sub1-40 | m/z = 480.1($C_{28}H_{21}BO_3S_2$ = 480.4) |
| Sub1-41 | m/z = 434.17($C_{28}H_{23}BO_4$ = 434.3) | Sub1-42 | m/z = 450.15($C_{28}H_{23}BO_3S$ = 450.36) |
| Sub1-43 | m/z = 450.15($C_{28}H_{23}BO_3S$ = 450.36) | Sub1-44 | m/z = 496.13($C_{29}H_{25}BO_3S_2$ = 496.45) |
| Sub1-45 | m/z = 466.12($C_{28}H_{23}BO_2S_2$ = 466.42) | Sub1-46 | m/z = 450.15($C_{28}H_{23}BO_3S$ = 450.36) |
| Sub1-47 | m/z = 450.15($C_{28}H_{23}BO_3S$ = 450.36) | Sub1-48 | m/z = 647.18($C_{40}H_{30}BNO_3S_2$ = 647.61) |
| Sub1-49 | m/z = 434.17($C_{28}H_{23}BO_4$ = 434.3) | Sub1-50 | m/z = 510.2($C_{34}H_{27}BO_4$ = 510.4) |

TABLE 1-continued
| compound | FD-MS | compound | FD-MS |
|---|---|---|---|
| Sub1-51 | m/z = 450.15($C_{28}H_{23}BO_3S$ = 450.36) | Sub1-52 | m/z = 466.12($C_{28}H_{23}BO_2S_2$ = 466.42) |
| Sub1-53 | m/z = 450.15($C_{28}H_{23}BO_3S$ = 450.36) | Sub1-54 | m/z = 602.21($C_{40}H_{31}BO_3S$ = 602.56) |
Meanwhile, the compound belonging to Sub 2 may be a compound as follows, but is not limited thereto, and Table 2 below shows Field Desorption-Mass Spectrometry (FD-MS) values of the compound belonging to Sub 2.
Sub2-1
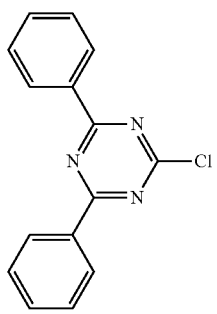
Sub2-2
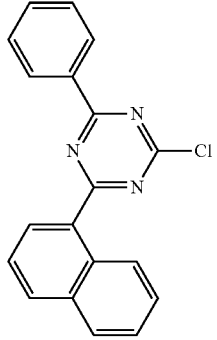
Sub2-3
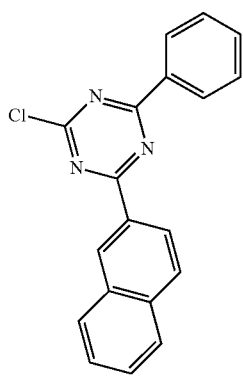
Sub2-4
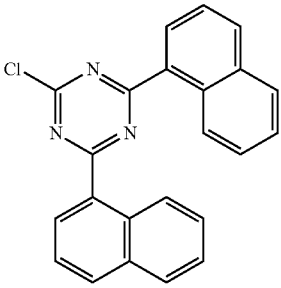
Sub2-5
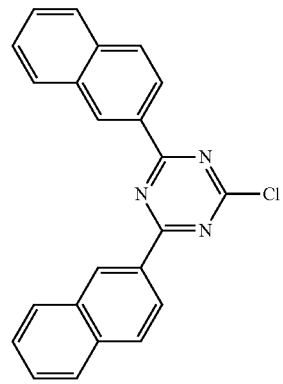
Sub2-6
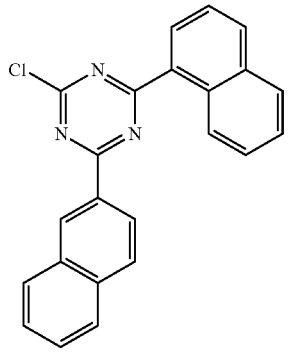
Sub2-7
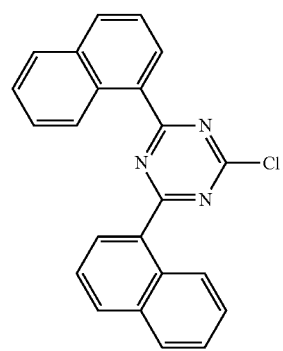

Sub2-8 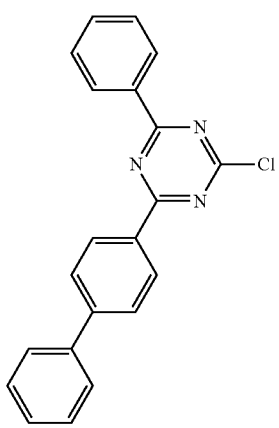
Sub2-9 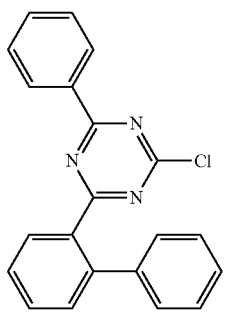
Sub2-10 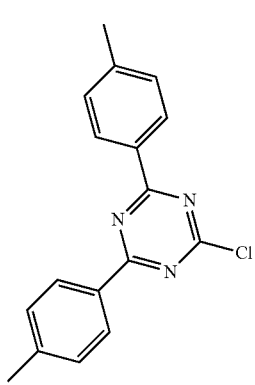
Sub2-11 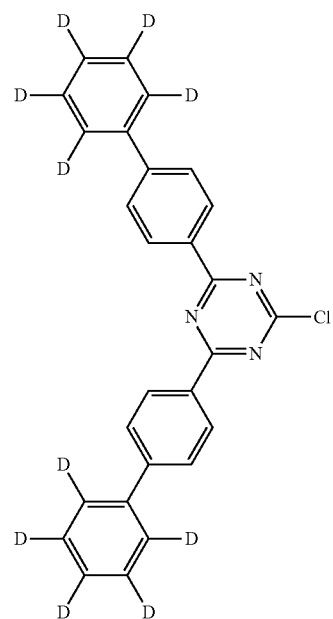
Sub2-12 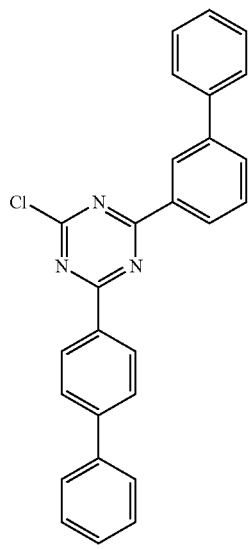

Sub2-13
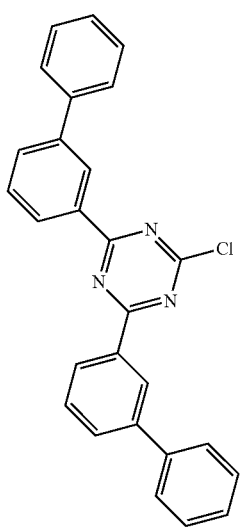
Sub2-14
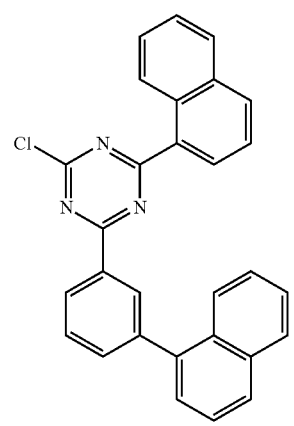
Sub2-15
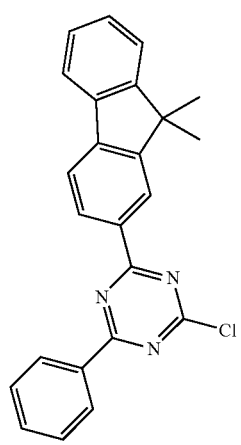
Sub2-16
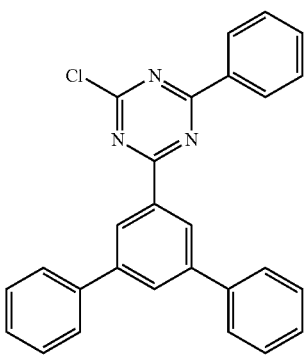
Sub2-17
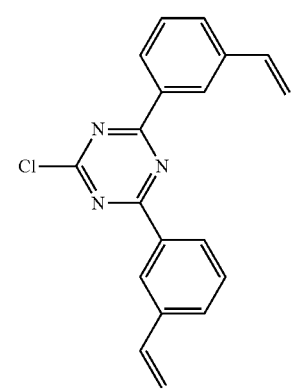
Sub2-18
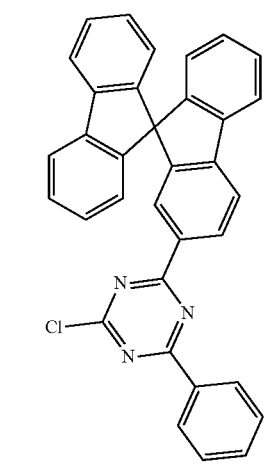
Sub2-19
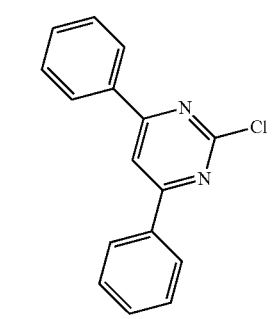

Sub2-20
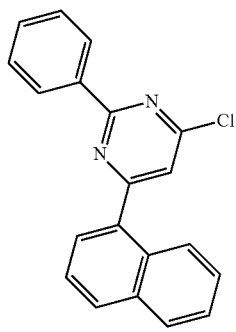
Sub2-21
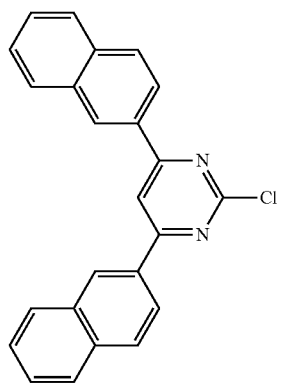
Sub2-22
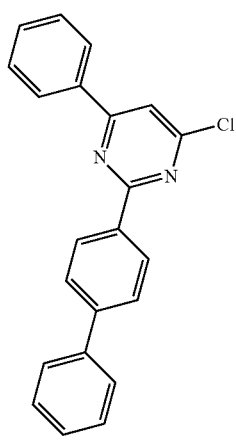
Sub2-23
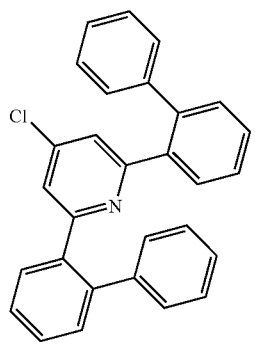
Sub2-24
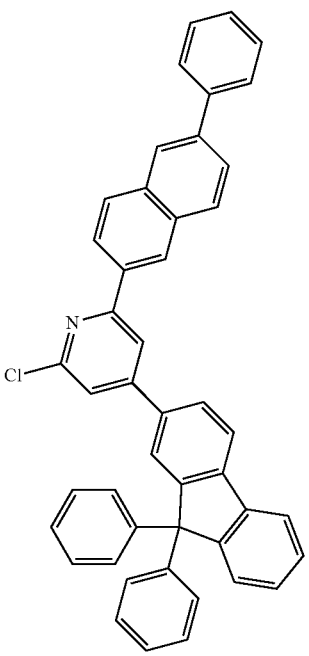
Sub2-25
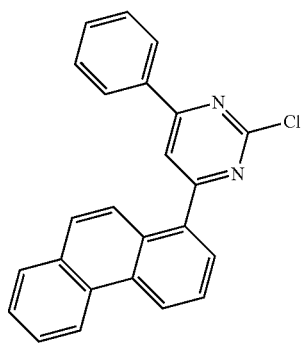
Sub2-26
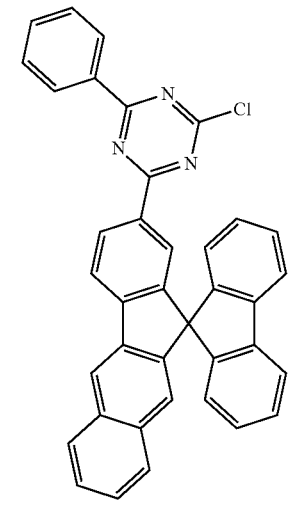

Sub2-27
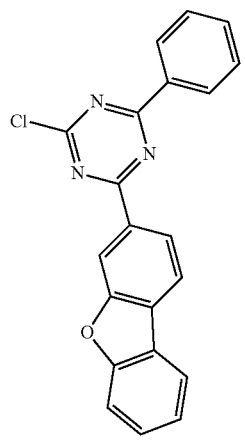
Sub2-28
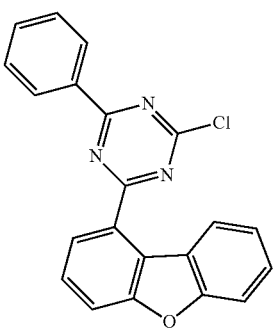
Sub2-29
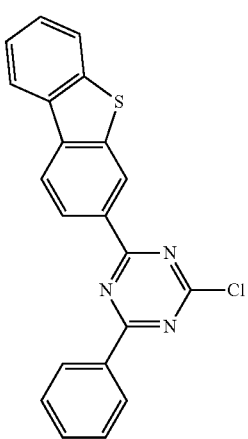
Sub2-30
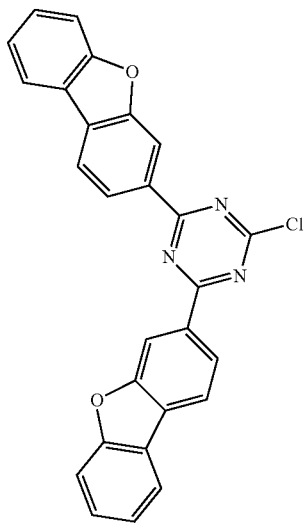
Sub2-31
Sub2-32
Sub2-33
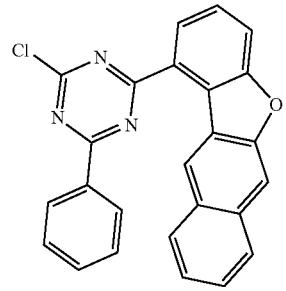

Sub2-34
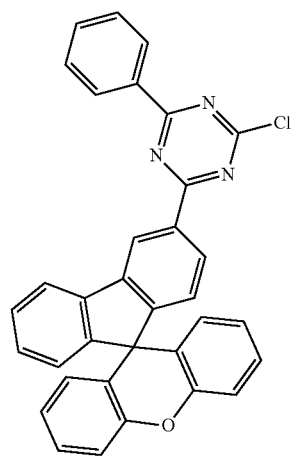
Sub2-35
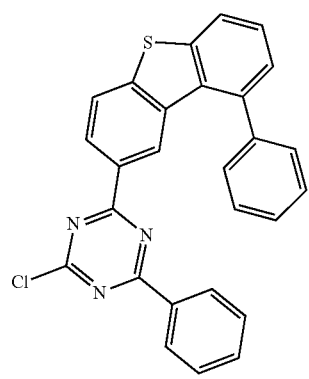
Sub2-36
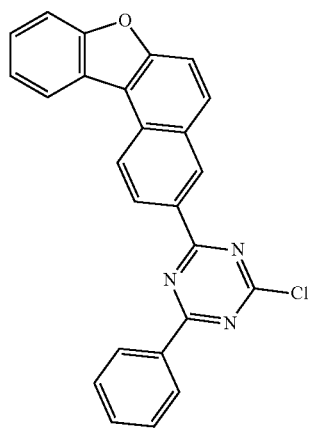
Sub2-37
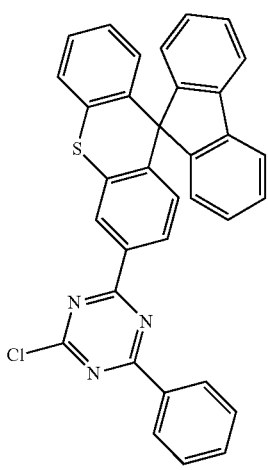
Sub2-38
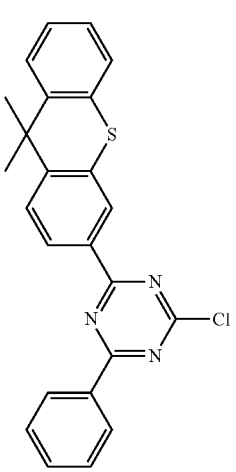
Sub2-39
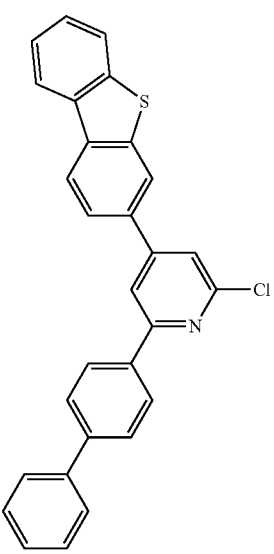

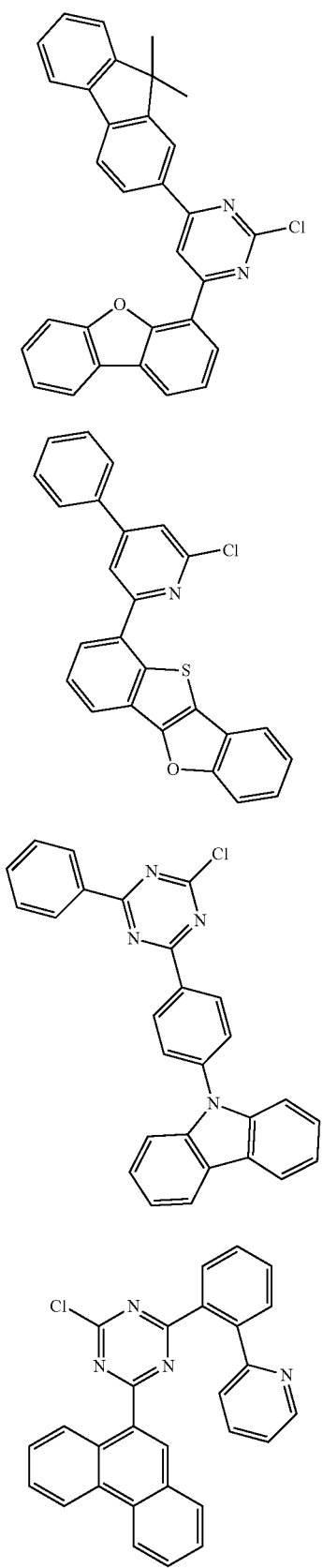
Sub2-40
Sub2-41
Sub2-42
Sub2-43
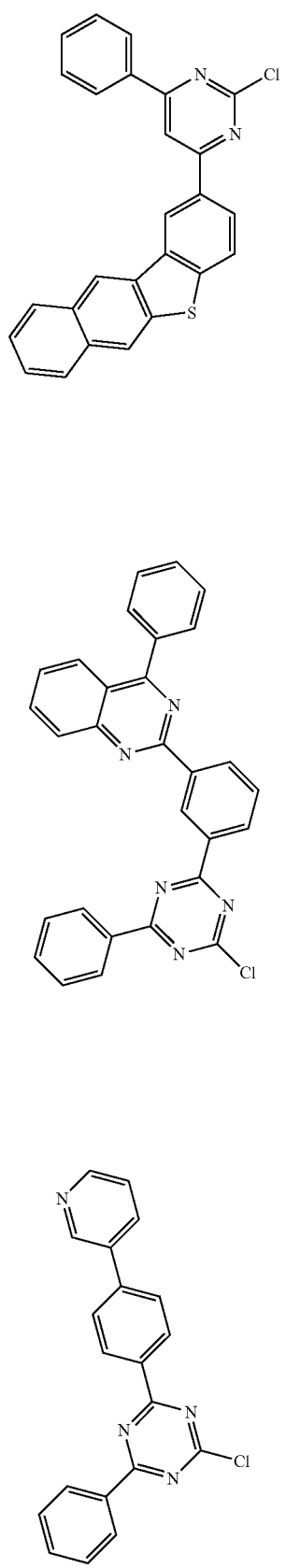
Sub2-44
Sub2-45
Sub2-46

Sub2-47
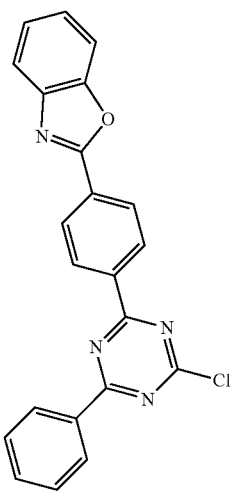
Sub2-48
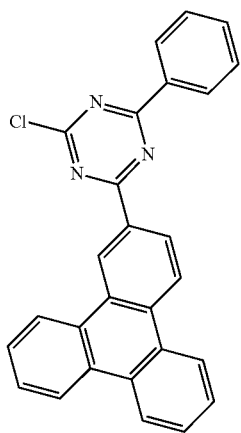
Sub2-49
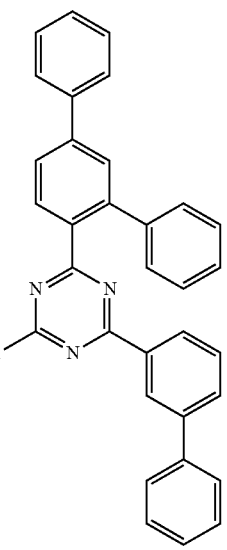
Sub2-50
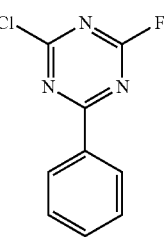
Sub2-51
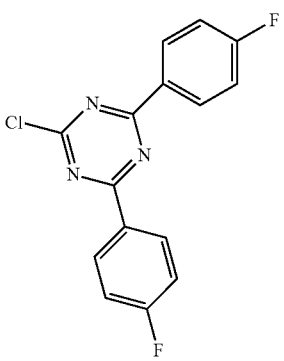
Sub2-52
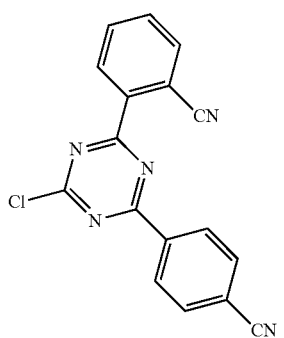
Sub2-53

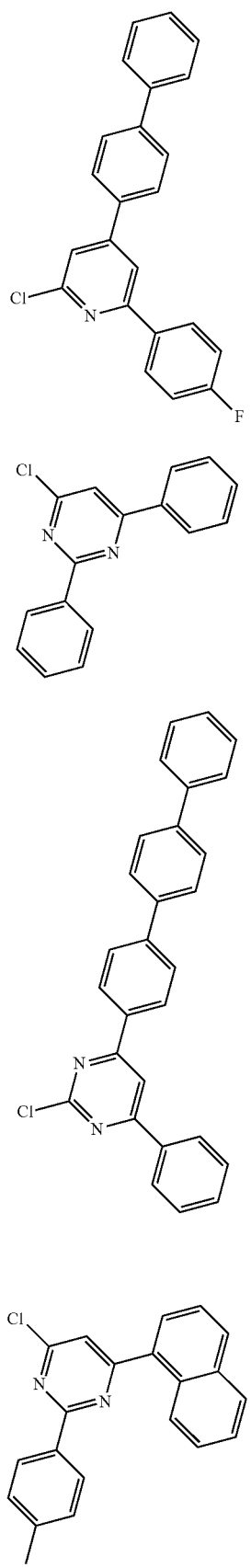
Sub2-54
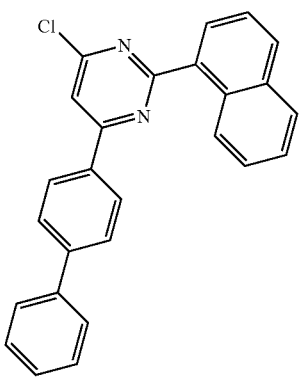
Sub2-58
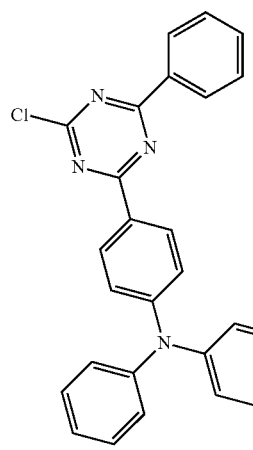
Sub2-59
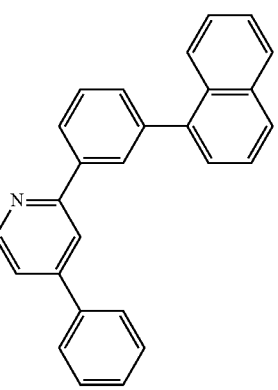
Sub2-60
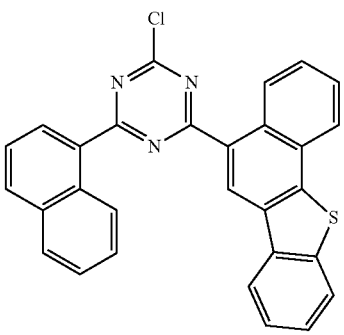
Sub2-61

Sub2-62

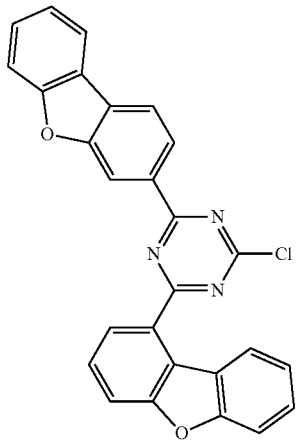

Sub2-63

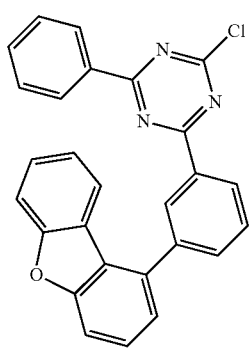

Sub2-64

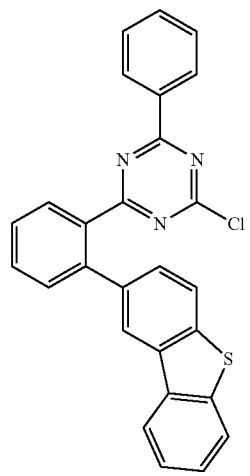

Sub2-65

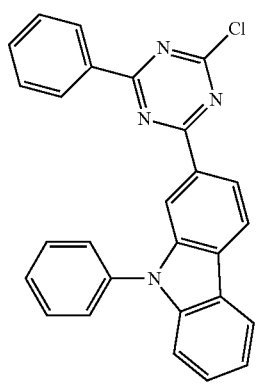

Sub2-66

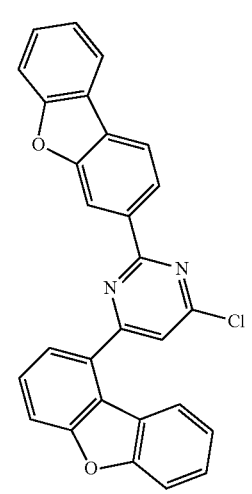

TABLE 2

| compound | FD-MS | compound | FD-MS |
|---|---|---|---|
| Sub2-1 | m/z = 267.06(C15H10ClN3 = 267.72) | Sub2-2 | m/z = 317.07(C19H12ClN3 = 317.78) |
| Sub2-3 | m/z = 317.07(C19H12ClN3 = 317.78) | Sub2-4 | m/z = 367.09(C23H14ClN3 = 367.84) |
| Sub2-5 | m/z = 367.09(C23H14ClN3 = 367.84) | Sub2-6 | m/z = 367.09(C23H14ClN3 = 367.84) |
| Sub2-7 | m/z = 367.09(C23H14ClN3 = 367.84) | Sub2-8 | m/z = 343.09(C21H14ClN3 = 343.81) |
| Sub2-9 | m/z = 343.09(C21H14ClN3 = 343.81) | Sub2-10 | m/z = 295.09(C17H14ClN3 = 295.77) |
| Sub2-11 | m/z = 429.18(C27H8D10ClN3 = 429.97) | Sub2-12 | m/z = 419.12(C27H18ClN3 = 419.91) |
| Sub2-13 | m/z = 419.12(C27H18ClN3 = 419.91) | Sub2-14 | m/z = 443.12(C29H18ClN3 = 443.93) |
| Sub2-15 | m/z = 383.12(C24H18ClN3 = 383.88) | Sub2-16 | m/z = 419.12(C27H18ClN3 = 419.91) |
| Sub2-17 | m/z = 319.09(C19H14ClN3 = 319.79) | Sub2-18 | m/z = 505.13(C34H20ClN3 = 506.01) |
| Sub2-19 | m/z = 266.06(C16H11ClN2 = 266.73) | Sub2-20 | m/z = 316.08(C20H13ClN2 = 316.79) |
| Sub2-21 | m/z = 366.09(C24H15ClN2 = 366.85) | Sub2-22 | m/z = 342.09(C22H15ClN2 = 342.83) |
| Sub2-23 | m/z = 417.13(C29H20ClN = 417.94) | Sub2-24 | m/z = 631.21(C46H30ClN = 632.2) |

TABLE 2-continued

| compound | FD-MS | compound | FD-MS |
| --- | --- | --- | --- |
| Sub2-25 | m/z = 366.09(C24H15ClN2 = 366.85) | Sub2-26 | m/z = 555.15(C38H22ClN3 = 556.07) |
| Sub2-27 | m/z = 357.07(C21H12ClN3O = 357.8) | Sub2-28 | m/z = 357.07(C21H12ClN3O = 357.8) |
| Sub2-29 | m/z = 373.04(C21H12ClN3S = 373.86) | Sub2-30 | m/z = 447.08(C27H14ClN3O2 = 447.88) |
| Sub2-31 | m/z = 407.08(C25H14ClN3O = 407.86) | Sub2-32 | m/z = 373.06(C21H12ClN3O2 = 373.8) |
| Sub2-33 | m/z = 407.08(C25H14ClN3O = 407.86) | Sub2-34 | m/z = 521.13(C34H20ClN3O = 522) |
| Sub2-35 | m/z = 449.08(C27H16ClN3S = 449.96) | Sub2-36 | m/z = 407.08(C25H14ClN3O = 407.86) |
| Sub2-37 | m/z = 537.11(C34H20ClN3S = 538.07) | Sub2-38 | m/z = 415.09(C24H18ClN3S = 415.94) |
| Sub2-39 | m/z = 447.08(C29H18ClNS = 447.98) | Sub2-40 | m/z = 472.13(C31H21ClN2O = 472.97) |
| Sub2-41 | m/z = 411.05(C25H14ClNOS = 411.9) | Sub2-42 | m/z = 432.11(C27H17ClN4 = 432.91) |
| Sub2-43 | m/z = 444.11(C28H17ClN4 = 444.92) | Sub2-44 | m/z = 422.06(C26H15ClN2S = 422.93) |
| Sub2-45 | m/z = 471.13(C29H18ClN5 = 471.95) | Sub2-46 | m/z = 344.08(C20H13ClN4 = 344.8) |
| Sub2-47 | m/z = 384.08(C22H13ClN4O = 384.82) | Sub2-48 | m/z = 448.08(C28H17ClN2S = 448.97) |
| Sub2-49 | m/z = 417.1(C27H16ClN3 = 417.9) | Sub2-50 | m/z = 495.15(C33H22ClN3 = 496.01) |
| Sub2-51 | m/z = 209.02(C9H5ClFN3 = 209.61) | Sub2-52 | m/z = 303.04(C15H8ClF2N3 = 303.7) |
| Sub2-53 | m/z = 317.05(C17H8ClN5 = 317.74) | Sub2-54 | m/z = 359.09(C23H15ClFN = 359.83) |
| Sub2-55 | m/z = 266.06(C16H11ClN2 = 266.73) | Sub2-56 | m/z = 418.12(C28H19ClN2 = 418.92) |
| Sub2-57 | m/z = 330.09(C21H15ClN2 = 330.82) | Sub2-58 | m/z = 392.11(C26H17ClN2 = 392.89) |
| Sub2-59 | m/z = 434.13(C27H19ClN4 = 434.93) | Sub2-60 | m/z = 391.11(C27H18ClN = 391.9) |
| Sub2-61 | m/z = 473.08(C29H16ClN3S = 473.98) | Sub2-62 | m/z = 447.08(C27H14ClN3O2 = 447.88) |
| Sub2-63 | m/z = 433.1(C27H16ClN3O = 433.9) | Sub2-64 | m/z = 449.08(C27H16ClN3S = 449.96) |
| Sub2-65 | m/z = 432.11(C27H17ClN4 = 432.91) | Sub2-66 | m/z = 446.08(C28H15ClN2O2 = 446.89) |
| Sub2-67 | m/z = 358.09(C22H15ClN2O = 358.83) | | |

II. Synthesis of Product

1. Synthesis of P-1

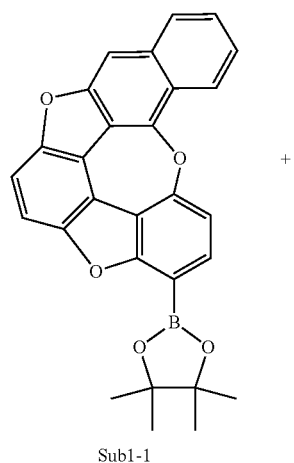

Sub1-1

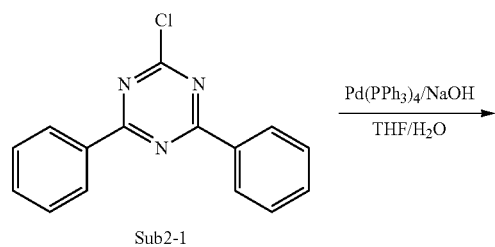

Sub2-1

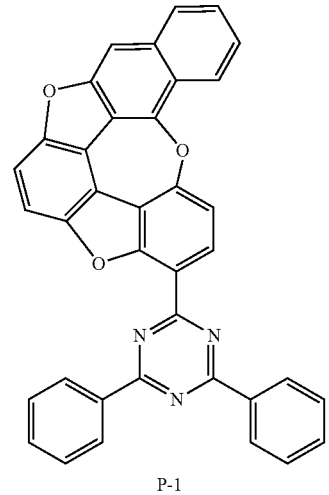

P-1

Sub1-1 (22 g, 0.05 mol), Sub2-1 (13.1 g, 0.05 mol), Pd(pph$_3$)$_4$ (1.7 g, 0.001 mol), NaOH (5.9 g, 0.15 mol) were added to THF (100 ml) and water (30 ml), and stirred at 70° C. for 6 hours. After the reaction was completed, the solid generated during the reaction was filtered and the solid was separated using a silica gel column or recrystallization method to obtain 23 g (84.7%) of product P-1.

2. Synthesis of P-5
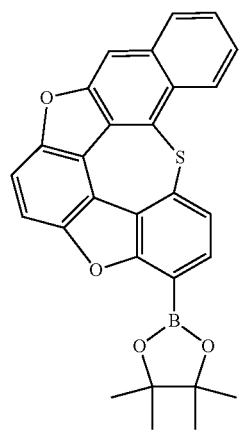
Sub1-5
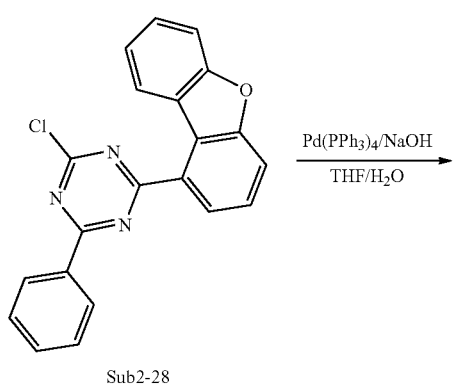
Sub2-28
→ Pd(PPh₃)₄/NaOH, THF/H₂O
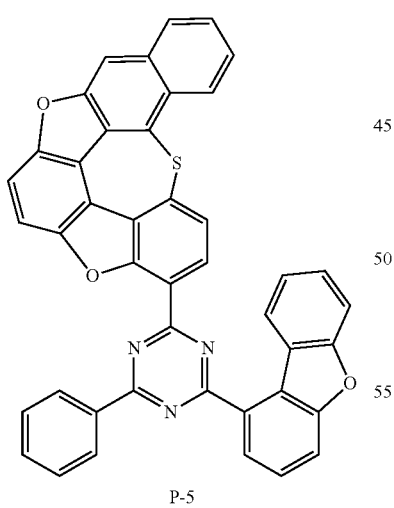
P-5
Sub1-5 (25 g, 0.05 mol), Sub2-28 (19.2 g, 0.05 mol), Pd(pph₃)₄ (1.9 g, 0.002 mol), NaOH (5.9 g, 0.15 mol) were added to THF (100 ml) and water (30 ml), and stirred at 70° C. for 6 hours. After the reaction was completed, 30 g (84.5%) of product P-5 was obtained by using the separation method for P-1 described above.
3. Synthesis of P-21
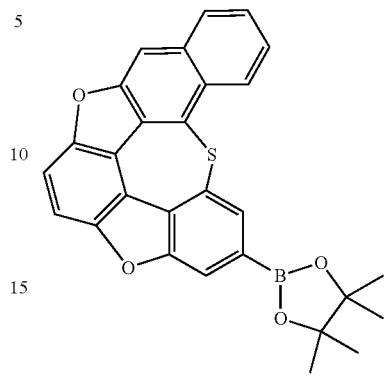
Sub1-17
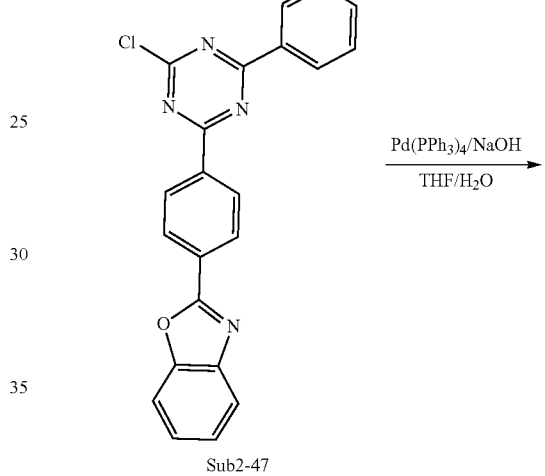
Sub2-47
→ Pd(PPh₃)₄/NaOH, THF/H₂O
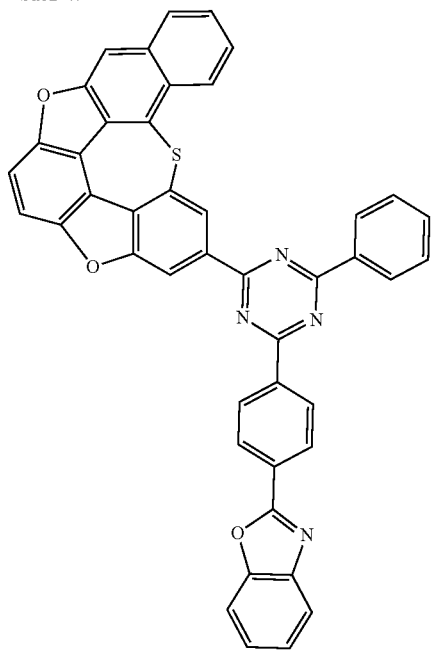
P-21
Sub1-17 (25 g, 0.05 mol), Sub2-47 (20.7 g, 0.05 mol), Pd(pph₃)₄ (1.9 g, 0.002 mol), NaOH (6.5 g, 0.16 mol) were added to THF (110 ml) and water (33 ml), and stirred at 70° C. for 6 hours. After the reaction was completed, 30 g (81.2%) of product P-21 was obtained by using the separation method for P-1 described above.

4. Synthesis of P-31

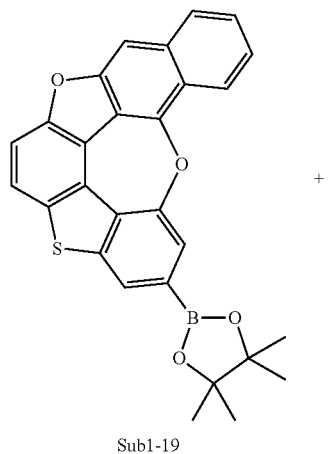
Sub1-19

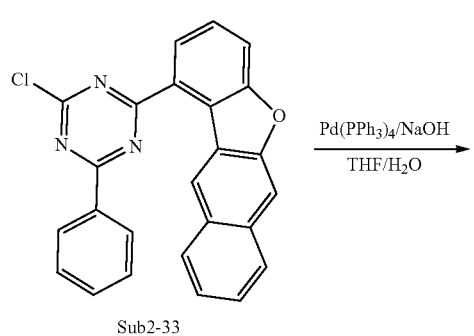
Sub2-33

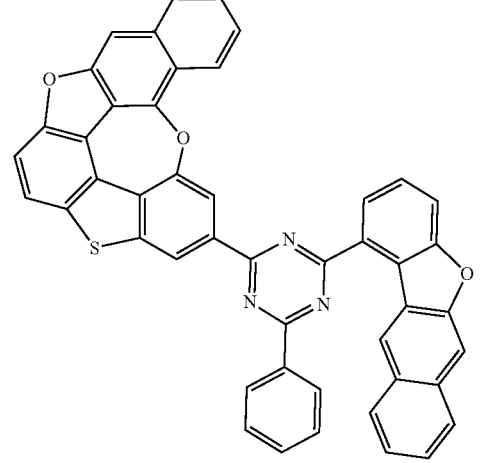
P-31

Sub1-19 (40 g, 0.09 mol), Sub2-33 (35.1 g, 0.09 mol), Pd(pph₃)₄ (3.0 g, 0.003 mol), NaOH (10.3 g, 0.26 mol) were added to THF (172 ml) and water (60 ml), and stirred at 70° C. for 6 hours. After the reaction was completed, 55 g (90%) of product P-31 was obtained by using the separation method for P-1 described above.

5. Synthesis of P-45

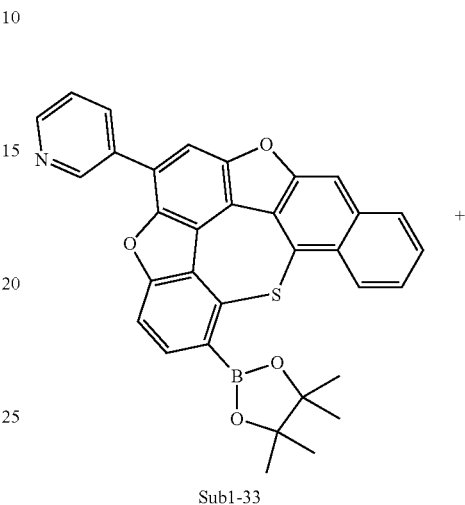
Sub1-33

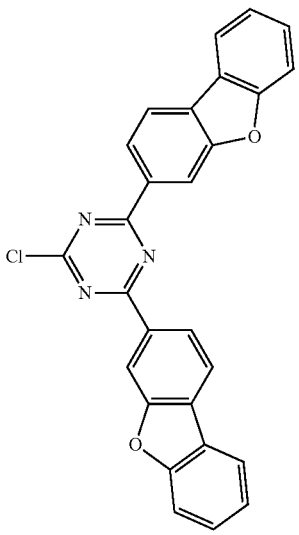
Sub2-30

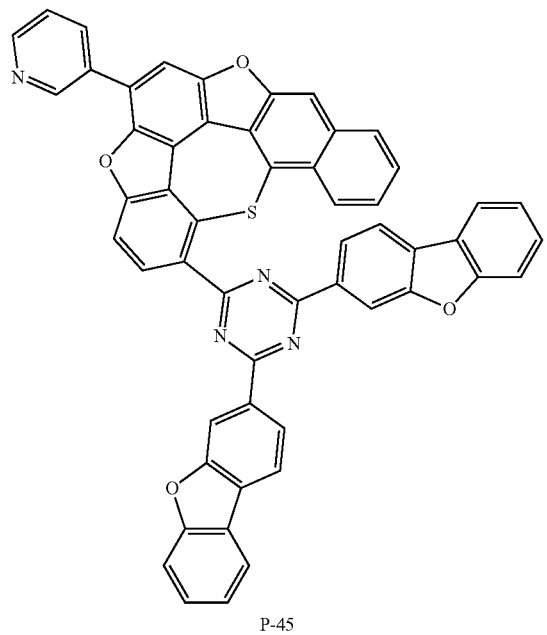

P-45

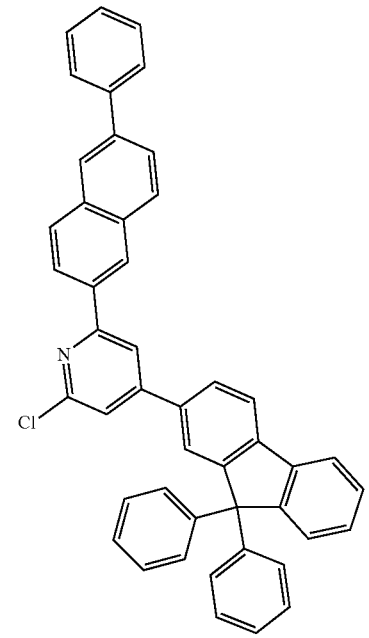

Sub2-24

Sub1-33 (30 g, 0.06 mol), Sub2-30 (24.8 g, 0.06 mol), Pd(pph₃)₄ (1.9 g, 0.002 mol), NaOH (6.7 g, 0.17 mol) were added to THF (110 ml) and water (30 ml), and stirred at 70° C. for 6 hours. After the reaction was completed, 41 g (89.5%) of product P-45 was obtained by using the separation method for P-1 described above.

6. Synthesis of P-56

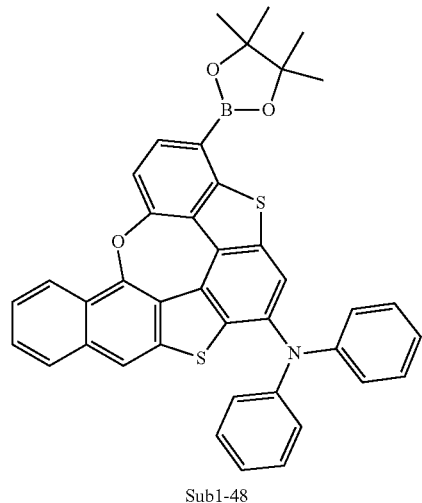

Sub1-48

+

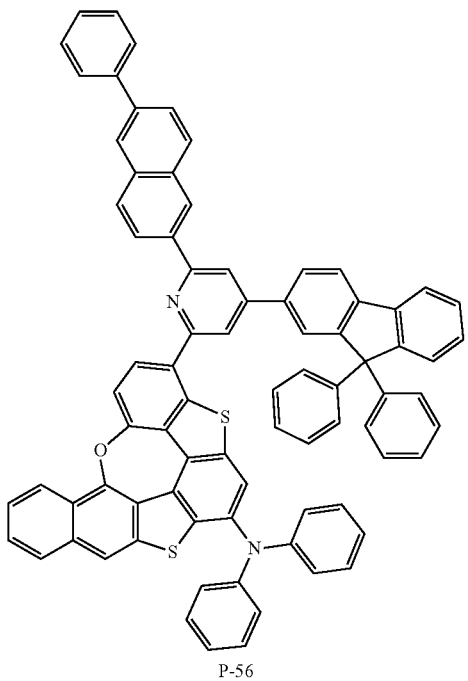

P-56

Sub1-48 (30 g, 0.05 mol), Sub2-24 (29.3 g, 0.05 mol), Pd(pph₃)₄ (1.6 g, 0.001 mol), NaOH (5.6 g, 0.14 mol) were added to THF (100 ml) and water (30 ml), and stirred at 70° C. for 6 hours. After the reaction was completed, 43 g (83%) of product P-56 was obtained by using the separation method for P-1 described above.

Meanwhile, the FD-MS values of the compounds P-1 to P-100 of the present invention prepared according to the above synthesis examples are shown in Table 3 below.

TABLE 3

| compound | FD-MS | compound | FD-MS |
|---|---|---|---|
| P-1 | m/z = 553.14($C_{37}H_{19}N_3O_3$ = 553.58) | P-2 | m/z = 619.14($C_{41}H_{21}N_3O_2S$ = 619.7) |
| P-3 | m/z = 685.13($C_{45}H_{23}N_3OS_2$ = 685.82) | P-4 | m/z = 677.11($C_{43}H_{23}N_3S_3$ = 677.86) |
| P-5 | m/z = 659.13($C_{43}H_{21}N_3O_3S$ = 659.72) | P-6 | m/z = 737.16($C_{49}H_{27}N_3OS_2$ = 737.9) |
| P-7 | m/z = 645.15($C_{43}H_{23}N_3O_2S$ = 645.74) | P-8 | m/z = 826.19($C_{55}H_{30}N_4OS_2$ = 826.99) |
| P-9 | m/z = 630.17($C_{42}H_{22}N_4O_3$ = 630.66) | P-10 | m/z = 775.14($C_{51}H_{25}N_3O_2S_2$ = 775.9) |
| P-11 | m/z = 613.13($C_{39}H_{23}N_3OS_2$ = 613.75) | P-12 | m/z = 813.22($C_{53}H_{19}D_{10}N_3S_3$ = 814.08) |
| P-13 | m/z = 675.11($C_{43}H_{21}N_3O_2S_2$ = 675.78) | P-14 | m/z = 841.15($C_{55}H_{27}N_3O_3S_2$ = 841.96) |
| P-15 | m/z = 751.14($C_{49}H_{25}N_3O_2S_2$ = 751.88) | P-16 | m/z = 701.16($C_{46}H_{27}N_3OS_2$ = 701.86) |
| P-17 | m/z = 495.1($C_{31}H_{14}FN_3O_3$ = 495.47) | P-18 | m/z = 569.12($C_{37}H_{19}N_3O_2S$ = 569.64) |
| P-19 | m/z = 685.13($C_{45}H_{23}N_3OS_2$ = 685.82) | P-20 | m/z = 753.14($C_{49}H_{27}N_3S_3$ = 753.96) |
| P-21 | m/z = 686.14($C_{44}H_{22}N_4O_3S$ = 686.75) | P-22 | m/z = 941.23($C_{63}H_{35}N_5OS_2$ = 942.13) |
| P-23 | m/z = 569.12($C_{37}H_{19}N_3O_2S$ = 569.64) | P-24 | m/z = 725.12($C_{47}H_{23}N_3O_2S_2$ = 725.84) |
| P-25 | m/z = 553.14($C_{37}H_{19}N_3O_3$ = 553.58) | P-26 | m/z = 721.18($C_{49}H_{27}N_3O_2S$ = 721.83) |
| P-27 | m/z = 637.13($C_{41}H_{23}N_3OS_2$ = 637.78) | P-28 | m/z = 855.15($C_{56}H_{29}N_3OS_3$ = 856.05) |
| P-29 | m/z = 675.13($C_{43}H_{21}N_3O_4S$ = 675.72) | P-30 | m/z = 585.1($C_{37}H_{19}N_3OS_2$ = 585.7) |
| P-31 | m/z = 709.15($C_{47}H_{23}N_3O_3S$ = 709.78) | P-32 | m/z = 823.18($C_{56}H_{29}N_3OS_2$ = 823.99) |
| P-33 | m/z = 693.17($C_{47}H_{23}N_3O_4$ = 693.72) | P-34 | m/z = 695.17($C_{47}H_{25}N_3O_2S$ = 695.8) |
| P-35 | m/z = 767.12($C_{49}H_{25}N_3OS_3$ = 767.94) | P-36 | m/z = 751.12($C_{49}H_{25}N_3S_3$ = 751.94) |
| P-37 | m/z = 659.13($C_{43}H_{21}N_3O_3S$ = 659.72) | P-38 | m/z = 635.11($C_{41}H_{21}N_3OS_2$ = 635.76) |
| P-39 | m/z = 963.26($C_{67}H_{37}N_3O_3S$ = 964.11) | P-40 | m/z = 585.1($C_{37}H_{19}N_3OS_2$ = 585.7) |
| P-41 | m/z = 603.16($C_{41}H_{21}N_3O_3$ = 603.64) | P-42 | m/z = 669.15($C_{45}H_{23}N_3O_2S$ = 669.76) |
| P-43 | m/z = 751.14($C_{49}H_{25}N_3O_2S_2$ = 751.88) | P-44 | m/z = 601.07($C_{37}H_{19}N_3S_3$ = 601.76) |
| P-45 | m/z = 826.17($C_{54}H_{26}N_4O_4S$ = 826.89) | P-46 | m/z = 621.08($C_{37}H_{17}F_2N_3OS_2$ = 621.68) |
| P-47 | m/z = 645.15($C_{43}H_{23}N_3O_2S$ = 645.74) | P-48 | m/z = 635.09($C_{39}H_{17}N_5OS_2$ = 635.72) |
| P-49 | m/z = 552.15($C_{38}H_{20}N_2O_3$ = 552.59) | P-50 | m/z = 618.14($C_{42}H_{22}N_2O_2S$ = 618.71) |
| P-51 | m/z = 684.13($C_{46}H_{24}N_2OS_2$ = 684.83) | P-52 | m/z = 676.11($C_{44}H_{24}N_2S_3$ = 676.87) |
| P-53 | m/z = 774.2($C_{53}H_{30}N_2O_3S$ = 774.89) | P-54 | m/z = 764.12($C_{50}H_{24}N_2O_3S_2$ = 764.87) |
| P-55 | m/z = 719.19($C_{51}H_{29}NO_2S$ = 719.86) | P-56 | m/z = 1116.32($C_{80}H_{48}N_2OS_2$ = 1117.4) |
| P-57 | m/z = 570.14($C_{38}H_{19}FN_2O_3$ = 570.58) | P-58 | m/z = 713.11($C_{47}H_{23}NO_3S_2$ = 713.83) |
| P-59 | m/z = 648.13($C_{43}H_{24}N_2OS_2$ = 648.8) | P-60 | m/z = 726.13($C_{48}H_{26}N_2S_3$ = 726.93) |
| P-61 | m/z = 749.15($C_{51}H_{27}NO_2S_2$ = 749.9) | P-62 | m/z = 584.1($C_{38}H_{20}N_2OS_2$ = 584.71) |
| P-63 | m/z = 720.19($C_{50}H_{28}N_2O_2S$ = 720.85) | P-64 | m/z = 684.13($C_{46}H_{24}N_2OS_2$ = 684.83) |
| P-65 | m/z = 589.18($C_{41}H_{23}N_3O_2$ = 589.65) | P-66 | m/z = 731.2($C_{51}H_{29}N_3OS$ = 731.87) |
| P-67 | m/z = 555.14($C_{37}H_{21}N_3OS$ = 555.66) | P-68 | m/z = 871.18($C_{57}H_{33}N_3OS_3$ = 872.09) |
| P-69 | m/z = 687.2($C_{46}H_{29}N_3O_2S$ = 687.82) | P-70 | m/z = 671.15($C_{45}H_{25}N_3S_2$ = 671.84) |
| P-71 | m/z = 655.23($C_{46}H_{29}N_3O_2$ = 655.76) | P-72 | m/z = 859.21($C_{60}H_{33}N_3S_2$ = 860.07) |
| P-73 | m/z = 704.22($C_{49}H_{28}N_4O_2$ = 704.79) | P-74 | m/z = 792.25($C_{56}H_{32}N_4O_2$ = 792.9) |
| P-75 | m/z = 710.15($C_{48}H_{26}N_2OS_2$ = 710.87) | P-76 | m/z = 663.14($C_{43}H_{25}N_3OS_2$ = 663.81) |
| P-77 | m/z = 736.16($C_{50}H_{28}N_2OS_2$ = 736.91) | P-78 | m/z = 722.21($C_{49}H_{30}N_4OS$ = 722.87) |
| P-79 | m/z = 647.17($C_{45}H_{26}FNOS$ = 647.77) | P-80 | m/z = 831.26($C_{61}H_{37}NOS$ = 832.03) |

[Example 1] Red Organic Light Emitting Device (Phosphorescent Host)

An organic electroluminescent device was manufactured according to a conventional method by using the compound obtained through synthesis as a light emitting host material of the emitting layer. First, a N1-(naphthalen-2-yl)-N4,N4-bis(4-(naphthalen-2-yl(phenyl)amino)phenyl)-N1-phenylbenzene-1,4-diamine (Abbreviated as 2-TNATA) film was vacuum-deposited on the ITO layer (anode) formed on a glass substrate to form a 60 nm-thick hole injection layer, and 4,4-bis[N-(1-naphthyl)-N-phenylamino]biphenyl (hereinafter abbreviated as -NPD) as a hole transport compound on the hole injection layer was vacuum-deposited to a thickness of 60 nm to form a hole transport layer. The compound (P-1) of the present invention represented by Formula 1 was used as a host on the hole transport layer, and (piq)2Ir(acac)[bis-(1-phenylisoquinolyl)iridium(III)acetylacetonate] as a dopant material was doped at a weight ratio of 95:5 to deposit an emitting layer to a thickness of 30 nm. Subsequently, (1,1'-bisphenyl)-4-oleato)bis(2-methyl-8-quinolineoleato)aluminum (abbreviated as BAlq) as a hole-blocking layer was vacuum-deposited to a thickness of 10 nm, and as an electron transport layer, tris(8-quinolinol) aluminum (abbreviated as Alq3) was deposited to a thickness of 40 nm. Then, as an electron injection layer, LiF, an alkali metal halide, was deposited to a thickness of 0.2 nm, and then, Al was deposited to a thickness of 150 nm and used as a cathode to prepare an organic electroluminescent device.

[Example 2] to [Example 21]

An organic electroluminescent device was manufactured in the same manner as in Example 1, except that the compound of the present invention described in Table 4 was used instead of the compound P-1 of the present invention as the host material of the emitting layer.

[Comparative Example 1] to [Comparative Example 2]

An organic electroluminescent device was manufactured in the same manner as in Example 1, except that Comparative Compound A to Comparative Compound B were used as host materials for the emitting layer.

<Comparative compound A>

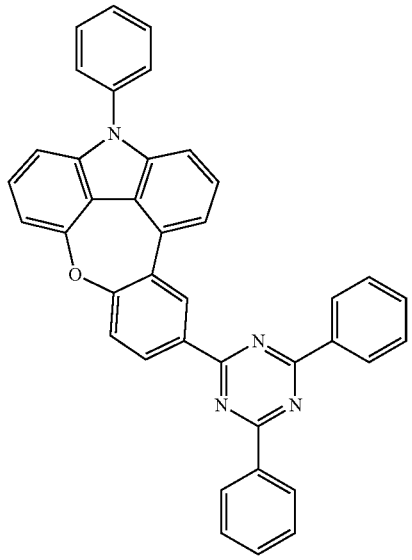

<Comparative compound B>

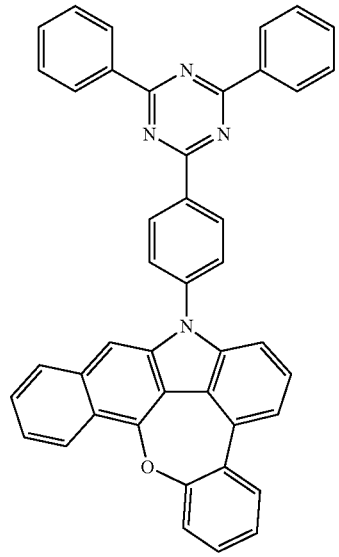

By applying a forward bias DC voltage to the organic electronic devices prepared in Examples 1 to 21 and Comparative Examples 1 to 2 prepared in this way, Electroluminescence (EL) characteristics were measured with PR-650 from photo research, and as a result of the measurement, the T95 lifetime was measured using a lifetime measuring device manufactured by McScience at 2500 cd/m² standard luminance. Table 4 below shows the device fabrication and evaluation results.

TABLE 4

| | compound | Voltage | Current Density (mA/cm²) | Brightness (cd/m²) | Efficiency (cd/A) | T(95) | CIE x | CIE y |
|---|---|---|---|---|---|---|---|---|
| comparative example(1) | comparative compound A | 5.8 | 11.3 | 2500.0 | 22.2 | 99.4 | 0.63 | 0.31 |
| comparative example(2) | comparative compound B | 5.7 | 10.8 | 2500.0 | 23.1 | 108.1 | 0.64 | 0.34 |
| example(1) | P-1 | 5.1 | 8.6 | 2500.0 | 29.1 | 127.6 | 0.64 | 0.30 |
| example(2) | P-4 | 5.0 | 8.9 | 2500.0 | 28.2 | 126.1 | 0.62 | 0.31 |
| example(3) | P-5 | 4.8 | 8.4 | 2500.0 | 29.7 | 116.9 | 0.60 | 0.32 |
| example(4) | P-13 | 4.7 | 8.3 | 2500.0 | 30.0 | 117.7 | 0.61 | 0.34 |
| example(5) | P-16 | 5.0 | 8.0 | 2500.0 | 31.3 | 115.4 | 0.64 | 0.31 |
| example(6) | P-21 | 4.9 | 8.8 | 2500.0 | 28.4 | 113.8 | 0.65 | 0.31 |
| example(7) | P-25 | 5.1 | 8.5 | 2500.0 | 29.3 | 128.4 | 0.62 | 0.32 |
| example(8) | P-28 | 4.9 | 8.2 | 2500.0 | 30.4 | 116.1 | 0.62 | 0.34 |
| example(9) | P-31 | 4.8 | 8.2 | 2500.0 | 30.6 | 120.0 | 0.64 | 0.35 |
| example(10) | P-32 | 5.0 | 8.0 | 2500.0 | 31.1 | 125.3 | 0.60 | 0.34 |
| example(11) | P-34 | 5.2 | 9.0 | 2500.0 | 27.7 | 121.5 | 0.62 | 0.31 |
| example(12) | P-37 | 4.8 | 8.3 | 2500.0 | 30.2 | 118.4 | 0.63 | 0.34 |
| example(13) | P-43 | 5.1 | 8.7 | 2500.0 | 28.6 | 120.7 | 0.63 | 0.35 |
| example(14) | P-46 | 4.7 | 9.0 | 2500.0 | 27.9 | 113.1 | 0.65 | 0.31 |
| example(15) | P-49 | 5.4 | 9.1 | 2500.0 | 27.5 | 123.8 | 0.65 | 0.33 |
| example(16) | P-52 | 5.4 | 9.3 | 2500.0 | 27.0 | 123.0 | 0.64 | 0.32 |
| example(17) | P-65 | 5.2 | 8.7 | 2500.0 | 28.8 | 124.6 | 0.63 | 0.31 |
| example(18) | P-67 | 5.2 | 8.5 | 2500.0 | 29.5 | 126.9 | 0.61 | 0.31 |
| example(19) | P-69 | 5.3 | 8.1 | 2500.0 | 30.9 | 114.6 | 0.62 | 0.32 |
| example(20) | P-73 | 5.3 | 9.2 | 2500.0 | 27.3 | 119.2 | 0.63 | 0.35 |
| example(21) | P-80 | 5.4 | 9.3 | 2500.0 | 26.8 | 122.3 | 0.61 | 0.33 |

As can be seen from the results in Table 4 above, when the compound of the present invention is used as a material for the emitting layer, it can be seen that the driving voltage is lowered and the efficiency and lifespan are significantly improved compared to the case of using the comparative compounds A to B.

The biggest difference from the comparative example compound is that the core element is different, and it can be seen that the device results are significantly different depending on the difference of the core element and the substitution position of sub-materials such as triazine, pyrimidine, and pyridine. Looking at the results, the major difference is the driving voltage, and it is expected that these results are due to the difference in the degree of structural distortion and the large difference in the LUMO level.

When the compounds of this patent are described in more detail, in the structure of this patent, when the type of element is S, it shows an advantage in terms of driving voltage, and when the type of element is O, it shows advantages in efficiency and lifespan. And depending on the position of the triazine, pyrimidine, and pyridine to be substituted, the electronic characteristics show a difference, and it is largely applied to the overall driving voltage, efficiency and lifespan of the device, and depending on whether the type of the secondary substituted substituent has a heterocyclic group, the lifespan results were affected. The balance aspect between the overall core and the sub greatly affected the device result, and the difference in characteristics was shown through the energy level (HOMO, LUMO) values of the example compounds, respectively.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

BRIEF DESCRIPTION OF THE DRAWINGS

| 100, 200, 300: organic electronic element | 110: the first electrode |
|---|---|
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting-auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST1: second stack |

What is claimed is:
1. A compound represented by Formula 1:

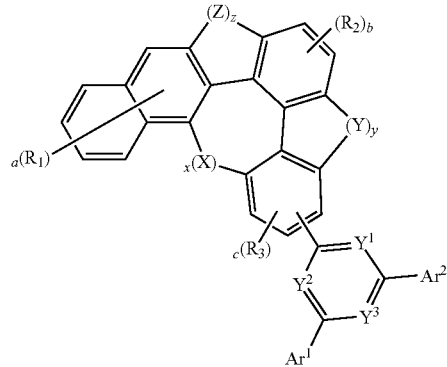

[Formula 1]

wherein:
1) $Ar^1$ and $Ar^2$ are each independently a $C_6$-$C_{60}$ aryl group; or a $C_2$-$C_{60}$ heterocyclic group including at least one hetero atom of O, N, S, Si or P;
2) $Y^1$, $Y^2$ and $Y^3$ are each independently N or CR', provided that at least one is N;
3) wherein R' is selected from the group consisting of hydrogen; deuterium; halogen; $C_1$-$C_{60}$ alkyl group; a $C_2$-$C_{60}$ alkenyl group; a $C_2$-$C_{60}$ alkynyl group; a $C_1$-$C_{60}$ alkoxyl group; a $C_6$-$C_{60}$ aryloxy group; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;
4) X, Y and Z are each independently O or S;
5) $R_1$, $R_2$ and $R_3$ are each the same or different, and each independently selected from the group consisting of hydrogen; deuterium; halogen; a $C_1$-$C_{60}$ alkyl group; a $C_2$-$C_{60}$ alkenyl group; a $C_2$-$C_{60}$ alkynyl group; a $C_1$-$C_{60}$ alkoxyl group; a $C_6$-$C_{60}$ aryloxy group; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; and -L'-N($R^a$)($R^b$);
6) wherein L' is selected from the group consisting of a single bond; a $C_6$-$C_{60}$ arylene group; a fluorenylene group; a $C_2$-$C_{60}$ heterocyclic group including at least one heteroatom of O, N, S, Si or P; and a $C_3$-$C_{30}$ aliphatic ring;
wherein $R^a$ and $R^b$ are each independently selected from the group consisting of a $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;
7) x, y and z are each independently 0 or 1, and x+y+z is 2 or 3;
8) a is an integer from 0 to 5, b and c are each independently an integer from 0 to 2;
9) wherein, the aryl group, heteroaryl group, arylene group, heterocyclic group, fluorenyl group, fluorenylene group, fused ring group, alkyl group, alkenyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; $C_8$-$C_{20}$ arylalkenyl group; and -L'-N($R^a$)($R^b$); the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

2. The compound of claim 1, wherein the compound represented by Formula 1 is represented by any one of Formulas 1-1 to 1-8:

[Formula 1-1]

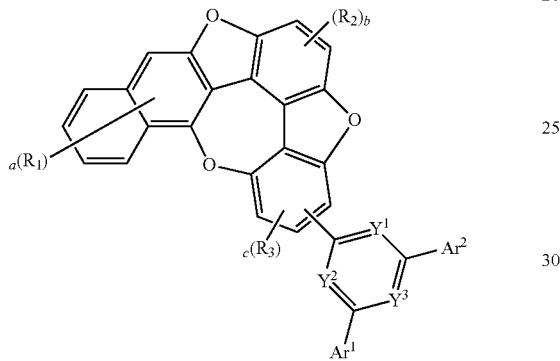

[Formula 1-2]

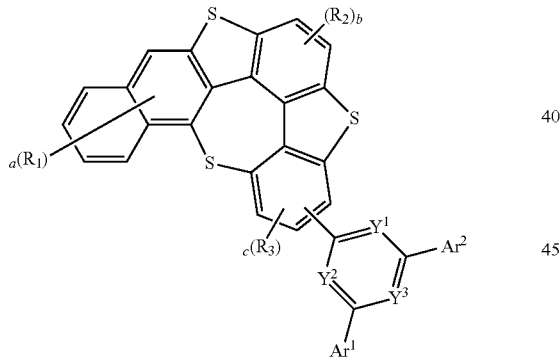

[Formula 1-3]

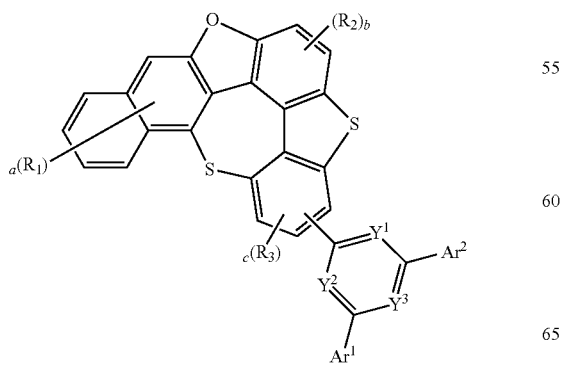

[Formula 1-4]

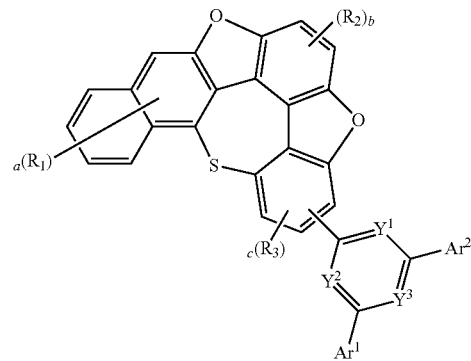

[Formula 1-5]

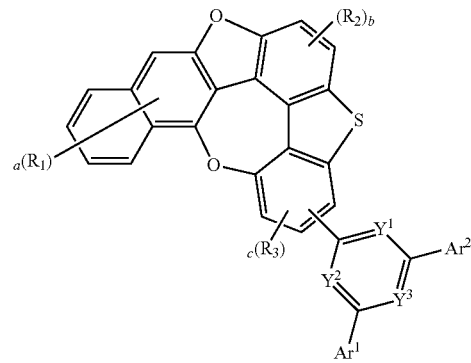

[Formula 1-6]

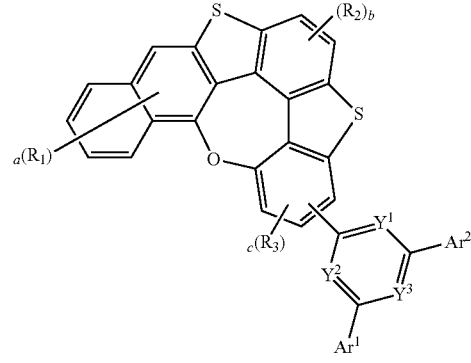

[Formula 1-7]

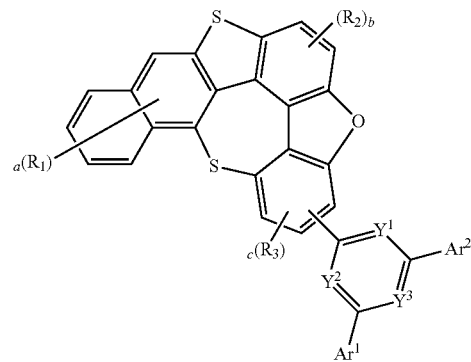

[Formula 1-8]
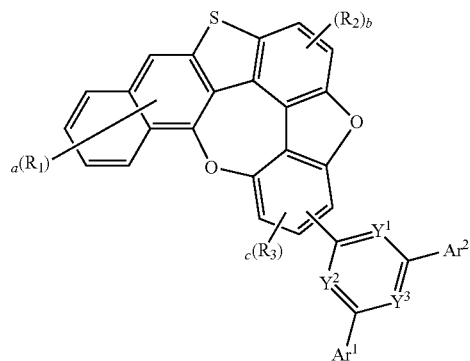
wherein:
Ar$^1$, Ar$^2$, Y$^1$, Y$^2$, Y$^3$, R$_1$, R$_2$, R$_3$, a, b and c are the same as defined in claim 1.
3. The compound of claim 1, wherein the compound represented by Formula 1 is represented by any one of Formulas 1-9 to 1-13:
[Formula 1-9]
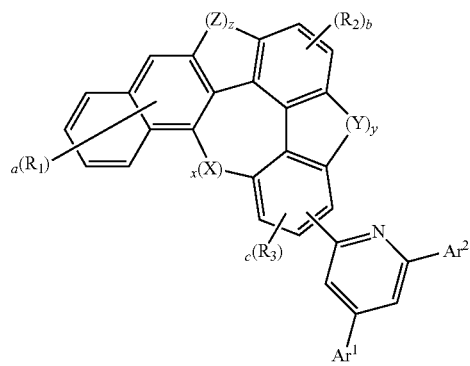
[Formulas 1-10]
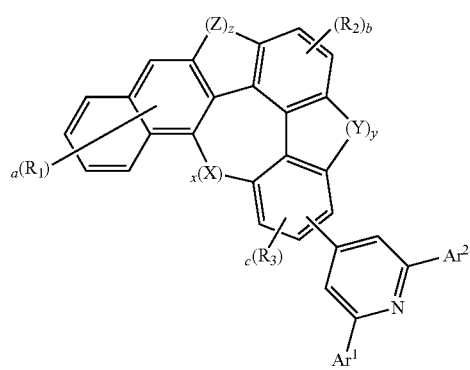
[Formulas 1-11]
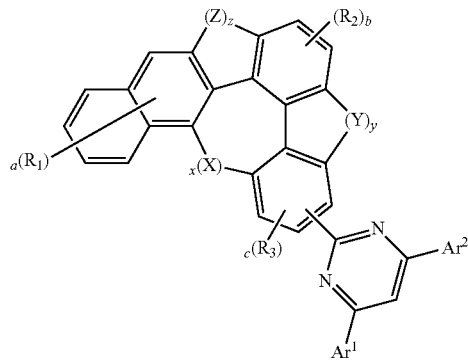
[Formulas 1-12]
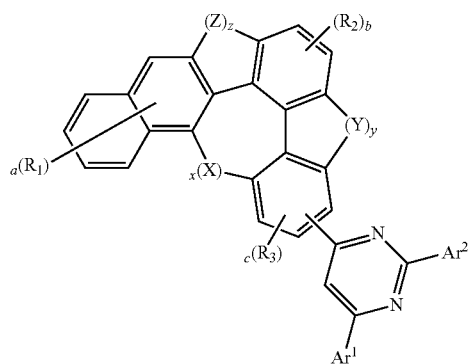
[Formulas 1-13]
wherein:
Ar$^1$, Ar$^2$, X, Y, Z, R$_1$, R$_2$, R$_3$, x, r, z, a, b and c are the same as defined in claim 1.

4. The compound of claim 1, wherein the compound represented by Formula 1 is represented by any one of Formulas 1-14 to 1-16:
[Formula 1-14]
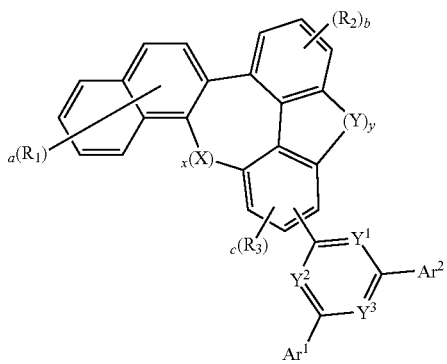
[Formula 1-15]
[Formula 1-16]
wherein:
Ar$^1$, Ar$^2$, Y$^1$, Y$^2$, Y$^3$, X, Y, Z, R$_1$, R$_2$, R$_3$, x, y, z, a, b and c are the same as defined in claim 1.
5. The compound of claim 1, wherein the compound represented by Formula 1 is any one of the following compounds P-1 to P-80:
P-1
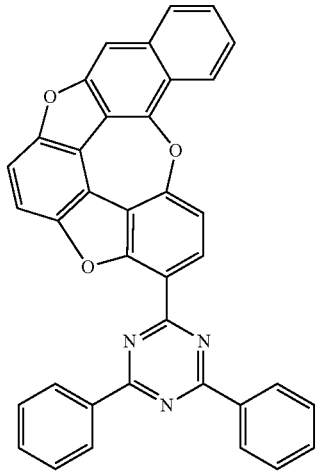
P-2
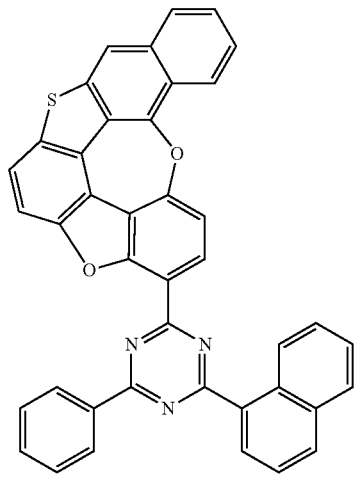
P-3
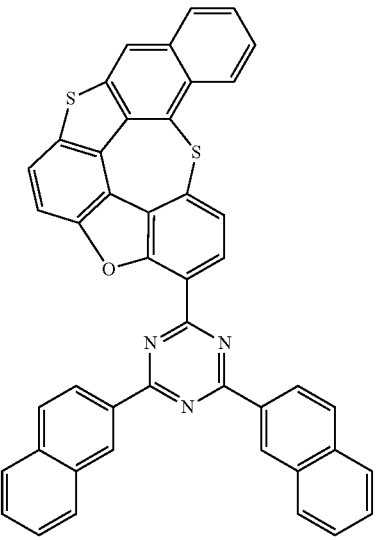

-continued
P-4
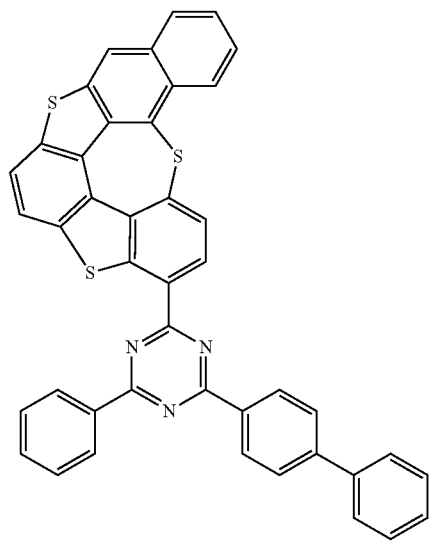
P-5
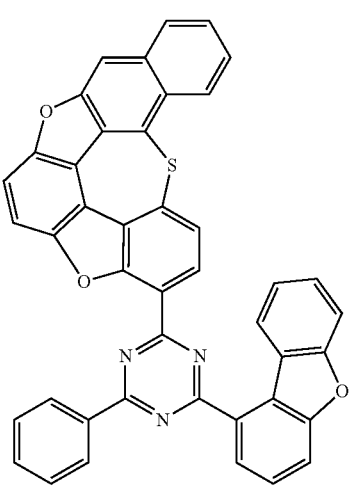
P-6
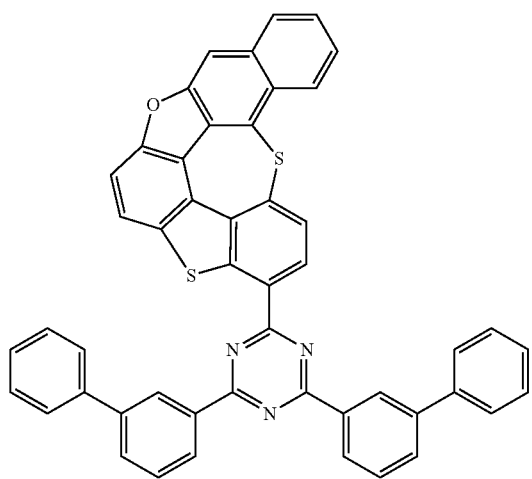
-continued
P-7
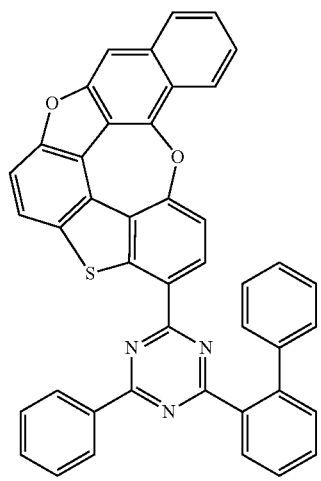
P-8
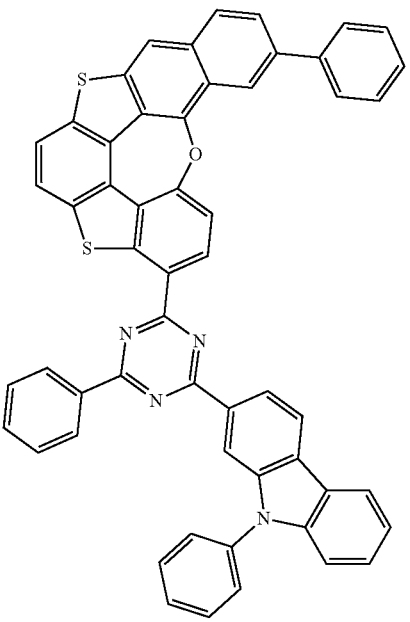
P-9
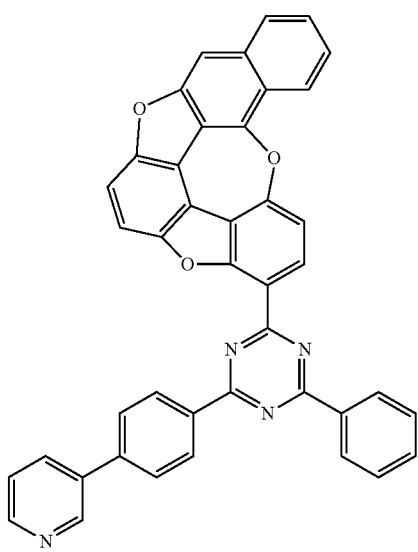

P-10
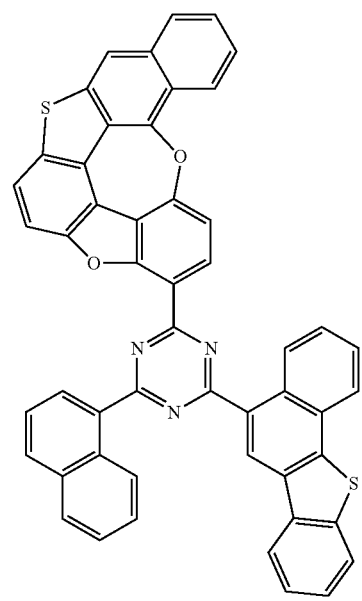
P-11
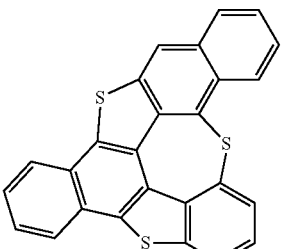
P-12
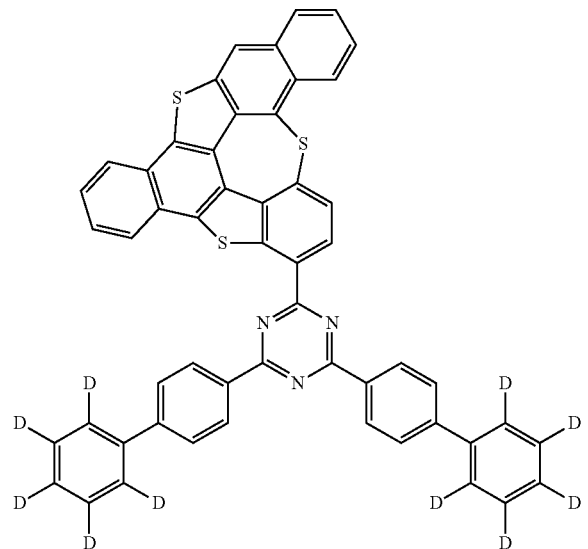
P-13
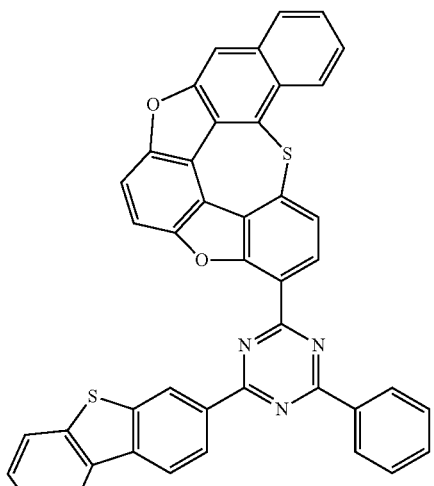
P-14
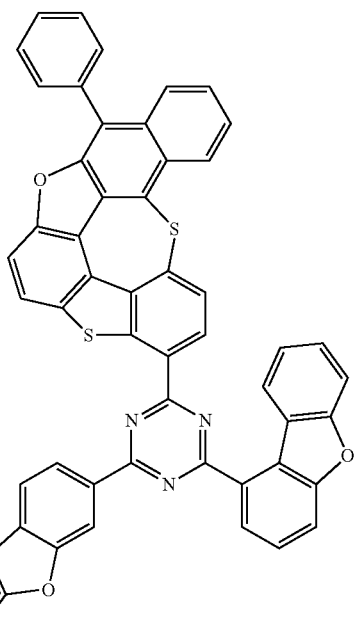
P-15
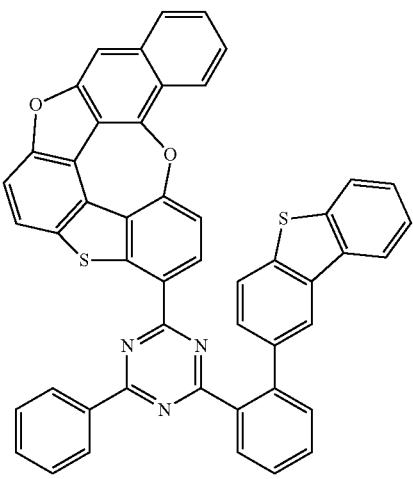

P-16
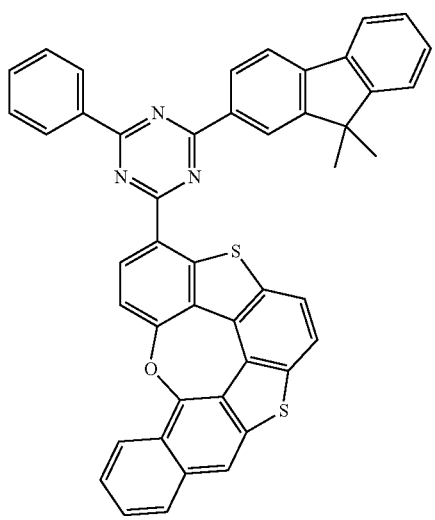
P-17
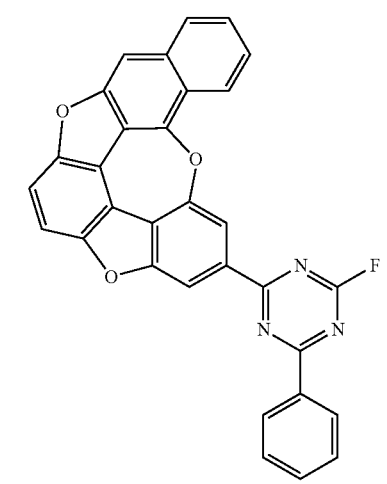
P-18
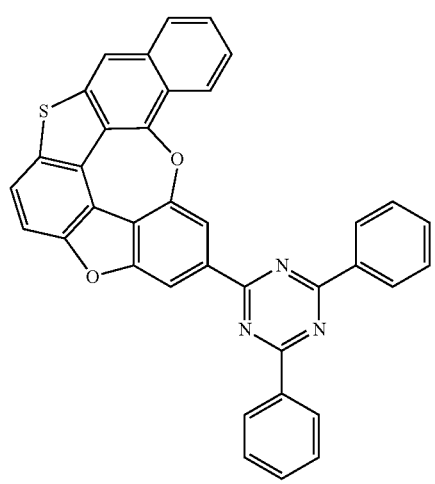
P-19
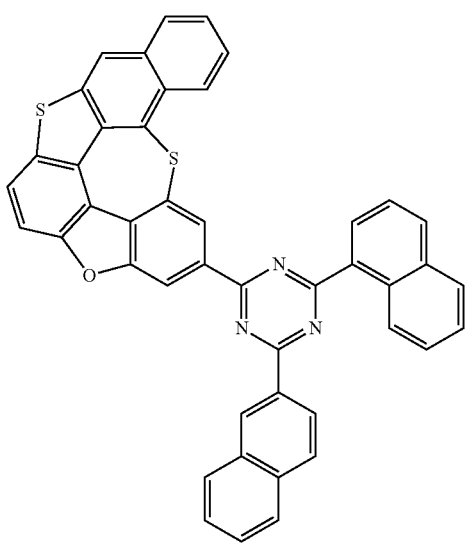
P-20
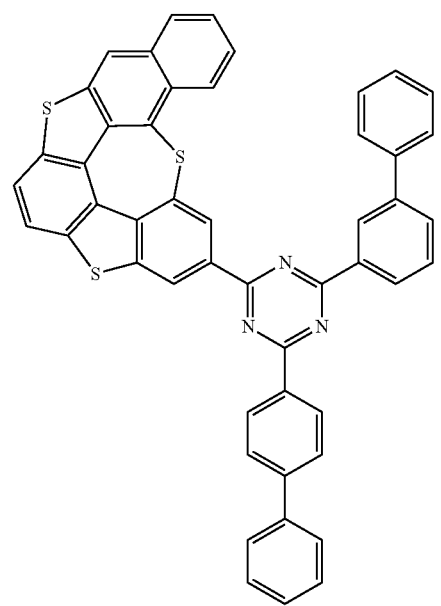

P-21
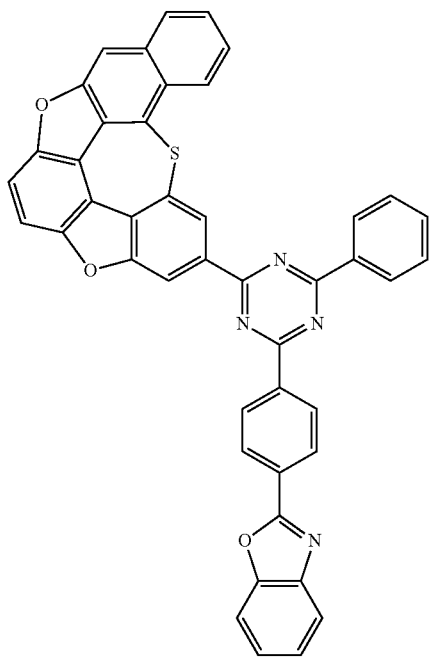
P-22
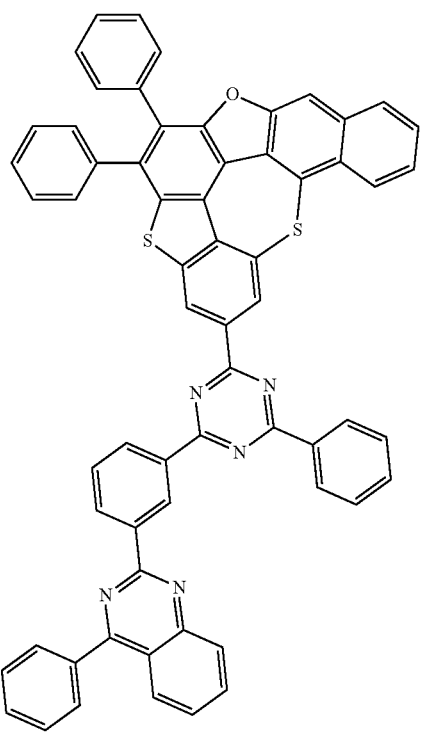
P-23
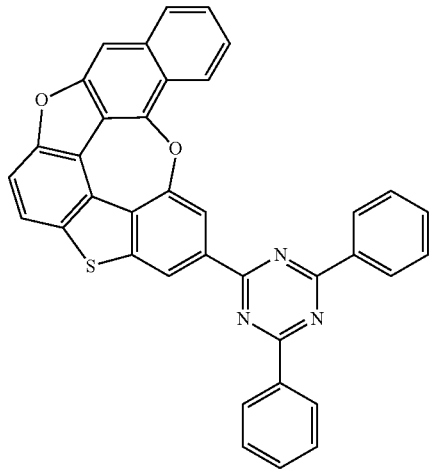
P-24
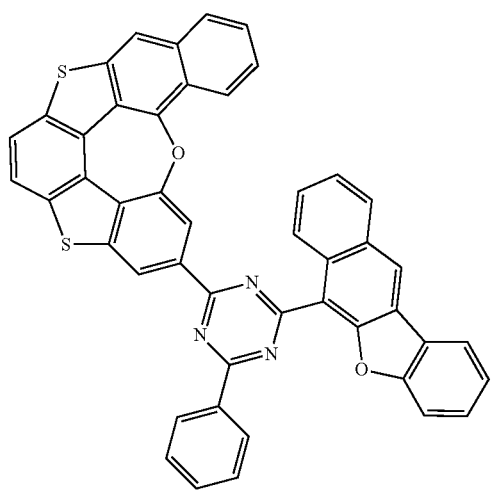
P-25
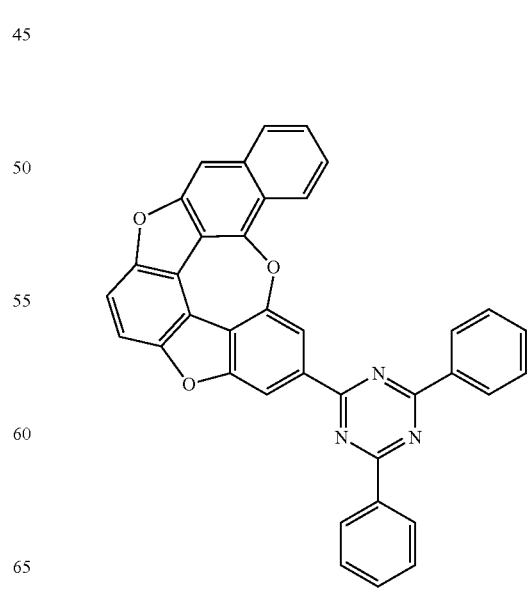

P-26
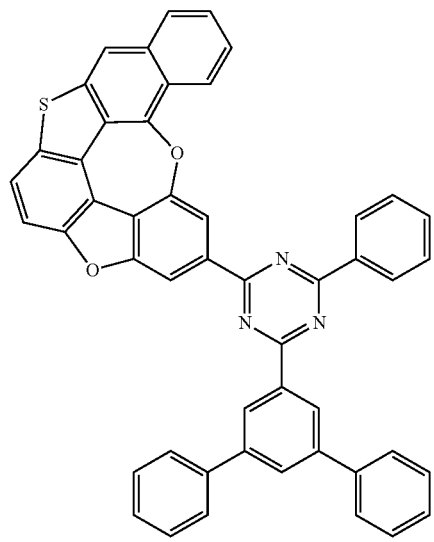
P-27
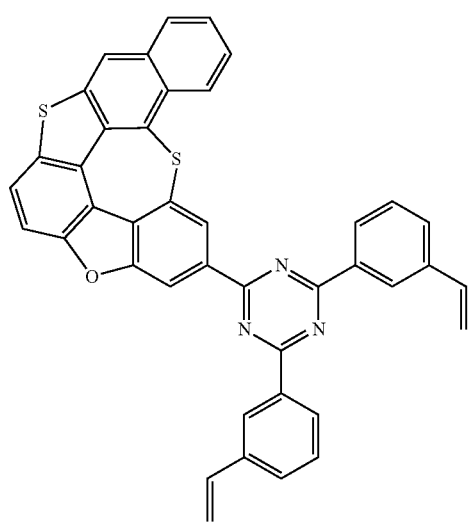
P-28
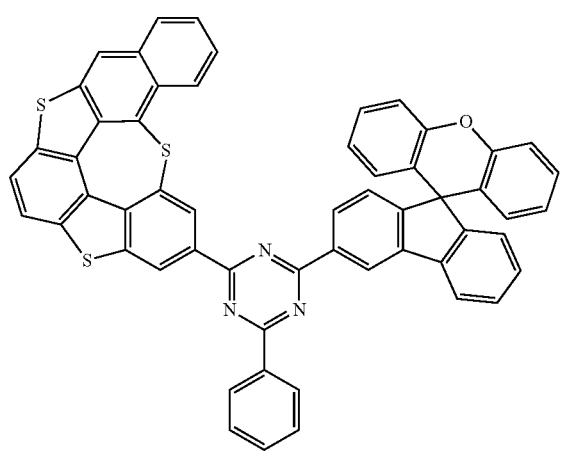
P-29
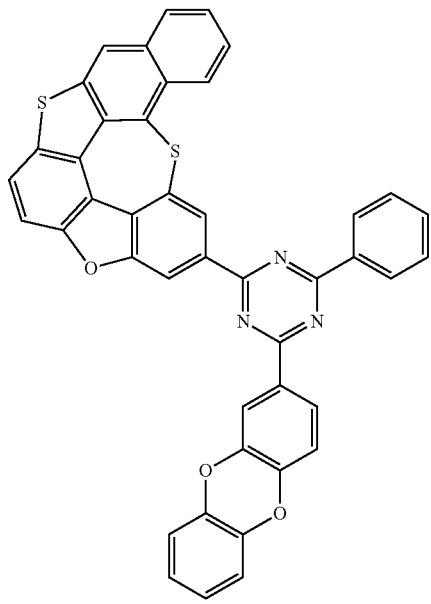
P-30
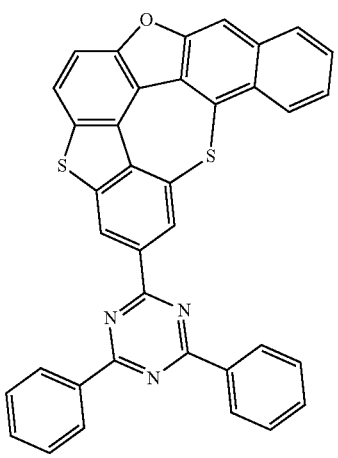
P-31
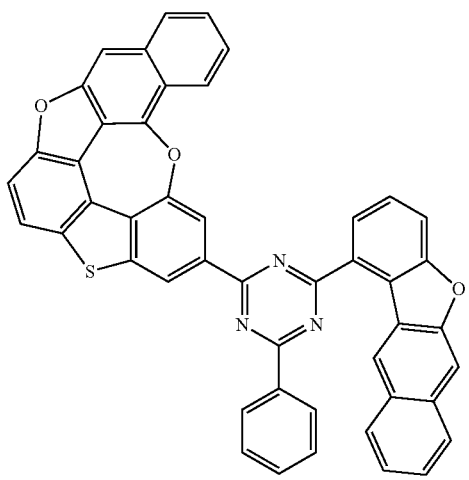

P-32
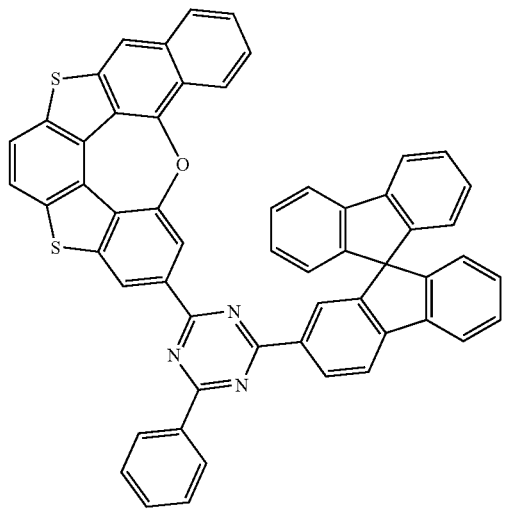
P-33
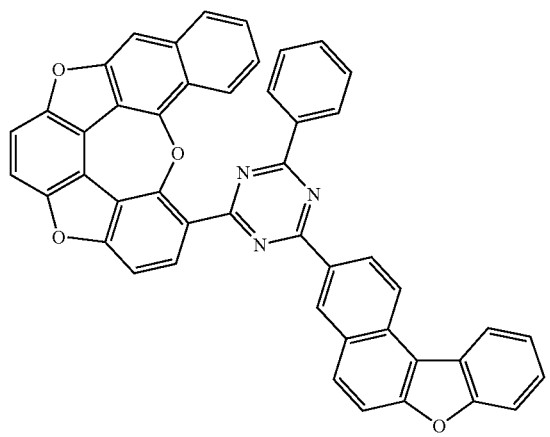
P-34
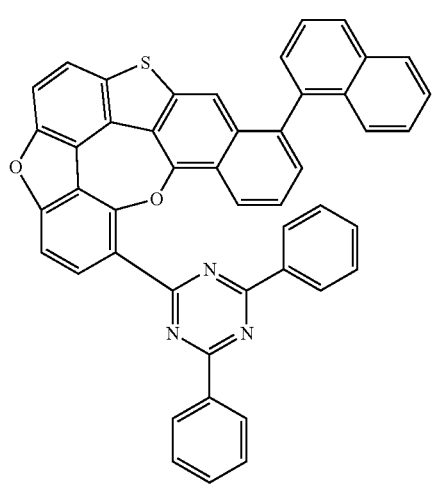
P-35
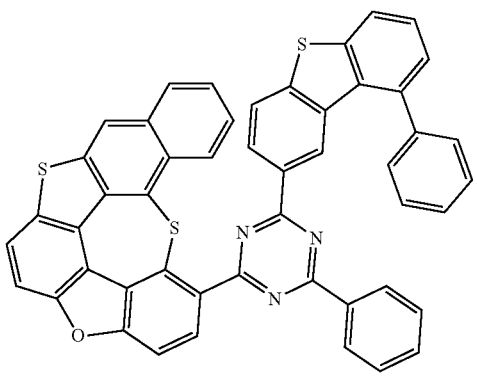
P-36
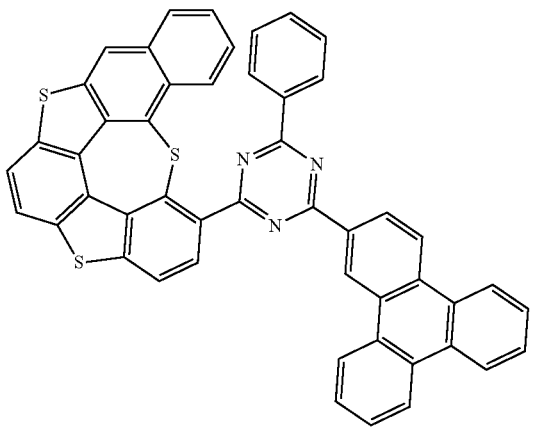
P-37
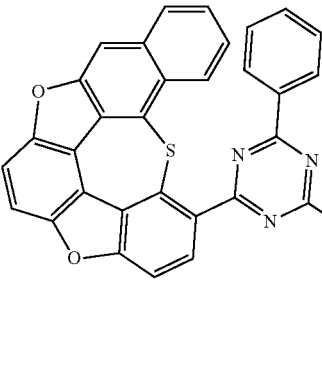

P-38
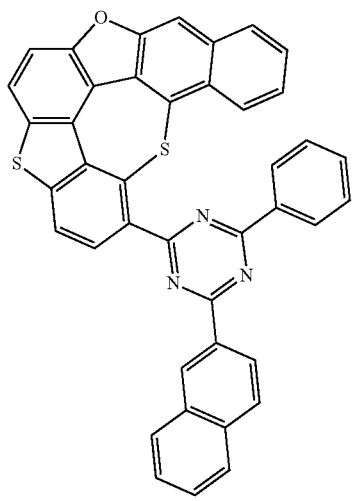
P-39
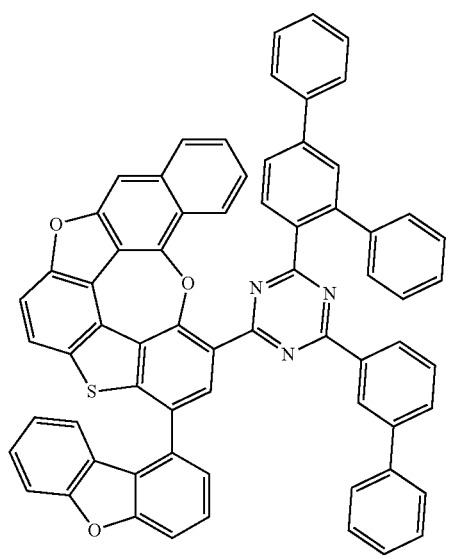
P-40
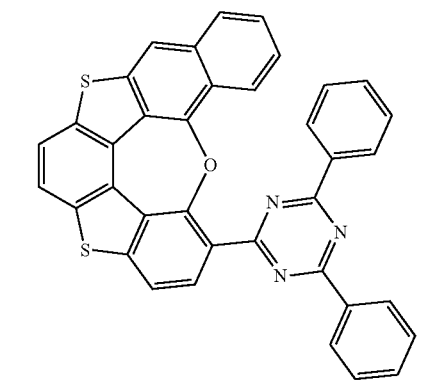
P-41
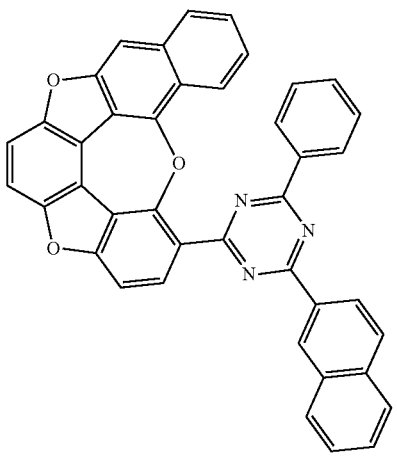
P-42
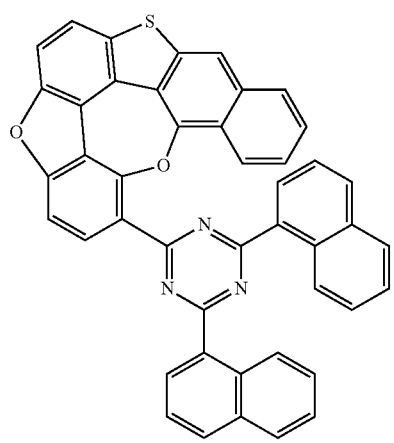
P-43
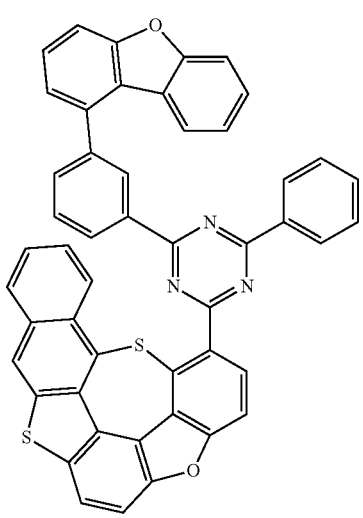

P-44
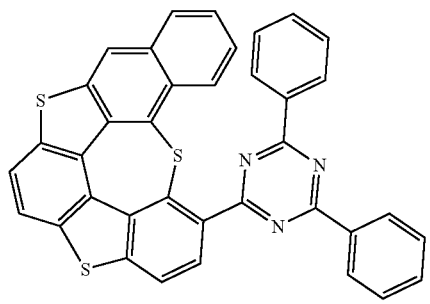
P-47
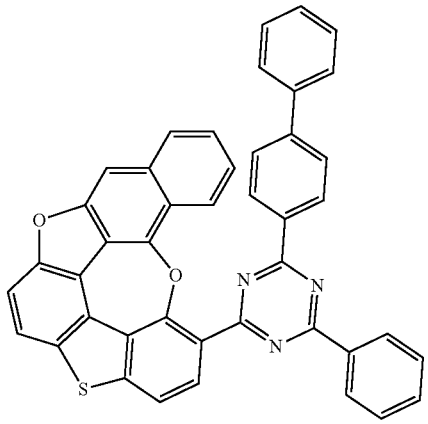
P-45
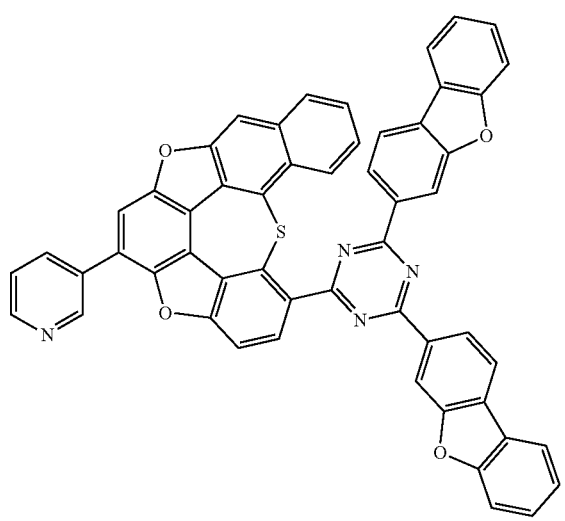
P-48
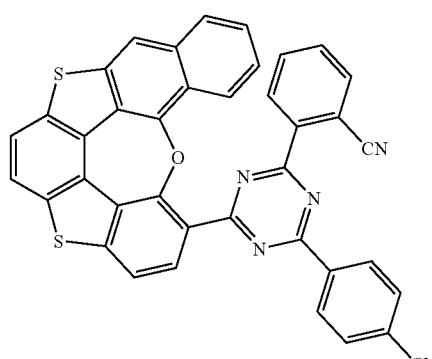
P-46
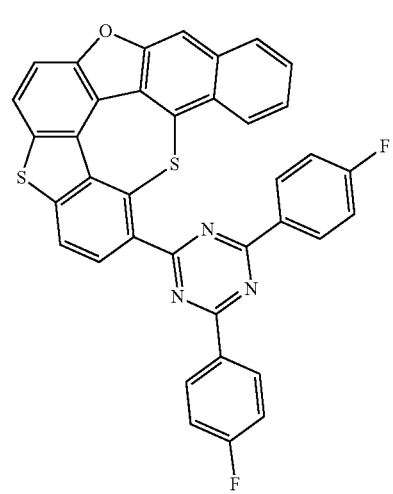
P-49
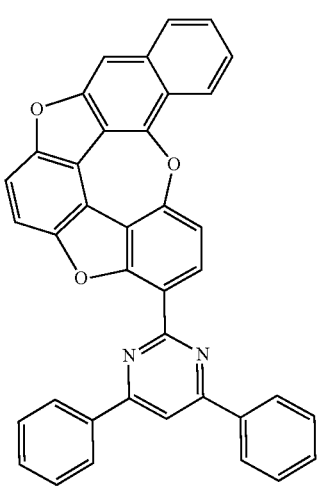

P-50
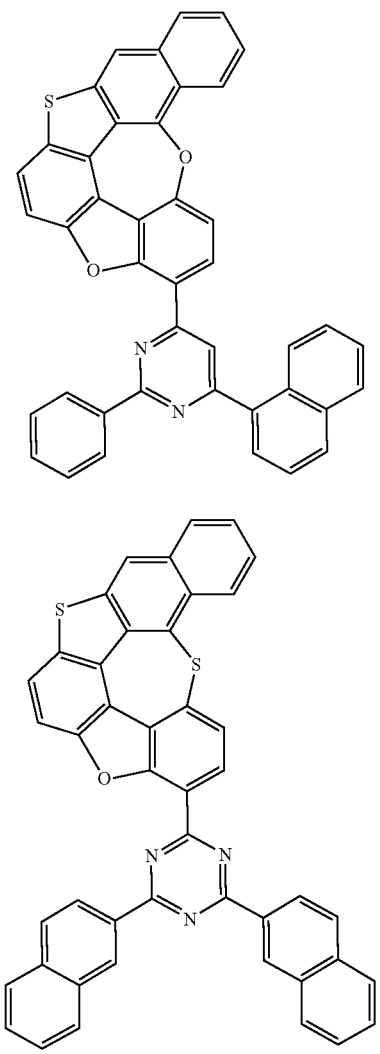
P-51
P-53
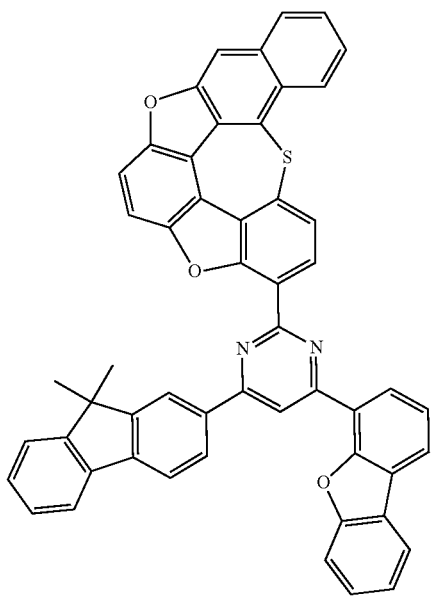
P-52
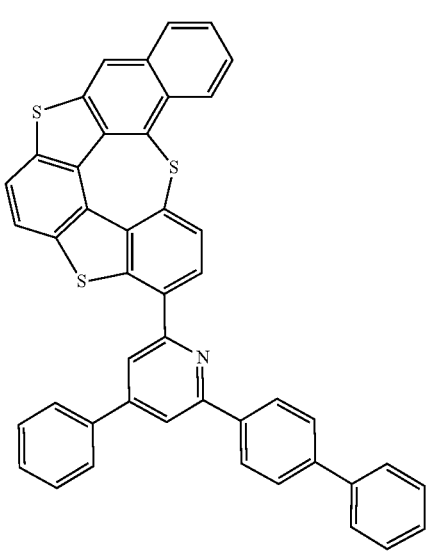
P-54
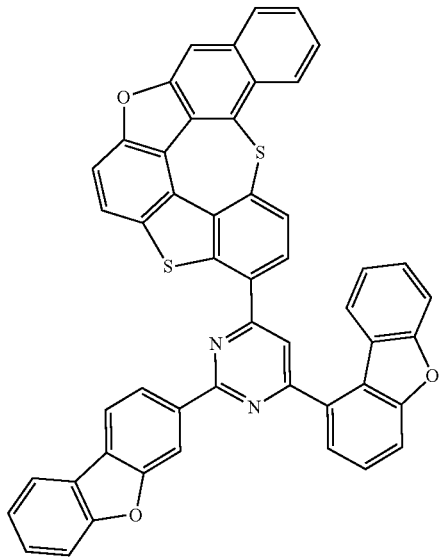

127
-continued
P-55
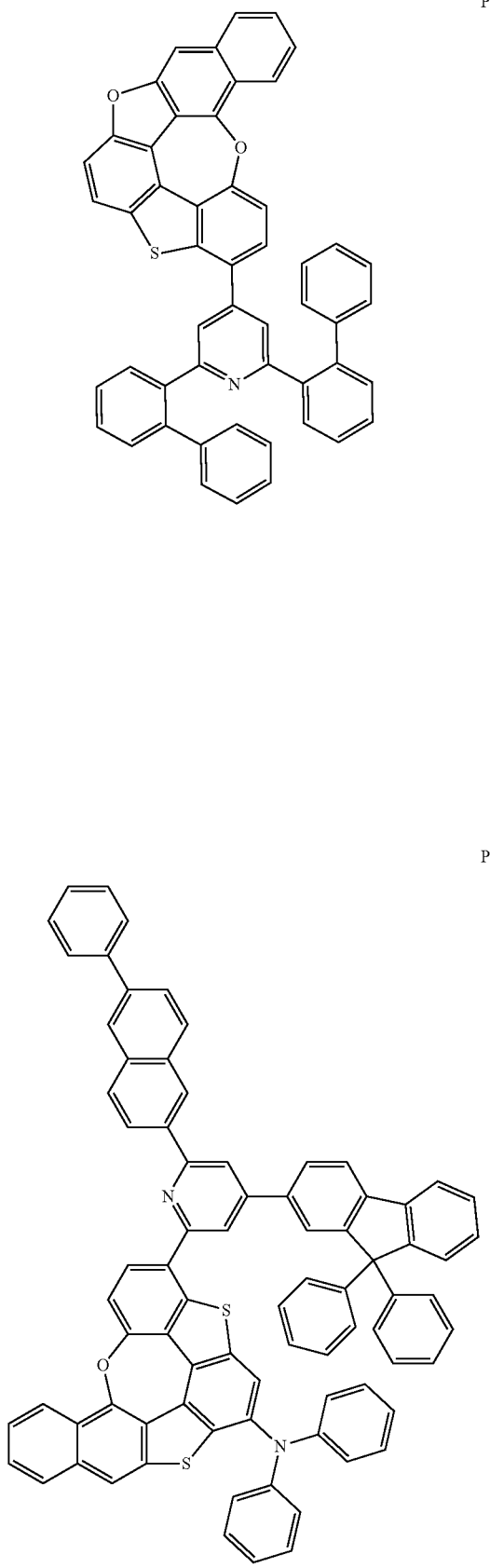
P-56
128
-continued
P-57
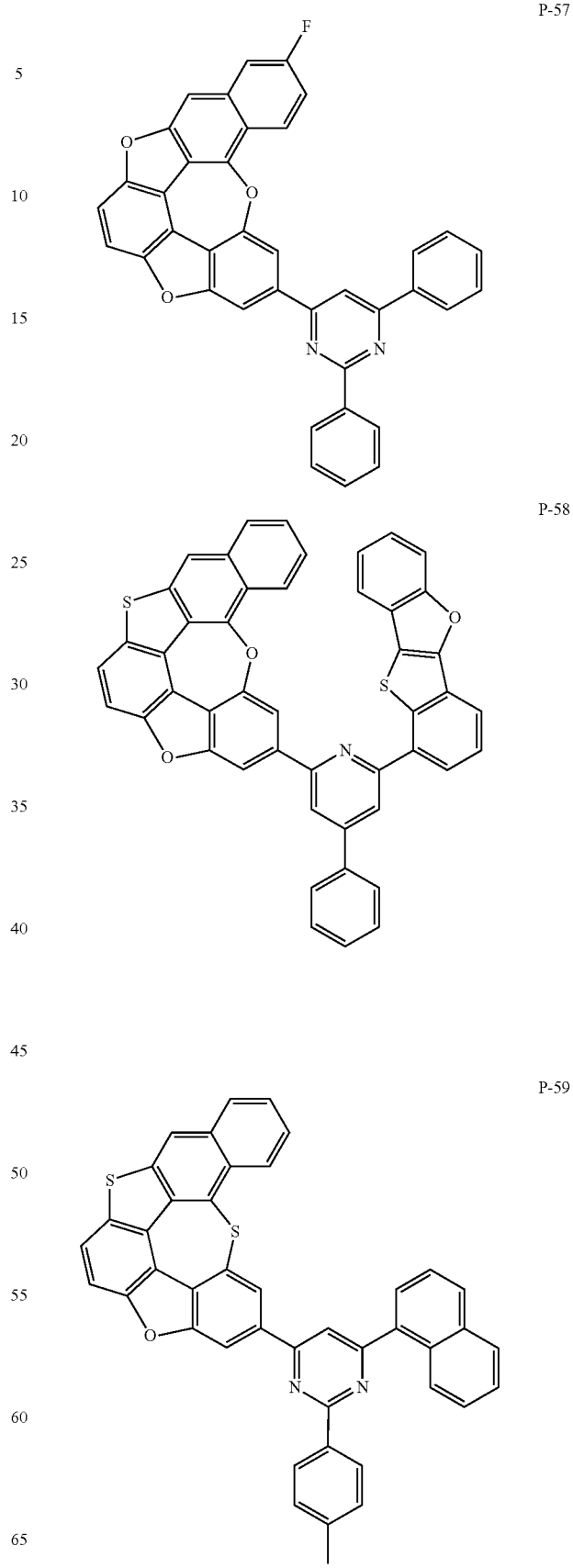
P-58
P-59

P-60
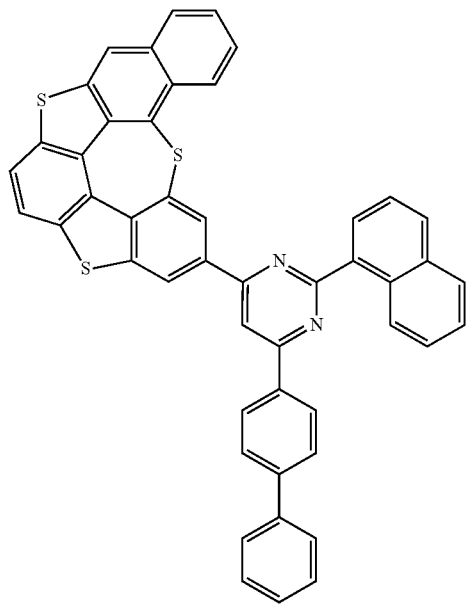
P-61
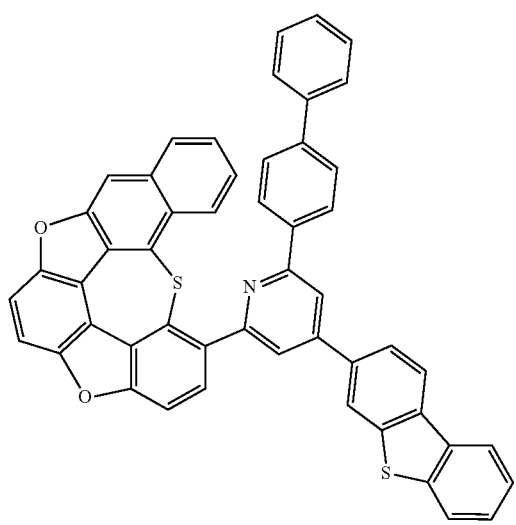
P-62
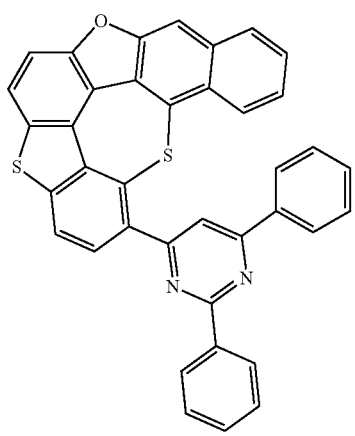
P-63
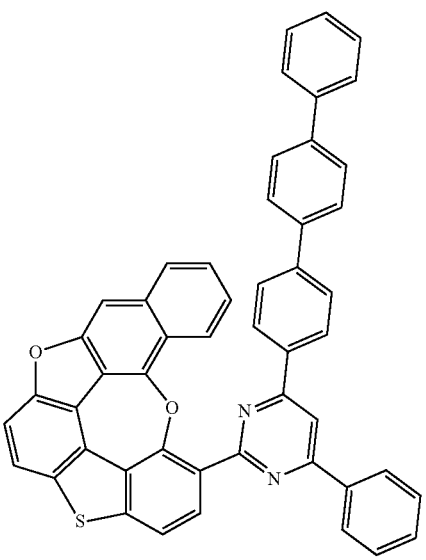
P-64
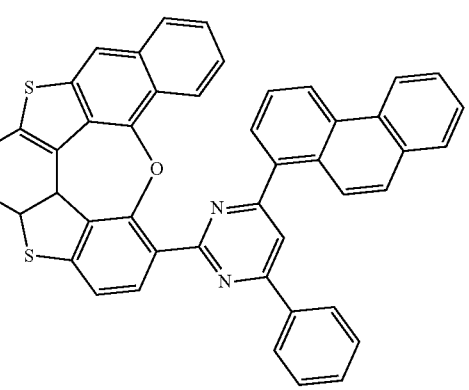
P-65
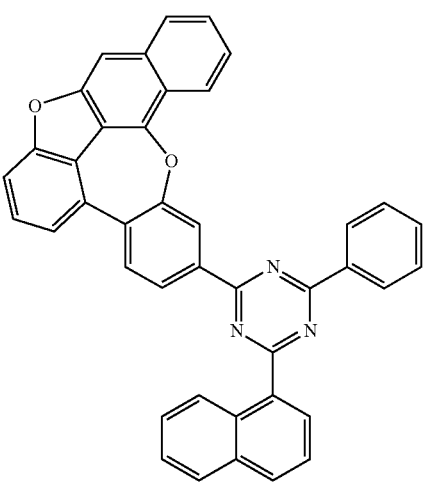

P-66
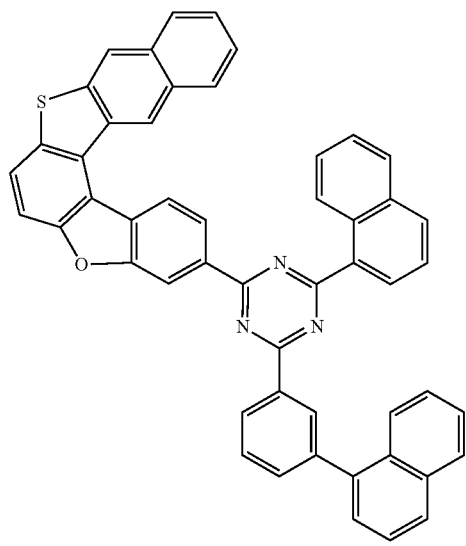
P-67
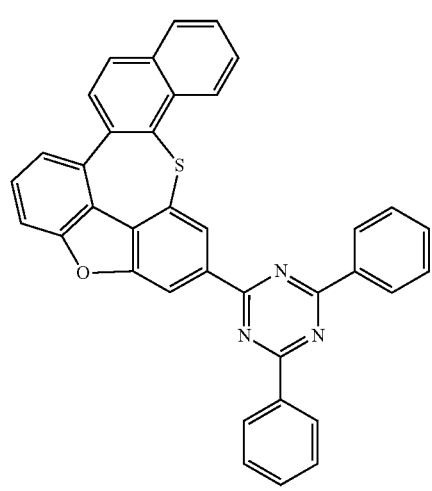
P-68
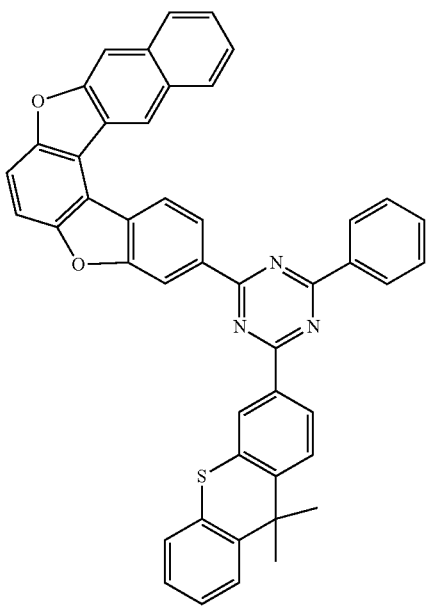
P-69
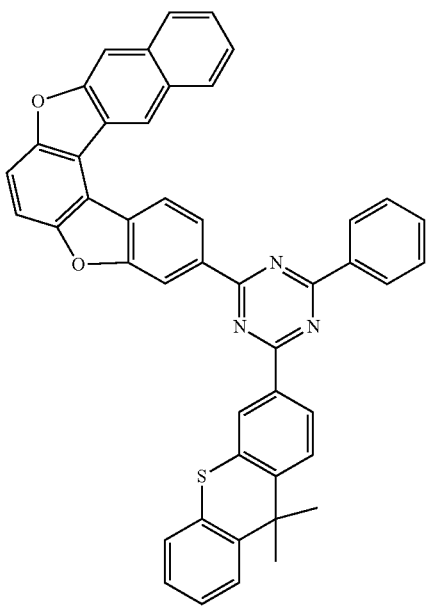
P-70
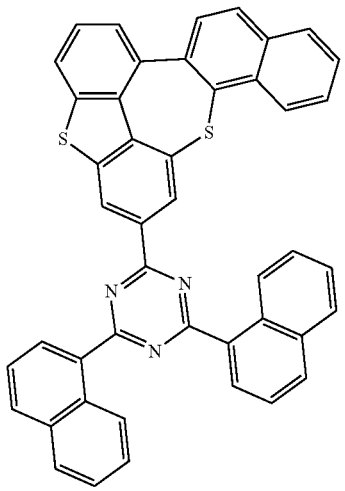

P-71
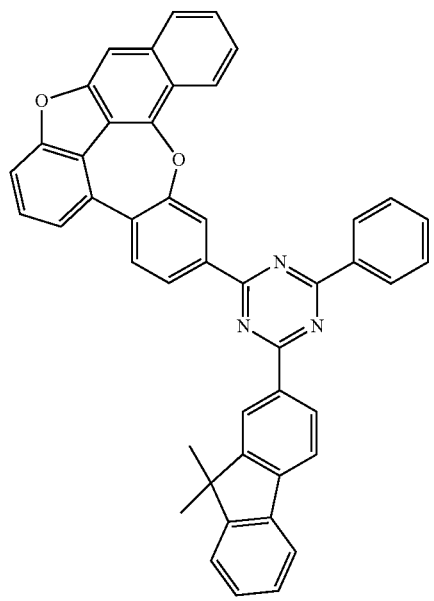
P-72
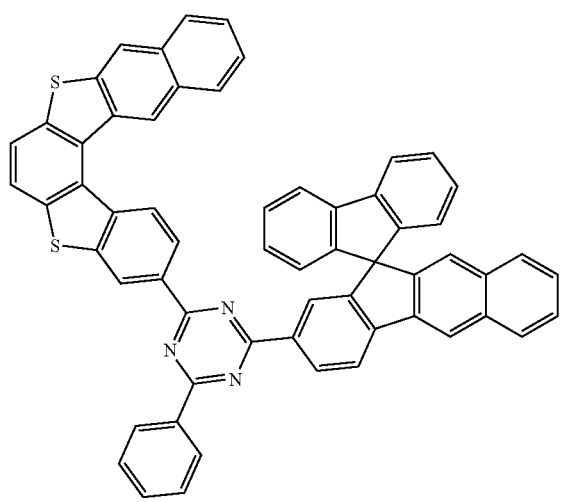
P-73
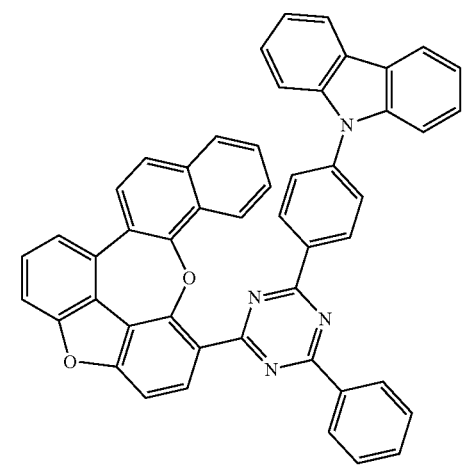
P-74
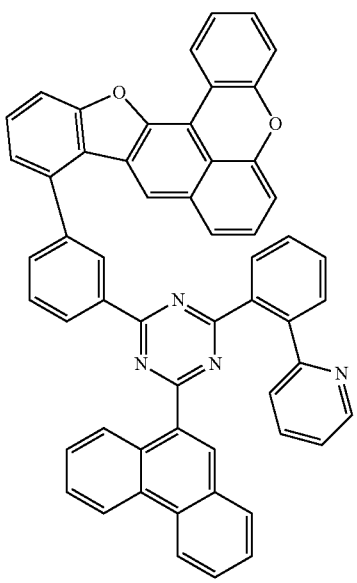
P-75
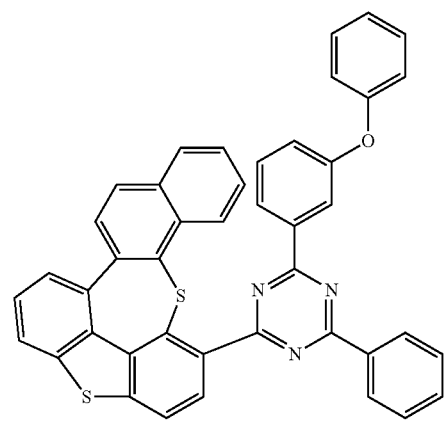
P-76

P-77

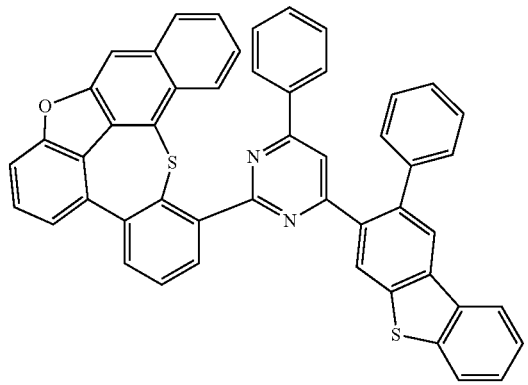

P-78

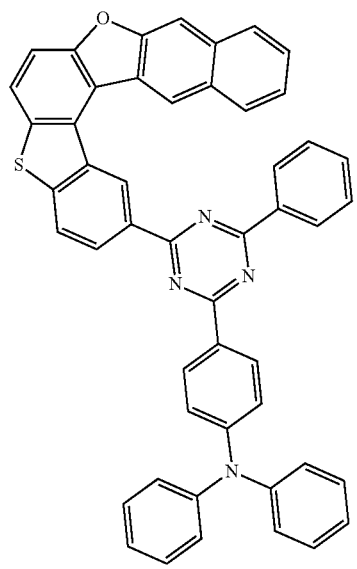

P-79

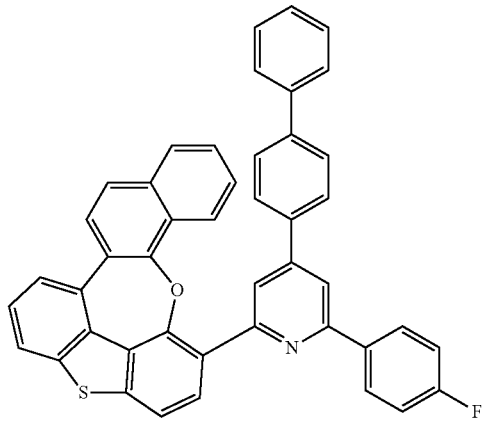

P-80

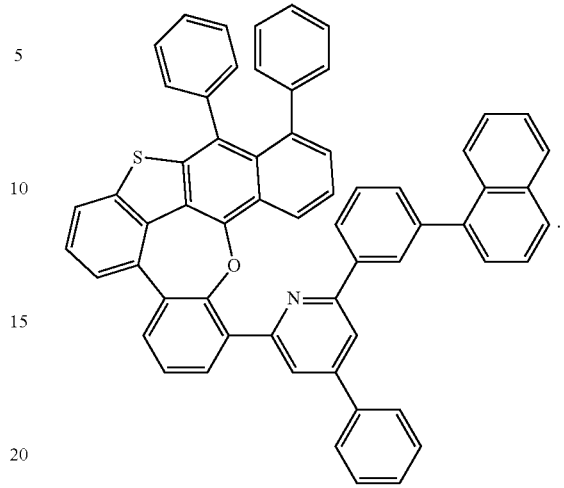

6. An organic electronic element comprising an anode, a cathode, and an organic material layer formed between the anode and the cathode, wherein the organic material layer comprises a single compound or 2 or more compounds represented by Formula 1 of claim 1.

7. The organic electronic element of claim 6, wherein the organic material layer comprises at least one of a hole injection layer, a hole transport layer, an emitting-auxiliary layer, an emitting layer, an electron transport auxiliary layer, an electron transport layer, and an electron injection layer.

8. The organic electronic element of claim 6, wherein the compound is used as a phosphorescent host material of the emitting layer.

9. The organic electronic element of claim 6, further comprising a light efficiency enhancing layer formed on at least one surface opposite to the organic material layer among one surface of the anode and the cathode.

10. The organic electronic element of claim 6, wherein the organic material layer includes at least 2 stacks including a hole transport layer, an emitting layer, and an electron transport layer sequentially formed on the anode.

11. The organic electronic element of claim 6, wherein the organic material layer further comprises a charge generating layer formed between the 2 or more stacks.

12. An electronic device comprising: a display device including the organic electronic element of claim 6; and a control unit for driving the display device.

13. The organic electronic element of claim 12, wherein the organic electronic element is any one of an organic electroluminescent device (OLED), an organic solar cell, an organic photoreceptor (OPC), an organic transistor (organic TFT), and an element for monochromic or white illumination.

* * * * *